(12) United States Patent
Rahbar et al.

(10) Patent No.: US 11,179,361 B2
(45) Date of Patent: *Nov. 23, 2021

(54) METHODS OF QUANTIFYING $N^2$-(1-CARBOXYETHYL)-2'-DEOXY-GUANOSINE (CEDG) AND SYNTHESIS OF OLIGONUCLEOTIDES CONTAINING CEDG

(71) Applicant: CITY OF HOPE, Duarte, CA (US)

(72) Inventors: Samuel Rahbar, Beverly Hills, CA (US); Timothy W. Synold, Monrovia, CA (US); John Termini, Altadena, CA (US); Gerald Wuenschell, Duarte, CA (US); Daniel Tamae, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/887,857

(22) Filed: Feb. 2, 2018

(65) Prior Publication Data

US 2018/0338939 A1 Nov. 29, 2018

Related U.S. Application Data

(60) Continuation-in-part of application No. 15/859,188, filed on Dec. 29, 2017, which is a continuation of
(Continued)

(51) Int. Cl.
*G01N 30/72* (2006.01)
*A61P 3/10* (2006.01)
(Continued)

(52) U.S. Cl.
CPC .............. *A61K 31/195* (2013.01); *A61P 3/10* (2018.01); *G01N 30/7233* (2013.01);
(Continued)

(58) Field of Classification Search
CPC .......... G01N 30/7233; G01N 30/7266; G01N 2030/8868; G01N 2030/8827; G01N 2800/042

See application file for complete search history.

(56) References Cited

U.S. PATENT DOCUMENTS 6,821,731 B2 11/2004 Gillis et al.

FOREIGN PATENT DOCUMENTS

WO    WO 1993/12258    6/1993
WO    WO 2008/145384 A1    12/2008

OTHER PUBLICATIONS

Waris et al. Journal of Diabetes Research. 2015. vol. 2015. Article ID 915486. (Year: 2015).*

(Continued)

*Primary Examiner* — Joseph G. Dauner
(74) *Attorney, Agent, or Firm* — Perkins Coie LLP; Lara J. Dueppen; Courtney Prochnow

(57) ABSTRACT

Methods of quantifying a $N^2$-(1-carboxyethyl)-2'-deoxyguanosine (CEdG) levels in biological samples and comparing those levels to known normal levels can diagnose a number of metabolic disorders or complications associated therewith, including diabetes, its associated complications, and cancer. Methods can also determine whether therapies for disorders are effective by measuring CEdG levels before and after treatment. Measurement of CEdG levels is achieved by using liquid chromatography electrospray ionization tandem mass spectrometry.

13 Claims, 40 Drawing Sheets

Specification includes a Sequence Listing.

Related U.S. Application Data application No. 14/536,299, filed on Nov. 7, 2014, now Pat. No. 9,855,233, which is a continuation of application No. 13/308,433, filed on Nov. 30, 2011, now abandoned, which is a division of application No. 12/538,854, filed on Aug. 10, 2009, now abandoned.

(60) Provisional application No. 61/087,393, filed on Aug. 8, 2008.

(51) Int. Cl.
    A61K 31/195    (2006.01)
    G01N 33/68    (2006.01)
    G01N 30/88    (2006.01)
    A61N 5/10    (2006.01)
    A61K 45/06    (2006.01)
    G01N 30/04    (2006.01)
    A61K 31/121    (2006.01)

(52) U.S. Cl.
CPC ..... *G01N 30/7266* (2013.01); *G01N 33/6893* (2013.01); *A61K 31/121* (2013.01); *A61K 45/06* (2013.01); *A61N 5/10* (2013.01); *G01N 2030/045* (2013.01); *G01N 2030/8827* (2013.01); *G01N 2030/8868* (2013.01); *G01N 2800/042* (2013.01); *G01N 2800/56* (2013.01)

(56) References Cited

OTHER PUBLICATIONS

Agadjanyan, Z.S., et al., "Cumene Peroxide and Fe2+ -Ascorbate-induced Lipid Peroxidation and Effect of Phosphoglucose Isomerase," Mol. Cell. Biochem. 289:49-53 (2006).
Ahmed, N., et al., "Methylglyoxal-Derived Hydroimidazolone Advanced Glycation End-Products of Human Lens Proteins," Invest. Ophthalmol. Vis. Sci. 44:5287-5292 (2003).
Ahmed, N., et al., "Quantitative Screening of Protein Biomarkers of Early Glycation, Advanced Glycation, Oxidation and Nitrosation in Cellular and Extracellular Proteins by Tandem Mass Spectrometry Multiple Reaction Monitoring," Biochem. Soc. Trans. 31:1417-1422 (2003).
Avril, N., et al., "Glucose Metabolism of Breast Cancer Assessed by 18F-FDG PET: Histologic and Immunohistochemical Tissue Analysis," J. Nucl. Med. 42:9-16 (2001).
Beisswenger, P., et al., "Metformin Inhibition of Glycation Processes," Diabetes Metab. 29:6S95-6S103 (2003).
Beisswenger, P. J., et al., "Metformin Reduces Systemic Methylglyoxal Levels in Type 2 Diabetes," Diabetes 48:198-202 (1999).
Besaratinia, A., et al., "Similar Mutagenicity of Photoactivated Porphyrins and Ultraviolet A Radiation in Mouse Embryonic Fibroblasts: Involvement of Oxidative DNA Lesions in Mutagenesis," Biochem. 43:15557-15566 (2004).
Bidmon, C., et al., "Analysis of DNA-Bound Advanced Glycation End-Products by LC and Mass Spectrometry," J. Chromatography 855:51-58 (2007).
Bierhaus, A., et al., "Understanding RAGE, The Receptor for Advanced Glycation End Products," J. Mol. Med. 83:876-886 (2005).
Bos, R., et al., "Biologic Correlates of 18Fluorodeoxyglucose Uptake in Human Breast Cancer Measured by Positron Emission Tomography," J. Clin. Oncol. 20:379-387 (2002).
Bourajjaj, M., et al., "Role of Methylglyoxal Adducts in the Development of Vascular Complications in Diabetes Mellitus," Biochem. Soc. Trans. 31:1400-1402 (2003).
Breitling-Utzmann, C. M., et al., "Identification and Quantification of Phosphatidylethanolamine-Derived Glucosylamines and Aminoketoses from Human Erythrocytes—Influence of Glycation Products on Lipid Peroxidation," Arch. Biochem. Biophys. 391:245-254 (2001).
Brown, B. E., et al., "Hydrazine Compounds Inhibit Glycation of Low-Density Lipoproteins and Prevent the In Vitro Formation of Model Foam Cells from Glycolaldehyde-Modified Low-Density Lipoproteins," Diabetologia 49:775-783 (2006).
Bulteau, A.L., et al., "Proteasome Inhibition in Glyoxal-treated Fibroblasts and Resistance of Glycated Glucose-6-phosphate Dehydrogenase to 20 S Proteasome Degradation in Vitro," J. Biol. Chem. 276:45662-45668 (2001).
Cadet, J., et al., "Facts and Artifacts in the Measurement of Oxidative Base Damage to DNA," Free Rad. Res. 29:541-550 (1998).
Cao, H., et al., "Stereospecific Synthesis and Characterization of Oligodeoxyribonucleotides Containing an N2-(1-Carboxyethyl)-2'-Deoxyguanosine," J. Am. Chem. Soc. 129:12123-12130 (2007).
Casazza, J. P., et al., "The Metabolism of Acetone in Rat," J. Biol. Chem. 259:231-236 (1984).
Chao, M.R., et al., "Rapid and Sensitive Quantification of Urinary N7-Methylguanine by Isotope-Dilution Liquid Chromatography/Electrospray Ionization Tandem Mass Spectrometry with On-Line Solid-Phase Extraction," Rapid Commun. Mass Spectrom. 19:2427-2432 (2005).
Chaplen, F. W.R., et al., "Detection of Methylglyoxal as a Degradation Product of DNA and Nucleic Acid Components Treated with Strong Acid," Anal. Biochem. 236:262-269 (1996).
Chaplen, F. W.R., et al. "Evidence of High Levels of Methylglyoxal in Cultured Chinese Hamster Ovary Cells," PNAS USA 95:5533-5538 (1998).
Cowey, S., et al., "The Metabolic Syndrome: A High-Risk State for Cancer?" Am. J. Pathol. 169:1505-1522 (2006).
Creighton, D. J., et al., "Brief History of Glyoxalase I and What We Have Learned About Metal Ion-Dependent, Enzyme-Catalyzed Isomerizations," Arch. Biochem. Biophys. 387:1-10 (2001).
The Diabetes Control and Complications Trial Research Group, "The Effect of Intensive Treatment of Diabetes on the Development and Progression of Long-Term Complications in Insulin-Dependent Diabetes Mellitus," New Engl. J. Med. 329(14):977-986 (1993).
Edelman, D., et al., "Utility of Hemoglobin A1c in Predicting Diabetes Risk," J. Gen. Intern. Med. 19:1175-1180 (2004).
Epidemiology of Diabetes Interventions and Complications (EDIC) Research Group, "Epidemiology of Diabetes Interventions and Complications (EDIC): Design, Implementation, and Preliminary Results of a Long-Term Follow-Up of the Diabetes Control and Complications Trial Cohort," Diabetes Care 22(1):99-111 (1999).
Eriksson, U. J., et al., "Teratogenicity of 3-Deoxyglucosone and Diabetic Embryopathy," Diabetes 47:1960-1966 (1998).
Escodd, "Comparison of Different Methods of Measuring 8-Oxoguanine as a Marker of Oxidative DNA Damage," Free Rad. Res. 32:333-341 (2000).
Feinberg, A. P., et al., "Hypomethylation Distinguishes Genes of Some Human Cancers from Their Normal Counterparts," Nature 301:89-92 (1983).
Figarola, J. L., et al., "LR-90 A New Advanced Glycation Endproduct Inhibitor Prevents Progression of Diabetic Nephropathy in Streptozotocin-Diabetic Rats," Diabetologia 46:1140-1152 (2003).
Figarola, J. L., et al., "Renoprotective and Lipid-Lowering Effects of LR Compounds, Novel Advanced Glycation End Product Inhibitors, in Streptozotocin-Induced Diabetic Rats," Ann. N.Y. Acad. Sci. 1043:767-776 (2005).
Figarola, J. L., et al., "Prevention of Early Renal Disease, Dyslipidaemia and Lipid Peroxidation in STZ-Diabetic Rats by LR-9 and LR-74, Novel AGE Inhibitors," Diabetes/Metabolism Research and Reviews 21:533-544 (2005).
Fosmark, D. S., et al., "Increased Serum Levels of the Specific Advanced Glycation End Product Methylglyoxal-Derived Hydroimidazolone are Associated with Retinopathy in Patients with Type 2 Diabetes Mellitus," Metab. Clin. Exper. 55:232-236 (2006).
Freire, A. P., et al., "Anti-Glycation Defences in Yeast," Biochem. Soc. Trans. 31:1409-1412 (2003).
Frischmann, M., et al., "Identification of DNA Adducts of Methylglyoxal," Chem. Res. Toxicol. 18:1586-1592 (2005).

(56) References Cited

OTHER PUBLICATIONS

Frolov, A., et al., "Fragmentation Behavior of Glycated Peptides Derived from D-Glucose, D-Fructose and D-Ribose in Tandem Mass Spectrometry," J. Mass Spectrom. 41:1459-1469 (2006).
Fu, M.X., et al., "The Advanced Glycation End Product, Nepsilon-(Carboxymethyl)lysine, Is a Product of both Lipid Peroxidation and Glycoxidation Reactions," J. Biol. Chem. 271:9982-9986 (1996).
Fukunaga, M., et al., "Methylglyoxal Induces Apoptosis Through Oxidative Stress-Mediated Activation of p38 Mitogen-Activated Protein Kinase in Rat Schwann Cells," Ann. N.Y. Acad. Sci. 1043:151-157 (2005).
Gaby, A. R., "Adverse Effects of Dietary Fructose," Alt. Med. Rev. 10:294-306 (2005).
Godschalk, R.W.L., et al., "Influences of DNA Isolation and RNA Contamination on Carcinogen-DNA Adduct Analysis by 32P-Postlabeling," Environ. Mol. Mutagen. 32:344-350 (1998).
Gomes, R. A., et al., "Protein Glycation in *Saccharomyces cerevisiae* Argpyrimidine Formation and Methylglyoxal Catabolism," FEBS J. 272:4521-4531 (2005).
Han, Y., et al., "Plasma Methylglyoxal and Glyoxal are Elevated and Related to Early Membrane Alteration in Young, Complication-Free Patients with Type 1 Diabetes," Mol. Cell. Biochem. 305:123-131 (2007).
Huang, J.S., et al., "Role of Receptor for Advanced Glycation End-Product (RAGE) and the JAK/STAT-Signaling Pathway in AGE-Induced Collagen Production in NRK-49F Cells," J. Cell. Biochem. 81:102-113 (2001).
Inagi, R., et al., "Severe Diabetic Nephropathy Model With Early Development of Nodule-Like Lesions Induced by Megsin Overexpression in RAGE/iNOS Transgenic Mice," Diabetes 55:356-366 (2006).
Kavarana, M. J., et al., "Mechanism-Based Competitive Inhibitors of Glyoxalase I: Intracellular Delivery, In Vitro Antitumor Activities, and Stabilities in Human Serum and Mouse Serum," J. Med. Chem. 42:221-228 (1999).
Koc, H., et al., "Applications of Mass Spectrometry for Quantitation of DNA Adducts," J. Chromatogr. 778:323-343 (2002).
La Vecchia, C., et al., "A Case-Control Study of Diabetes Mellitus and Cancer Risk," Br. J. Cancer 70:950-953 (1994).
Lee, A. T., et al., "A Role for DNA Mutations in Diabetes-Associated Teratogenesis in Transgenic Embryos," Diabetes 44:20-24 (1995).
Lee, E. K., et al., "Inhibition of Aldose Reductase Enhances HeLa Cell Sensitivity to Chemotherapeutic Drugs and Involves Activation of Extracellular Signal-Regulated Kinases," Anti-Cancer Drugs 13:859-868 (2002).
Lerman, J., "Study Design n Clinical Research: Sample Size Estimation and Power Analysis," Can J. Anaesth. 43(2):184-191 (1996).
Li, H., et al., "N2-Carboxyethyl-20-deoxyguanosine, A DNA Glycation Marker, in Kidneys and Aortas of Diabetic and Uremic Patients," Kidney Int. 69:388-392 (2006).
Li, Y., et al., "Nonenzymatic Glycation of Guanosine 50-Triphosphate by Glyceraldehyde: An In Vitro Study of AGE Formation," Bioorganic Chemistry 35:417-429 (2007).
Liu, B.F., et al., "Methylglyoxal Induces Apoptosis Through Activation of p38 Mitogen-Activated Protein Kinase in Rat Mesangial Cells," Kidney Int. 63:947-957 (2003).
Lo, T. W.C., et al. "Binding and Modification of Proteins by Methylglyoxal Under Physiological Conditions: A Kinetic and Mechanistic Study with Na-Acetylarginine, NU-Acetylcysteine, and Na-Acetyllysine, and Bovine Serum Albumin," J. Biol. Chem. 269:32299-32305 (1994).
Lo, T. W. C., et al., "The Reaction of Methylglyoxal with Aminoguanidine Under Physiological Conditions and Prevention of Methylglyoxal Binding to Plasma Proreins," Biochem. Pharmacol. 48:1865-1870 (1994).
Markesbery, W. R., "Oxidative Stress Hypothesis in Alzheimer's Disease," Free Radical Biol. Med. 23:134-147 (1997).
Miyata, T., et al., "Glyoxalase I Deficiency is Associated With an Unusual Level of Advanced Glycation End Products in a Hemodialysis Patient," Kidney Int. 60:2351-2359 (2001).
Miyata, T., et al., "Mechanism of the Inhibitory Effect of OPB-9195 [(±)-2-Isopropylidenehydrazono-4-Oxo-Thiazolidin-5-Ylacetanilide] on Advanced Glycation End Product and Advanced Lipoxidation End Product Formation," J. Am. Soc. Nephrol. 11:1719-1725 (2000).
Miyazawa, T., et al., "Tandem Mass Spectrometry Analysis of Amadori-Glycated Phosphatidylethanolamine in Human Plasma," Ann. N.Y. Acad. Sci. 1043:280-283 (2005).
Murata-Kamiya, N., et al., "Methylglyoxal Induces G:C to C:G and G:C to T:A Transversions in the supF Gene on a Shuttle Vector Plasmid Replicated in Mammalian Cells," Mut. Res. 468:173-182 (2000).
Nakagawa, K., et al., "Ion-Trap Tandem Mass Spectrometric Analysis of Amadori-Glycated Phosphatidylethanolamine in Human Plasma With or Without Diabetes," J. Lipid Res. 46:2514-2524 (2005).
Nemet, I., et al., "Methylglyoxal in Food and Living Organisms," Mol. Nutr. Food Res. 50:1105-1117 (2006).
Norberg, M., et al., "A Combination of HbA1c, Fasting Glucose and BMI is Effective in Screening for Individuals at Risk of Future Type 2 Diabetes: OGTT is Not Needed," J. Intern. Med. 260:263-271 (2006).
Oak, J.H., et al., "Amadori-Glycated Phosphatidylethanolamine Induces Angiogenic Differentiations in Cultured Human Umbilical Vein Endothelial Cells," FEBS Letters 555:419-423 (2003).
Ochs, S., et al., "Reaction of 2'-Deoxyguanosine with Glyceraldehyde," Liebigs Ann. Chem. 851-853 (1994).
Papoulis, A., et al., "Identification of N2-(1-Carboxyethyl)Guanine (CEG) as a Guanine Advanced Glycosylation End Product," Biochem. 34:648-655 (1995).
Phillips, S. A., et al., "Modification of the Glyoxalase System in Streptozotocin-Induced Diabetic Rats," Biochem. Pharmacol. 46:805-811 (1993).
Phillips, S. A., et al., "The Formation of Methylglyoxal from Triose Phosphates: Investigation Using a Specific Assay for Methylglyoxal," Eur. J. Biochem. 212:101-105 (1993).
Pischetsrieder, M., et al., "N2-(1-Carboxyethyl)Deoxyguanosine, A Nonenzymatic Glycation Adduct of DNA, Induces Single-Strand Breaks and Increases Mutation Frequencies," Biochem. Biophys. Res. Comm. 264:544-549 (1999).
Price, D. L., et al., "Chelating Activity of Advanced Glycation End-product Inhibitors," J. Biol. Chem. 276: 48967-48972 (2001).
Rachman, H., et al., "Critical Role of Methylglyoxal and AGE in Mycobacteria-Induced Macrophage Apoptosis and Activation," PLoS One 1:e29 (2006).
Rahbar, S., "Novel Inhibitors of Advanced Glycation Endproducts," Arch. Biochem. Biophys. 419:63-79 (2003).
Rahbar, S., "Novel Inhibitors of Glycation and AGE Formation," Cell Biochem. Biophys. 48:147-157 (2007).
Rahbar, S., et al., "Studies of an Unusual Hemoglobin in Patients with Diabetes Mellitus," Biochem. Biophys. Res. Commun. 36:838-843 (1969).
Rahbar, S., "The Discovery of Glycated Hemoglobin A Major Event in the Study of Nonenzymatic Chemistry in Biological Systems," Ann. N.Y. Acad. Sci. 1043: 9-19 (2005).
Ravandi, A., et al., "Isolation and Identification of Glycated Aminophospholipids from Red cells and Plasma of Diabetic Blood," FEBS Letters 381:77-81 (1996).
Rodriguez, H., et al., "Comparison of the Levels of 8-Hydroxyguanine in DNA as Measured by Gas Chromatography Mass Spectrometry Following Hydrolysis of DNA by *Escherichia coli* Fpg Protein or Formic Acid," Nucleic Acids Res. 28:e75 (2000).
Rosenstock, J., et al., "Triple Therapy in Type 2 Diabetes: Insulin Glargine or Rosiglitazone Added to Combination Therapy of Sulfonylurea Plus Metformin in Insulin-Naïve Patients," Diabetes Care 29:554-559 (2006).
Rulli, A., et al., "Expression of Glyoxalase I and II in Normal and Breast Cancer Tissues," Breast Cancer Res. Treat. 66:67-72 (2001).
Sakamoto, H., et al., "Selective Activation of Apoptosis Program by S-p-bromobenzylglutathione Cyclopentyl Diester in Glyoxalase I-Overexpressing Human Lung Cancer Cells," Clin. Cancer Res. 7:2513-2518 (2001).

(56) References Cited

OTHER PUBLICATIONS

Schalkwijk, C. G., et al., "Heat-Shock Protein 27 is a Major Methylglyoxal-Modified Protein in Endothelial Cells," FEBS Letters 580:1654-1570 (2006).
Schneider, M., et al., "Detection of DNA-Bound Advanced Glycation End-Products by Immunoaffinity Chromatography Coupled to HPLC-Diode Array Detection," Mol. Nutr. Food Res. 50:424-429 (2006).
Schneider, M., et al., "Determination of Glycated Nucleobases in Human Urine by a New Monoclonal Antibody Specific for N2-Carboxyethyl-2'-Deoxyguanosine," Chem. Res. Toxicol. 17:1385-1390 (2004).
Schupp, N., et al., "Genotoxicity of Advanced Glycation End Products Involvement of Oxidative Stress and of Angiotensin II Type 1 Receptors," Ann. N.Y. Acad. Sci. 1043: 685-695 (2005).
Sebekova, K., et al., "Genomic Damage and Malignancy in End-Stage Renal Failure: Do Advanced Glycation End Products Contribute?" Kidney Blood Press. Res. 30:56-66 (2007).
Seidel, W., et al., "DNA-Glycation Leads to Depurination by the Loss of N2-Carboxyethylguanine In Vitro," Cell. Mol. Biol. 44:1165-1170 (1998).
Seidel, W., et al., "Immunochemical Detection of N2-[1-(1-carboxy)ethyl]guanosine, An Advanced Glycation End Product Formed by the Reaction of DNA and Reducing Sugars or L-Ascorbic Acid In Vitro," Biochim. Biophys. Acta 1425:478-484 (1998).
Shimoi, K., et al., "Oxidative DNA Damage Induced by High Glucose and Its Suppression in Human Umbilical Vein Endothelial Cells," Mut. Res. 480-481:371-378 (2001).
Shinohara, M., et al., "Overexpression of Glyoxalase-I in Bovine Endothelial Cells Inhibits Intracellular Advanced Glycation Endproduct Formation and Prevents Hyperglycemia-Induced Increases in Macromolecular Endocytosis," J. Clin. Invest. 101:1142-1147 (1998).
Shoda, H., et al., "Inhibitory Effects of Tenilsetam on the Maillard Reaction," Endocrinology 138:1886-1892 (1997).
Singh, R., et al., "Liquid Chromatography-Electrospray Ionization-Mass Spectrometry: The Future of DNA Adduct Detection," Carcinogenesis 27:178-196 (2006).
Suji, G., et al., "DNA Damage by Free Radical Production by Aminoguanidine," Ann. N.Y. Acad. Sci. 1067:191-199 (2006).
Synold, T., et al., "Advanced Glycation End Products of DNA: Quantification of N2-(1-Carboxyethyl)-2'-Deoxyguanosine in Biological Samples by Liquid Chromatography Electrospray Ionization Tandem Mass Spectrometry," Chem. Res. Toxicol. 21:2148-2155 (2008).
Taghizadeh, K., et al., "Quantification of DNA Damage Products Resulting from Deamination, Oxidation and Reaction with Products of Lipid Peroxidation by Liquid Chromatography Isotope Dilution Tandem Mass Spectrometry," Nature Protocols 3:1287-1298 (2008).
Tamae, D., et al., "Mutagenesis and Repair Induced by the DNA Advanced Glycation End Product $N^2$-1-(Carboxyethyl)-2'-Deoxyguanosine in Human Cells," Biochem. 50(12):2321-2329 (2011).
Thisted, R. A., "What is a P-Value?" The Univ. of Chicago (1998) http://www.stat.uchicago.edu/~thisted.
Thornalley, P. J., et al., "Advances in Glyoxalase Research. Glyoxalase Expression in Malignancy, Anti-Proliferative Effects of Methylglyoxal, Glyoxalase I Inhibitor Diesters and S-D-Lactoylglutathione, and Methylglyoxal-Modified Protein Binding and Endocytosis by the Advanced Glycation Endproduct Receptor," Crit. Rev. Oncol. Hematol. 20:99-128 (1995).
Thornalley, P. J., et al., "The Enzymatic Defence Against Glycation in Health, Disease and Therapeutics," Biochem. Soc. Trans. 31:1341-1342 (2003).
Thornalley, P. J., et al., "Formation of Glyoxal, Methylglyoxal and 3-Deoxyglucosone in the Glycation of Proteins by Glucose," Biochem. J. 344:109-116 (1999).
Thornalley, P. J., et al., "Glutathione-Dependent Detoxification of α-Oxoaldehydes by the Glyoxalase System: Involvement in Disease Mechanisms and Antiproliferative Activity of Glyoxalase I Inhibitors," Chemico-Biological Interactions 111-112:137-151 (1998).
Thornalley, P. J., et al., "Kinetics and Mechanism of the Reaction of Aminoguanidine with the α-Oxoaldehydes Glyoxal, Methylglyoxal, and 3-Deoxyglucosone Under Physiological Conditions," Biochem. Pharmacol. 60:55-65 (2000).
Thornalley, P. J., "Protecting the Genome: Defence Against Nucleotide Glycation and Emerging Role of Glyoxalase I Overexpression in Multidrug Resistance in Cancer Chemotherapy," Biochem. Soc. Trans. 31:1372-1377 (2003).
Thornalley, P. J., et al., "Quantitative Screening of Advanced Glycation Endproducts in Cellular and Extracellular Proteins by Tandem Mass Spectrometry," Biochem. J. 375:581-592 (2003).
Vaca, C. E., et al., "Formation of DNA Adducts in Human Buccal Epithelial Cells Exposed to Acetaldehyde and Methylglyoxal In Vitro," Chemico-Biological Interactions 108:197-208 (1998).
Van Heijst, J. W., et al., "Advanced Glycation End Products in Human Cancer Tissues: Detection of Nepsilon-(Carboxymethyl)lysine and Argpyrimidine," Ann. N.Y. Acad. Sci. 1043:725-733 (2005).
Van Heijst, J. W.J., et al., "Argpyrimidine-Modified Heat Shock Protein 27 in Human Non-Small Cell Lung Cancer: A Possible Mechanism for Evasion of Apoptosis," Cancer Letters 241:309-319 (2006).
Vander Jagt, D. L., "Methylglyoxal, Diabetes Mellitus and Diabetic Complications," Drug Metab. Drug Interact. 23:93-124(2008).
Vander Jagt, D. L., et al., "Methylglyoxal Metabolism and Diabetic Complications: Roles of Aldose Reductase, Glyoxalase-I, Betaine Aldehyde Dehydrogenase and 2-Oxoaldehyde Dehydrogenase," Chemico-Biological Interactions 143-144:341-351 (2003).
Vander Jagt, D. L., et al., "Reduction of Trioses by NADPH-Dependent Aldo-Keto Reductases," J. Biol. Chem. 267:4364-4369 (1992).
Wautier, J.L., "Protein Glycation: A Firm Link to Endothelial Cell Dysfunction," Circ. Res. 95:233-238 (2004).
Wells-Knecht, K. J., et al., "Mechanism of Autoxidative Glycosylation Identification of Glyoxal and Arabinose as Intermediates in the Autoxidative Modification of Proteins by Glucose," Biochem. 34:3702-3709 (1995).
Wondrak, G. T., et al., "Identification of α-Dicarbonyl Scavengers for Cellular Protection Against Carbonyl Stress," Biochem. Pharmacol. 63:361-373 (2002).
Wu, L., et al., "Troglitazone Selectively Inhibits Glyoxalase I Gene Expression," Diabetologia 44:2004-2012 (2001).
Yabe-Nishimura, C., et al., "Up-Regulation of Aldose Reductase by the Substrate, Methylglyoxal," Chemico-Biological Interactions 143-144:317-323 (2003).
Yao, D., et al., "Methylglyoxal Modification of mSin3A Links Glycolysis to Angiopoietin-2 Transcription," Cell 124:275-286 (2006).
Yeh, C.H., et al., "Requirement for p38 and p44/p42 Mitogen-Activated Protein Kinases in RAGE-Mediated Nuclear Factor-kB Transcriptional Activation and Cytokine Secretion," Diabetes 50:1495-1504 (2001).
Yim, H.S., et al., "Free Radicals Generated During the Glycation Reaction of Amino Acids by Methylglyoxal," J. Biol. Chem. 270:28228-28233 (1995).

* cited by examiner

Fig. 27A
Fig. 27B
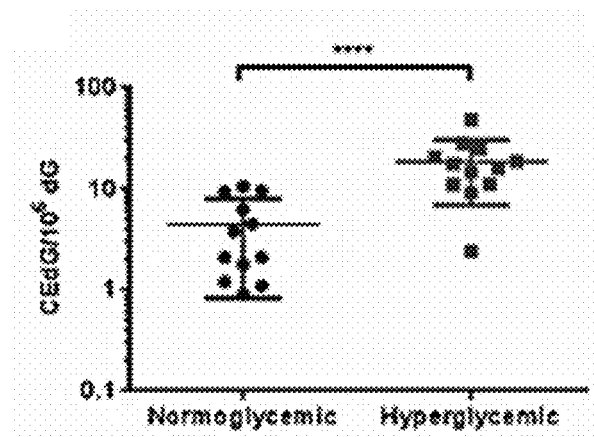
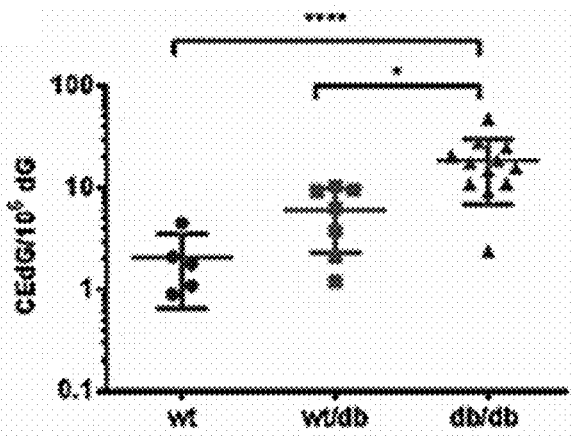
Fig. 27C
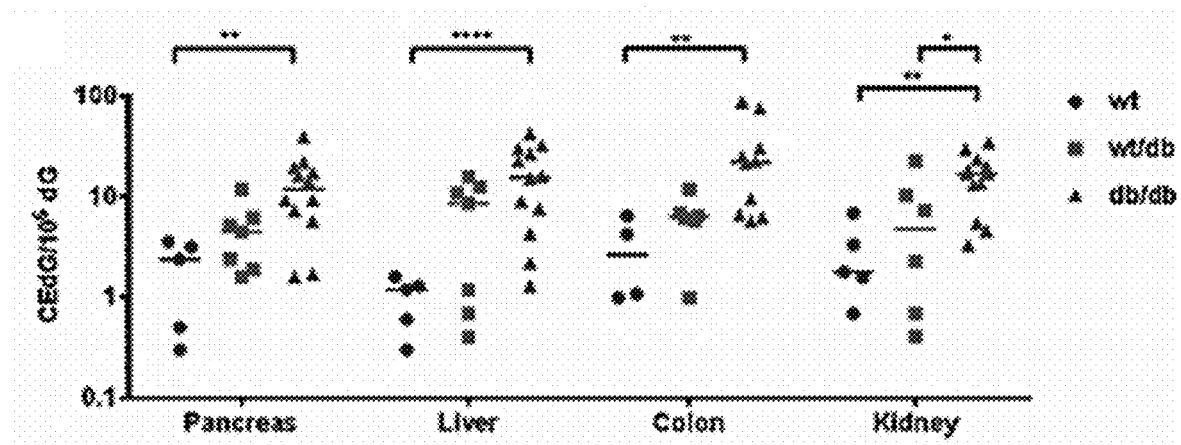
Fig. 27D

+/db; n=16
db/db; n=15

METHODS OF QUANTIFYING N²-(1-CARBOXYETHYL)-2'-DEOXY-GUANOSINE (CEDG) AND SYNTHESIS OF OLIGONUCLEOTIDES CONTAINING CEDG

PRIORITY CLAIM

This application is a continuation-in-part of U.S. patent application Ser. No. 15/859,188, filed Dec. 29, 2017, which is a continuation of U.S. patent application Ser. No. 14/536,299, filed Nov. 7, 2014, issued as U.S. Pat. No. 9,855,233, which is a continuation of U.S. patent application Ser. No. 13/308,433, filed Nov. 30, 2011, abandoned, which is a divisional of U.S. patent application Ser. No. 12/538,854, filed Aug. 10, 2009, abandoned, which claims priority to U.S. Provisional Application Ser. No. 61/087,393, filed Aug. 8, 2008, the contents of which are incorporated herein by reference in their entireties.

GOVERNMENT INTEREST

The present invention was made partially with government support under Grant Nos. P30 CA33572, and R01CA176611, awarded by National Institutes of Health. The government has certain rights in the present invention.

BACKGROUND

Hyperglycemia increases circulating levels of glucose-derived α-oxoaldehydes such as methylglyoxal (MG) which react non-enzymatically with proteins, lipids, and nucleic acids to form AGEs, potentially modifying or inactivating their function. Unlike Amadori adducts such as HbA1c and fructosamine, which are formed reversibly in equilibrium with glucose, AGEs are typically irreversible and possess long lifetimes. Since CEdG is only known to be formed from the reaction of MG with dG, they may be considered stable surrogate biomarkers of MG exposure. MG has been shown to be significantly elevated in both type 1 and type 2 diabetes. Several endogenous sources of MG have been described including the non-enzymatic decomposition of glucose and its Amadori adducts, ketone body metabolism, and glycolysis. All of these processes are exacerbated by diabetes, and elevated circulating MG has not been clearly associated with any other diseases or environmental toxin exposure.

Also, MG is a highly reactive electrophile and is present at micromolar levels in many foods and most living organisms. MG is a major environmental breakdown product of carbohydrates. MG is also generated biochemically during glycolysis via elimination of phosphate from the common enediol intermediate resulting from deprotonation of dihydroxyacetone phosphate and glyceraldehyde 3-phosphate. Additional endogenous sources of MG include the catabolism of threonine and the P450 mediated oxidation of ketone bodies and the oxidative breakdown of DNA and RNA under acidic conditions. MG is a probable mutagen in vivo.

Methylglyoxal induces G>T and G>C transversions, as well as a large number (50%) of multibase deletions. Since 89% of the base substitution mutations are observed at guanosine, and N²-(1-carboxyethyl)-2'-deoxyguanosine (CEdG) is the predominant adduct formed from reaction of MG with DNA, this pattern of transversions arises from CEdG (as primer extension assays using oligonucleotide templates containing CEdG have evidenced). The presence of CEdG in DNA has also been shown to induce single-strand breaks, suggesting an alternative mechanism by which this adduct may contribute to genetic instability.

Glycation results when a sugar, such as fructose or glucose, non-enzymatically links to a protein or lipid. Glycation typically impairs the function of the molecules to which it binds. Methylglyoxal reacts readily with nucleophilic moieties on proteins, lipids and DNA to produce covalent adducts known as advanced glycation end-products (AGEs). Protein AGEs are well characterized and have been proposed to play a role in the various pathologies associated with diabetes, cancer, aging, and Alzheimer's disease. The first clear correlation between abnormal levels of a protein-AGE and a human disease (diabetes) was described in 1969 for the hemoglobin A1c (HbA1c) adduct by Rahbar et al. Since then, HbA1c has become a commonly used biomarker for the diagnosis and treatment monitoring of diabetes.[11-13] Accordingly, there is continued interest in the development of novel, more sensitive assays for the quantitative measurement of biomolecule-derived AGEs to complement and extend the clinical biomarker repertoire, as well as to assist in elucidating their role in pathology.

Protein AGEs, formed from reactions of carbohydrate-derived α-oxoaldehydes such as methylglyoxal (MG) with amino acid nucleophiles, are elevated as a result of hyperglycemia and have been previously investigated as clinical biomarkers of glucose control and diabetic complications. Although there are numerous reports describing the correlation of various protein AGEs with hyperglycemia and diabetic complications, predictive power depends upon the exact combination of AGEs studied and the assay matrix (e.g. serum, collagen) examined. For example, protein AGEs in serum and collagen are also significantly elevated in obese/diabetic individuals and have been proposed as potential biomarkers of diabetic complications. In the Joslin Medalist study of patients with type 1 diabetes for ≥50 years, a specific combination of plasma protein AGEs was shown to be more accurate than HbA1c for the prediction of complications. However, it is difficult to compare data from various correlative studies on protein AGEs because different quantitative and semi-quantitative methods including gas chromatography (GC) and liquid chromatography mass spectrometry (LC-MS), high-performance liquid chromatography (HPLC), ELISA, and spectrofluorimetry have been used. Moreover, the biological matrix used for analysis appears to be critical as well, e.g., large variations in protein AGE levels have been reported in collagen calling into question the relevance of skin measurements for diabetic complications.

No general consensus has emerged regarding which specific AGEs might be of optimal value for monitoring glucose control or predicting diabetic complications. Together with the lack of uniform methodology for measurement, this has made it difficult to standardize diagnostic endpoints. For these reasons, protein-AGE determination in the clinical setting has only seen limited use.

Approximately a dozen protein-AGEs have been characterized and liquid chromatography tandem mass spectrometry (LC-MS/MS) methods have been described for their quantitative measurement. Choosing an appropriate protein-AGE biomarker for evaluating the glycation status of a particular target tissue or organ is complicated by unequal protein-AGE distributions across different tissues, varying adduct stabilities, and the limited availability of stable isotope standards for quantification.

In spite of longstanding interest in the role of biopolymer glycation in human disease, no generally applicable method for the quantitative determination of CEdG has been described. A $^{32}$P post-labeling assay has been used to estimate endogenous levels of CEdG in human buccal epithelial cells of 2-3/10$^7$ nucleotides.[28] However, although the post-labeling method offers potential advantages in sensitivity, a major drawback is that direct analyte verification is not possible. Moreover, post-labeling is prone to artifacts and false positives, and may lead to inaccurate estimation of adduct levels due to several factors including RNA contamination.

An immunoaffinity-based method for the detection of CEdG using a polyclonal antibody coupled to a diode array HPLC platform has more recently been described by Schneider et al in 2006. This approach was used to provide the first demonstration of CEdG in human urine and cultured smooth muscle cells. In some cases, peak identity was confirmed by LC-MS/MS, but quantitation was not practical due to the imprecise nature of immunoaffinity chromatography. A monoclonal-based immunohistochemical detection method has also been reported and was used to demonstrate elevated levels of CEdG in aorta and kidney of diabetic patients relative to normal controls.[31] However, antibody-based assays are primarily of value in qualitative and comparative determinations of adduct abundance.

To date, there are no reliable quantitative methods for CEdG measurement, which is likely due to a lack of suitable isotopically enriched standards and other barriers to a reliable quantitative method. Such a method would be a substantial improvement in the art.

SUMMARY

In a first embodiment, AGEs, such as N$^2$-(1-carboxyethyl)-2'-deoxyguanosine (CEdG) may be quantified in a biological sample using liquid chromatography electrospray ionization tandem mass spectrometry (LC-ESI-MS/MS) for diagnosis, monitoring, and treatment of pathologies involving metabolic disorders, including abnormal glucose metabolism. Such pathologies include diabetes and diabetic complications including, but not limited to, microvascular and macrovascular complications—such as hypertension, stroke, cardiovascular diseases, neuropathy, nephropathy, and retinopathy; hyperosmolar hyperglycemic nonketotic syndrome (HHNS); ketoacidosis; foot and skin ulceration and damage, hearing impairment, Alzheimer's disease, as well as certain cancers, amongst other metabolic diseases or disorders. Quantification is achieved by a stable isotope dilution method using an internal standard. When the AGE is CEdG, the internal standard is $^{15}$N$_5$-CEdG. The advantage of having two stereoisomers of CEdG that can be resolved and quantitated is that it allows for two independent measurements for the same condition, significantly enhancing the accuracy of the method.

Detecting physiologically elevated or depressed AGE levels in a sample may indicate that the subject from which the sample was taken has a disease or disorder caused or indicated by such AGE levels. The quantification method allows for a precise determination of AGE amounts and thus, allows for sensitive determination of AGE levels compared to other samples from the same subject at the same time, other samples from the same subject at different time points, or other samples from other subjects, such as a person known not to be affected by a disease. For example, detecting elevated levels of CEdG in a person indicates predisposition to or the presence of hyperglycemia or diabetes. Reaction of double stranded DNA with MG or glucose in vitro produces primarily N$^2$-(1-carboxyethyl)-2'-deoxyguanosine (CEdG) as a diastereomeric mixture (FIG. 1).

The same type of sample may be used to compare between various AGE levels, such as a comparison between AGE levels in a first tissue sample and a second tissue sample. Alternatively, the AGE levels may be compared between various types of samples so long as the relative physiological normal level for each type of sample is known.

In another embodiment, internal standards for other AGEs are created using the methods disclosed herein for synthesizing the internal standard of CEdG. Standards for MS are typically identical in structure to the intended analyte, but contain stable isotopes ($^{15}$N, $^{13}$C, $^{18}$O) in order to give a different mass to an otherwise chemically identical substance. The isotope behaves identically to the intended analyte, has the same retention on chromatography, undergoes the same chemistry, and is only distinguishable by mass.

In a different embodiment, the quantification methods described herein may also be used to determine the effectiveness of a therapy, which may be a test compound or other protocol, intended to treat or ameliorate an AGE-related disease or disorder (a "therapeutically effective amount"). Before the therapy is administered, a first biological sample is taken. After the therapy has been administered, a second biological sample is taken. Additional biological samples may also be taken at other time points during and/or after the therapy. AGEs are quantified in the samples and the difference between AGE levels in the samples is measured. Other known statistical analysis, such as tests for statistical significance, may also be applied. If a successful therapy results in a reduction of the level of AGE and such reduction is noted after the administration of the therapy, it indicates that the therapy may be working for its intended purpose. If AGE levels in the sample are static or increased during the course of the therapy, it indicates that the therapy may not be working for its intended purpose of reducing AGE levels. If a successful therapy results in an increase of AGE levels with a treatment, the opposite analysis would apply: increases in AGE levels would indicate the therapy may be working, whereas static or decreased levels would indicate that the therapy may not be effective.

Kits for quantifying AGE levels, such as CEdG levels, are also contemplated. Such kits facilitate the methods described herein may contain any of the following: standards such as $^{15}$N$_5$-CEdG, tubes, labels, reagents such as buffer, and instructions for use.

Another embodiment involves measuring urine samples in an animal model to monitor the dose dependency of LR-90 as it decreases CEdG levels in vivo.

Yet another embodiment is measuring the effect of aromatase inhibitors on CEdG levels, and relatedly, on glycation status. CEdG levels are measured in a subject undergoing aromatase inhibitory therapy (AI) to determine the impact of AI on cognitive function and mental acuity.

A method of measuring CEdG to predict chemosensitivity of tumors and to identify cancers that may be treated from targeting glyoxalase 1 (Glo1) and/or aldose reductase to restore chemosensitivity is also described. Tumors with elevated levels of CEdG are more sensitive to chemotherapy. Related methods of inducing production of CEdG or other AGE products in tumor cells or of administering CEdG to tumor cells to induce apoptosis and/or increased sensitivity to chemotherapy are also provided. The effectiveness of radiotherapy may also be tested by measuring CEdG in tumors.

Also disclosed are methods of diagnosis, prognosis, or therapy of pathologies involving metabolic disorders such as diabetes and diabetic complications described above. The methods entail measuring the levels of one or more biomarkers such as CEdG in a biological sample from a patient, wherein an elevated level of the one or more biomarkers relative to the level of the biomarker in a control, healthy subject or to a preset threshold value indicating the status of the pathology or an elevated risk of the pathology. The methods of treating the pathology further include treating the patient who has an elevated level of the biomarker with one or more therapies. For example, the methods disclosed herein comprises administering a treatment for diabetes or diabetic complications to the subject who is determined to have the diabetic complication. The methods of prognosis further include treatment monitoring including comparing the levels of the biomarker before and after the treatment. In some embodiments, the pathology is diabetes, a diabetic complication, e.g., nephropathy, or cancer, and the biomarker is CEdG. In some embodiments, the methods disclosed herein comprise, after administering the treatment for diabetes or diabetic complications, determining whether the treatment is therapeutically effective by repeating the step(s) of measuring the levels of one or more biomarkers such as CEdG in a biological sample from a patient, wherein an elevated level of the one or more biomarkers relative to the level of the biomarker in a control, healthy subject or to a preset threshold value indicating the status of the pathology or an elevated risk of the pathology. In certain embodiments, the determination of whether the treatment is therapeutically effective can occur at any time after administration of treatment. Non-limiting examples include, taking a biological sample immediately after treatment, 1 hour after treatment, 2 hours after treatment, or after a regimen of a month, 6 months, or one year.

A suitable treatment can be selected based on the particular diabetic complication. For example, various treatments for diabetic nephropathy are available, including for example, angiotensin-converting enzyme (ACE) inhibitors, such as captopril, enalapril, lisinopril, and ramipril, and angiotensin II receptor blockers (ARBs), such as cancesartan cilexetil, irbesartan, losartan potassium, and telmisartan.

A novel synthesis of oligonucleotides containing site-specifically modified CEdG residues is shown in FIG. 16. Such synthesis facilitates experiments using CEdG, such as experiments that investigate the biological consequences of CEdG substitution in DNA and for serving as internal standards for assays measuring CEdG.

These and other embodiments are further explained by reference to the detailed description.

BRIEF DESCRIPTION OF THE DRAWINGS

FIG. 8A: UV spectra of CEdG(A(R))(solid line) and CEdG(B(S))(dotted line) with no isotopic labeling. Both samples were diluted 1:50; $OD_{255}$(dG)=12,300 OD/M. For CEdG(A(R)), XX-49-A, 28.55 mL; diluted $OD_{255}$=0.450; undiluted $OD_{255}$=22.50; conc.=1.83 mM, 52.22 umol @ FW 338.30=17.67 mg. For CEdG(B(S)), XX-49-A, 40.61 mL; diluted $OD_{255}$=0.327; undiluted $OD_{255}$=16.35; conc.=1.33 mM, 53.98 umol @ FW 338.30=18.26 mg. FIG. 8B: $^{15}N_5$-CEdG(A(R)); 2 μL stock diluted to 500; $OD_{255}$=1.207. FIG. 8C: $^{15}N_5$-CEdG(B(S)); 1 μL stock diluted to 500; $OD_{255}$=0.883.

FIG. 22A. Representative ion chromatogram of (R,S)-CEdG in urine (top panel) and $^{15}N_5$-(R,S)-CEdG isotopic standard (bottom panel). Mass transitions used for identification and quantification indicated in the inset. FIG. 22B. Structure of the DNA-AGE CEdG (m/z 340). Dashed arrow indicates the primary fragmentation giving rise to the mass transitions indicated in FIG. 22A. Asterisk (*) indicates the chiral center.

FIG. 23A. CEdG levels were compared between normoglycemic (n=22; FPG<200 mg/dL) and hyperglycemic (n=11; FPG≥200 mg/dL) mice. Significance was determined using a non-parametric unpaired t-test. FIG. 23B. Mean CEdG levels were plotted for each animal and the median value was determined to be 17 pmol/24 h. FIG. 23C. Mean CEdG values grouped according to genotype, significance calculated as in FIG. 23A.

FIG. 25A. Average CEdG and FPG values for individual animals were determined using repeated measures analysis. Correlations were calculated with Spearman's coefficient (r=0.6621). FIG. 25B. Average CEdG and HbA1c calculated as in A, r=0.8016.

FIGS. 27A-27D. CEdG from tissue is elevated in hyperglycemic and Lepr mutant mice. DNA was isolated from pancreas, liver, colon, and kidney and analyzed for CEdG. CEdG values were averaged across tissues from individual mice and grouped according to glycemic status (FIG. 27A) or genotype (FIG. 27B). FIG. 27C. CEdG measurements from pancreas, liver, colon, and kidney from individual mice stratified by genotype. FIG. 27D. One-way ANOVA with Tukey's modification was used to analyze CEdG differences between genotypes (irrespective of tissue, last column) and between tissue (regardless of genotype, bottom row). †CEdG/$10^6$ dG. Significance values: *p≤0.05; p≤0.01; *p≤0.001; ****p≤0.0001.

FIG. 28A. Mean values of CEL and CML measured in urine from aged-matched hyperglycemic and normoglycemic wt (9), wt/db (9), and db/db (11) mice using LC-ESI-MS/MS. FPG was measured at the cessation of 24 h urine collection. Two-way ANOVA revealed a significant increase in CEL and CML in hyperglycemic mice (**p<0.0001). FIG. 28B. CML (n=32) and CEL (n=32) vs. FPG. No significant correlation was observed. CML, r=0.2458; CEL, r=0.2267. FIG. 28C. Plot of CML and CEL vs. CEdG for all mice; CML, r=0.7009 (p<0.0001); CEL, r=0.4902 (p=0.0044). FIG. 28D. CML (n=32) and CEL (n=32) vs. CEdG from hyperglycemic mice; CML, r=0.5589 (*p=0.0471); CEL, r=0.5805 (*p=0.0375).

DETAILED DESCRIPTION

Figure 1:
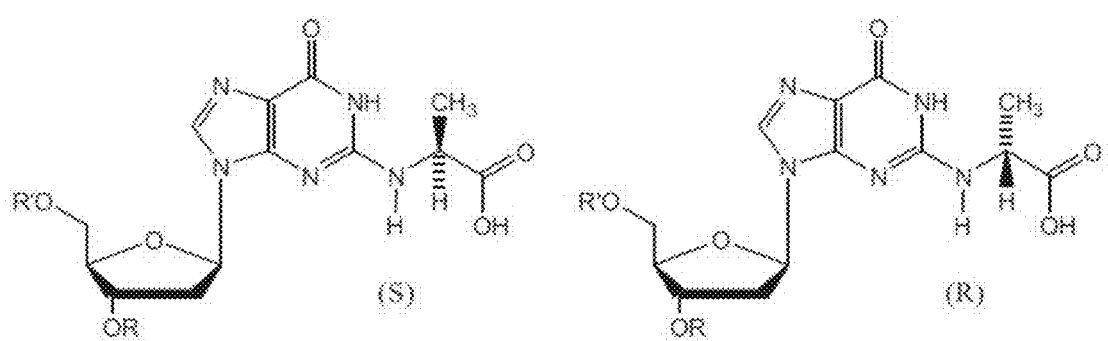
FIG. 1. The two CEdG diastereomers formed from reaction of MG with dG.

Quantitative measurement of AGEs is accomplished using mass spectrometry, such as LC-ESI-MS/MS and internal standards designed for each targeted AGE. Such measurements allow for precise determinations of AGE levels, including small or incremental changes in such levels. Various pathologies involving metabolic disorders such as diabetes and related complications and other diseases may be diagnosed by measuring $N^2$-(1-carboxyethyl)-2'-deoxyguanosine (CEdG) levels alone or in conjunction with other AGEs in biological samples, including but not limited to urine, blood, plasma, serum, tissue (e.g. tumor tissue) samples. The CEdG levels from the biological sample are then compared to physiologically normal CEdG levels. Methods for further determining the efficacy of therapies or treatments applied to these pathologies comprise measuring the effect of the therapeutic has on the CEdG levels in a subject receiving it.

Of the approximately 29 million people with diabetes in the United States, it is estimated that 30% are undiagnosed. Risk for developing diabetes associated complications increases with poor glycemic control. Therefore, identifying diabetic individuals earlier and more accurately remains an unmet clinical need. Delayed clinical intervention for diabetes increases the severity of microvascular complications (e.g., diabetic nephropathy, neuropathy, and retinopathy) and macrovascular complications (e.g., coronary artery disease, peripheral arterial disease, and stroke) as demonstrated by the Diabetes Control and Complications Trial (DCCT) and the subsequent long-term follow up study the Epidemiology of Diabetes Intervention and Complications (EDIC) trial.[69,70] These studies demonstrated that frequent blood glucose measurements and intensive insulin therapy could significantly improve patient outcomes. However, such vigilant biomonitoring and therapeutic intervention is not a practical goal for the majority of patients with diabetes, and the development of improved diagnostic tools to identify patients most likely to benefit from intensive treatment is an ongoing challenge. Because of the inherent difficulties of accurate glucose monitoring, e.g., wide fluctuations in daily plasma levels, glucose instability, and variability in measurement methods and standards, validated long-term biomarkers of glycemic control have come into routine clinical practice. The primary example is hemoglobin A1c (HbA1c), the Amadori adduct of the N-terminal valine of the hemoglobin β-chain. Its measurement has since become the gold standard for the monitoring of glycemic control and more recently as a diagnostic index for diabetes. HbA1c measurement reflects the average glucose over ~120 days, the mean lifetime of the erythrocyte. Although HbA1c levels≥6.5% (48 mmol/mol) significantly correlate with diabetes, over-reliance on HbA1c can lead to misdiagnosis in a significant percentage of the population. For example, the Finnish Diabetes Prevention Study showed that a diagnostic criteria of HbA1c≥6.5% failed to identify ~60% of patients with type 2 diabetes originally identified by two consecutive oral glucose tolerance tests. Although there is a linear relationship between mean blood glucose and HbA1c, ~30% of patients with type 2 diabetes have HbA1c levels above or below values predicted from mean plasma glucose. Such individuals are classified as "high or low glycators" and consistently show these variations over time, suggesting an intrinsic biological origin of this phenomenon. The failure of HbA1c to invariably correlate with glycemic status has been attributed to a variety of factors that may influence HbA1c formation and persistence within erythrocytes. These include undiagnosed hemoglobinopathies, inter-individual variation in glucose transporter (GLUT) activity, erythrocyte turnover, and genetic differences attributed to ethnic background and other unidentified factors. Whatever the origin of the discrepancies between HbA1c measurement and standardized glucose tests, other potential biomarkers of glucose control should be developed to complement existing methods and refine our ability to more accurately diagnose and monitor diabetes.

Novel biomarkers of metabolic diseases should complement existing clinical methodology by increasing diagnostic precision, particularly in patients difficult to identify as diabetic using common tests. The ability to accurately identify and monitor patients likely to become diabetic and to predict specific complications before patients become symptomatic remain significant challenges in diabetes care. For example, while HbA1c is an independent predictor of both mild and severe proliferative retinopathy, cardiovascular disease (CVD) is not clearly associated with HbA1c. Some groups have reported that deviations in measured HbA1c from values predicted from FPG can predict increased risk for retinopathy and nephropathy, while analogous models based on fructosamine measurement were reported to provide a more accurate algorithm for the prediction of nephropathy. In general, efforts to find improved diabetic biomarkers have often focused on glycation and protein AGEs rather than nucleic acid AGEs.

Potential candidates for biomarkers of glycemia are DNA AGEs. The stability of DNA, its uniform cellular distribution, and its substantially longer lifetime relative to proteins suggests that DNA-AGE measurement could provide a more long-term assessment of glycemic control. In contrast to the multiplicity of amino acid AGEs described in humans, there are only two DNA-AGEs detectable in blood and urine; CEdG and a cyclic diol arising from direct addition of MG at $N^1$, $N^2$ of guanine (cMG-dG). In contrast to CEdG, whose stability in DNA and as a deoxynucleoside is comparable to 2'-deoxyguanosine, cMG-dG is significantly less stable and less suitable as a potential biomarker.

Methods to detect DNA AGEs include $^{32}P$ post-labeling, polyclonal antibody-based analysis, and LC-ESI-MS/MS. Of these methods, LC-ESI-MS/MS coupled with stable isotope dilution provides the most accurate quantification of CEdG. Using this approach, the first measurement of CEdG in a high-dose streptozotocin (STZ) rat model of type 1 diabetes demonstrated increased levels relative to normoglycemic controls. To further elucidate the physiological relevance of DNA-AGEs in type 2 models of diabetes, described herein are measurements of CEdG in $Lepr^{wt/wt}$ (wt), $Lepr^{wt/db}$ (wt/db), and $Lepr^{db/db}$ (db/db) mice, which provided a range of FPG from 70 to 978 mg/dL and HbA1c levels from 3-15% (9 to 140 mmol/mol). Mice with a $Lepr^{db}$ gene have an alternatively spliced variant of the leptin receptor, which is highly expressed in the hypothalamus and is resistant to the effects of the leptin hormone. This leads to the development of obesity, hyperglycemia, hyperlipidemia and other metabolic abnormalities within a few weeks of birth, which mimic the pathology found in type 2 diabetes. Heterozygous mice (wt/db) typically do not exhibit a gross diabetic phenotype; however, they exhibit several distinguishing metabolic traits relative to wt animals including a decreased rate of glucose oxidation and slower rates of catabolism.

CEdG levels are measured using LC-ESI-MS/MS or other reliable means. CEdG levels from the sample are then compared to the levels in physiologically normal subjects. Methods for further determining the efficacy of therapies or treatments applied to various disorders comprise measuring the effect the therapeutic has on the CEdG levels in a subject receiving it. The subject having its AGE levels and/or the efficacy of treatment measured is preferably a mammal, such as a human.

Thus, one method of quantifying one or more advanced glycation end products in a sample, comprises obtaining a biological sample from a subject; and performing LC-ESI-MS/MS assay on the sample using stable isotope dilution with an internal standard to determine AGE levels within a sample. When the AGE is CEdG, the internal standard is $^{15}N_5$-CEdG. With CEdG quantities in hand, abnormal levels may indicate metabolic disorders or complications associated with these disorders such as diabetes and cancers. Upon detecting the levels, efficacies of various treatments may be determined using AGE levels as a marker for the success of the treatment.

Figure 23A:
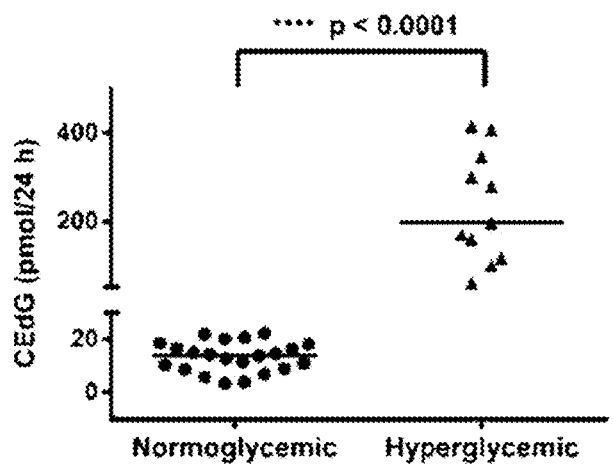
FIGS. 23A-23C. CEdG is elevated as a result of hyperglycemia. CEdG was quantified as described above and time-averaged values (repeated measures analysis) were calculated for each individual animal.

As shown in the working examples, CEdG excreted in the urine of wt, wt/db and db/db mice was measured over a period of 36 weeks and recorded contemporaneously with FPG and HbA1c. CEdG were significantly elevated in hyperglycemic compared to normoglycemic mice (FIG. 23A). Results revealed a positive correlation of urinary CEdG with FPG and HbA1c (FIG. 25). CEdG also positively correlated with the protein AGEs carboxymethyl and carboxyethyl lysine (CML and CEL, respectively) (FIG. 28). These data provide a rationale for applying CEdG measurement as a clinical tool for the diagnosis and management of metabolic diseases.

DNA-AGEs likely enter circulation via DNA repair and/or degradation during cell turnover. CEdG remaining in genomic DNA poses significant hazards since it contributes to genomic instability, which may substantially increase the risk for certain cancers. This is particularly true of diabetic individuals as they have been reported to be compromised in DNA repair. The CEdG levels were examined in a subset of organs at risk for increased cancer incidence in metabolic disease, including pancreas, kidney, colon and liver; and the first measurement of DNA-AGEs in tissue from animal models of diabetes is described herein. This analysis revealed a significantly higher level of CEdG in organs isolated from hyperglycemic mice compared to normoglycemic controls (FIG. 27).

Figure 24:
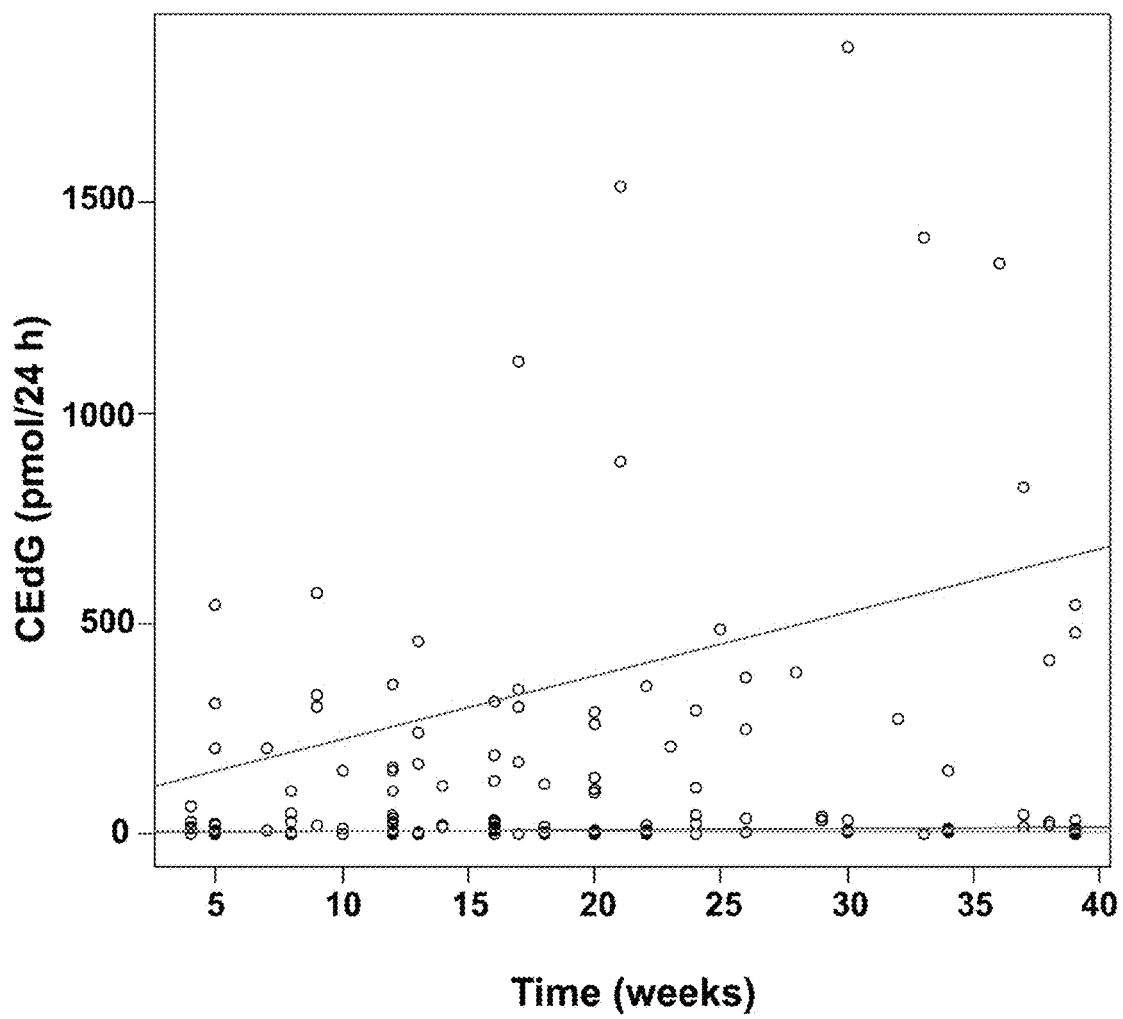
FIG. 24. CEdG significantly increases over time in db/db mice. Individual CEdG measurements were plotted against the age of the mice at the time of collection. To determine differences over time between groups and individual animals, a linear mixed mode analysis was performed (see Table 5). This revealed a significant variation (p=0.0023) over time within the db/db animal population (red line), but not in the wt/db (green line) or wt (blue line) animals. Significant differences among animals within the db/db group were also observed.
Figure 25A:
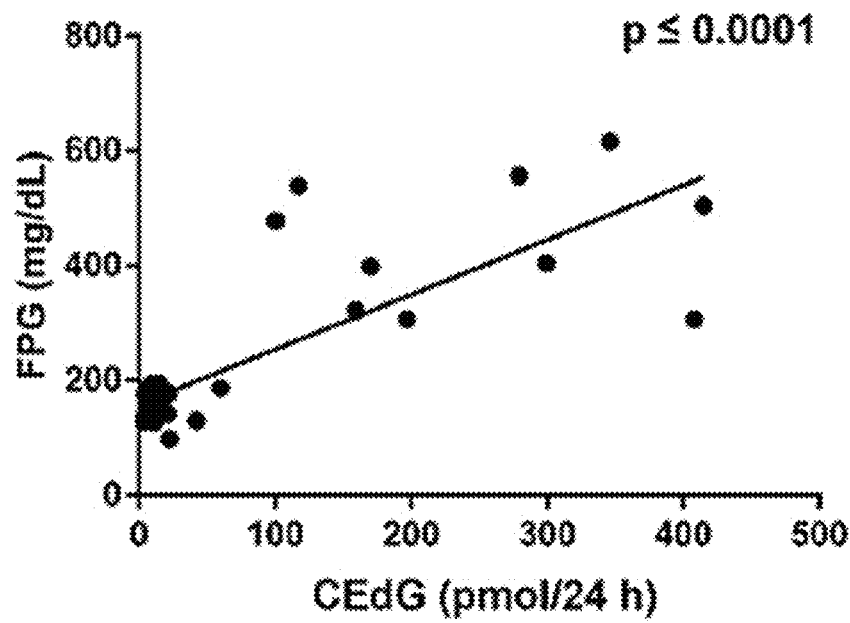
FIGS. 25A-25B. Correlation of CEdG with FPG and HbA1c.
Figure 25B:
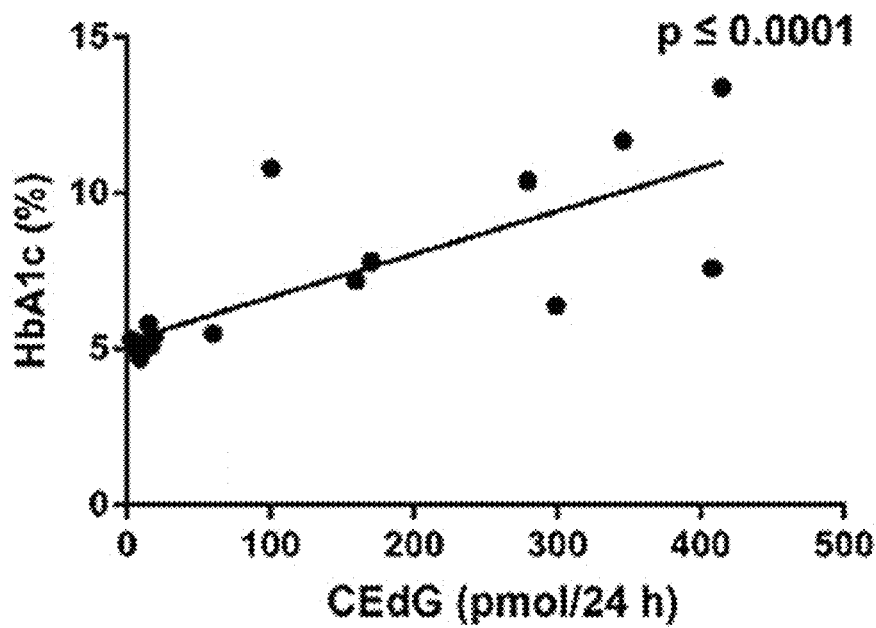

As disclosed herein, since all nucleated cells contain DNA, and DNA has a longer lifetime than protein, measurement of the DNA-AGE CEdG may allow for more precise assessment of long term glycemic stress. The working examples demonstrate that a significant (17-fold) increase in the median value of urinary CEdG in animals with FPG≥200 mg/dL relative to normoglycemic controls. Moreover, consideration of CEdG values alone allowed for a prediction of hyperglycemia with >95% confidence. These observations are consistent with the data using a high dose STZ diabetic rat model, which demonstrated elevated CEdG levels in urine relative to non-diabetic animals. Significant increases in CEdG for both type 1 and 2 diabetic models suggest the direct influence of hyperglycemia on DNA-AGE formation, supported by the linear relationship of CEdG and FPG (FIG. 25A). In contrast to the narrow range of CEdG values observed for normoglycemic mice, values for the hyperglycemic animals were widely dispersed (FIG. 23A). This suggests that stratification of CEdG values may provide diagnostic information relevant to diabetes-related pathologies. For example, individuals in the highest quartile may be at the greatest risk for microvascular and macrovascular complications or cancers associated with metabolic disease. The highest quartile is predicted to be 60-80 nmol/24 hr. The second highest quartile 40 to 60 nmol/24 hr, the third highest quartile 20 to 40 nmol/24 hr and the lowest quartile 1 to 20 nmol/24 hr. This possibility will be more properly addressed in a clinical trial. The large increase in CEdG levels observed for the db/db group over time is striking. The age of the animal alone did not appear to make a substantial contribution, since increases in CEdG over time were insignificant in wt or wt/db mice (FIG. 24). This would suggest that increasing MG generation due to progressive diabetic pathology was the main contributing factor.

Quantification of CEdG in tissue DNA revealed differences between wt and wt/db mice not apparent using the standard FPG or HbA1c markers. Organ data revealed a clear increase in CEdG between wt and wt/db mice when aggregate tissue CEdG measurements were considered (p<0.01, FIG. 27D), even though wt/db animals had FPG, HbA1c, and urinary CEdG values that were indistinguishable from wt (Table 4). The disparity between the CEdG in urine vs tissue may reflect differences between circulating levels of CEdG resulting from DNA repair and/or cell turnover vs local tissue accumulation. The wt/db mice may be considered to exhibit borderline metabolic disease, as they have been shown to have higher rates of glucose oxidation, slower rates of catabolism, and are significantly more prone to gestational diabetes relative to wt animals. The data suggest that MG-induced AGE accumulation can occur in tissue even with a relatively mild diabetic phenotype and contribute to DNA damage despite FPG and HbA1c levels within the normal range. Since it was not practical to assay tissue DNA from all organs, the subset sampled was chosen on the basis of data indicating increased diabetes-associated cancer susceptibility. This tissue sampling bias may have highlighted differences not apparent in the analysis of CEdG in urine. Genetic and epigenetic dysregulation due to the presence of long-lived CEdG modification of DNA may contribute to genomic instability and/or play a role in the phenomenon of metabolic memory in diabetes.

As demonstrated in the working examples, the DNA-AGEs CEdG and the protein AGEs CML and CEL were linearly correlated in the animal model (FIG. 28C), but only CEdG bore a significant relationship to FPG (FIG. 25A vs. 28B). This suggests that measurement of protein and DNA-AGEs may bear different relationships to clinical endpoints of metabolic disease. In summary, the stable DNA-AGE CEdG was significantly elevated in mouse models of diabetes, was able to predict diabetes as a single parameter, correlated with FPG and HbA1c, and was substantially increased in organs of wt/db and db/db mice relative to wt. These observations have catalyzed longitudinal clinical trials to examine CEdG as a biomarker for metabolic disease.

The term "diabetic complications," "diabetic related pathologies" or the like refers to various conditions that can arise from or are linked to metabolic disorders or diseases associated with abnormal glucose regulation caused by diabetes. Metabolic disorders and diseases cover a wide range of disorders involving abnormal metabolic processing, including those related to carbohydrate metabolism, amino acid metabolism, organic acid metabolism, mitochondrial metabolism, porphyrin metabolism, fatty acid oxidation disorders, purine and pyrimidine metabolism, steroid metabolism, mitochondrial metabolism, peroxisomal and lysosomal storage disorders, and glycolytic metabolic disorders.

Many types of clinical complications or pathologies can manifest themselves as a result of diabetes and diabetes-related metabolic disorders and diseases. These diabetic complications include microvascular and macrovascular complications—such as hypertension, stroke, cardiovascular diseases, neuropathy, nephropathy, and retinopathy; hyperosmolar hyperglycemic nonketotic syndrome (HHNS); ketoacidosis; foot and skin ulceration and damage, hearing impairment, Alzheimer's disease, as well as certain cancers. Cancers that are associated with diabetes and diabetes-related metabolic disorders and diseases are sometimes referred to as glycolytic cancers. A glycolytic cancer is a cancer that is caused or influenced by abnormal sugar processing, such as with glycation. Conditions which result in the impairment of glucose regulation such as diabetes and metabolic syndrome have been shown to significantly increase the risk for cancers of the breast, liver, kidney, lung, pancreas, colon, cervix and endometrium.

In the case of hyperglycemia and/or diabetes, an elevated level of CEdG, as compared to normal physiological levels of CEdG, indicates that the subject has diabetes. A sensitive LC-ESI-MS/MS method for the measurement of CEdG in urine or double-stranded DNA is used. Quantification is achieved by the stable isotope dilution method using synthetic $^{15}N_5$-CEdG as an internal standard. Urinary CEdG was measured in normal and streptozoticin-induced diabetic rats, and it was shown that adduct levels are significantly increased following the onset of hyperglycemia. LC-ESI-MS/MS was used to demonstrate a dose-dependent reduction in CEdG in response to administration of LR-90, an inhibitor of AGE formation. Measurement of CEdG from hydrolyzed and dephosphorylated double-stranded DNA was complicated by the fact that MG was present during the enzymatic workup. This was found to react with DNA during sample workup leading to artifactual overestimation of CEdG levels. In order to circumvent this problem, adventitious MG was sequestered by the addition of carbonyl scavengers such as aminoguanidine (AG) and D-penicillamine (D-P) prior to workup, resulting in stable and reproducible determinations. In the case of glycolytic cancers, such as breast cancer, a reduced level of CEdG, as compared to normal physiological levels of CEdG, indicates that the subject has cancer.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Materials and Instrumentation.

$^{15}N_5$-2'-deoxyguanosine was purchased from Silantes (Munich, Germany, lot #dG-N-0507-1/2); DL-glyceraldehyde (95%), calf thymus DNA was from Sigma (St. Louis, Mo.), and ammonium acetate (1M, pH 7 solution) from Fluka (Buchs, Switzerland). Phosphate salts were A.C.S. reagent grade from J. T. Baker (Phillipsburg, N.J.). HPLC grade $CH_3CN$ was purchased from Fisher Scientific (Fair Lawn, N.J.). All water was purified to a resistivity of 18.2 MΩ using a Nanopure Diamond system by Barnstead International (Dubuque, Iowa). Solid phase extractions were performed using 1 ml strata-X-C cation mixed mode cartridges (Phenomenex, Torrance Calif.). Nuclease P1 was purchased from US Biologicals (Swampscott, Mass.). Phosphodiesterase II from bovine spleen and alkaline phosphatase from bovine intestinal mucosa was purchased from Sigma-Aldrich. HPLC separations were performed using a Hewlett-Packard Series 1100 Liquid Chromatography system equipped with a diode-array detector. Ultraviolet spectra were collected on an Ultrospec 3000 pro (Amersham Biosciences, Piscataway, N.J.). Mass analysis of synthetic $^{15}N_5$-CEdG was performed using a Thermo Finnigan LTQ-FT linear ion trap mass spectrometer (San Jose, Calif.) in the Mass Spectrometry-Proteomics Core Facility of the City of Hope.

LC-MS/MS analyses of CEdG in biological samples were carried out using a Micromass Quattro Ultima Triple Quadrupole Mass Spectrometer (Beverly, Mass.) interfaced to an Agilent 1100 Capillary HPLC system (Palo Alto, Calif.) equipped with a Synergi $C_{18}$ analytical column (4μ, 150×2.0 mm; Phenomenex, Torrance, Calif.). $^1H$ NMR spectra were recorded at 400 MHz on a VNMRS spectrometer (Varian, Inc., Palo Alto, Calif.) in the Synthesis and Biopolymer Core Facility of the City of Hope. 1D and 2D NMR data was processed using the Spinworks shareware program (version 2.5.5), copyright 1999-2006 by Kirk Marat and available from the University of Manitoba website.

Synthesis and Characterization of $^{15}N_5$-CEdG.

Figure 2:
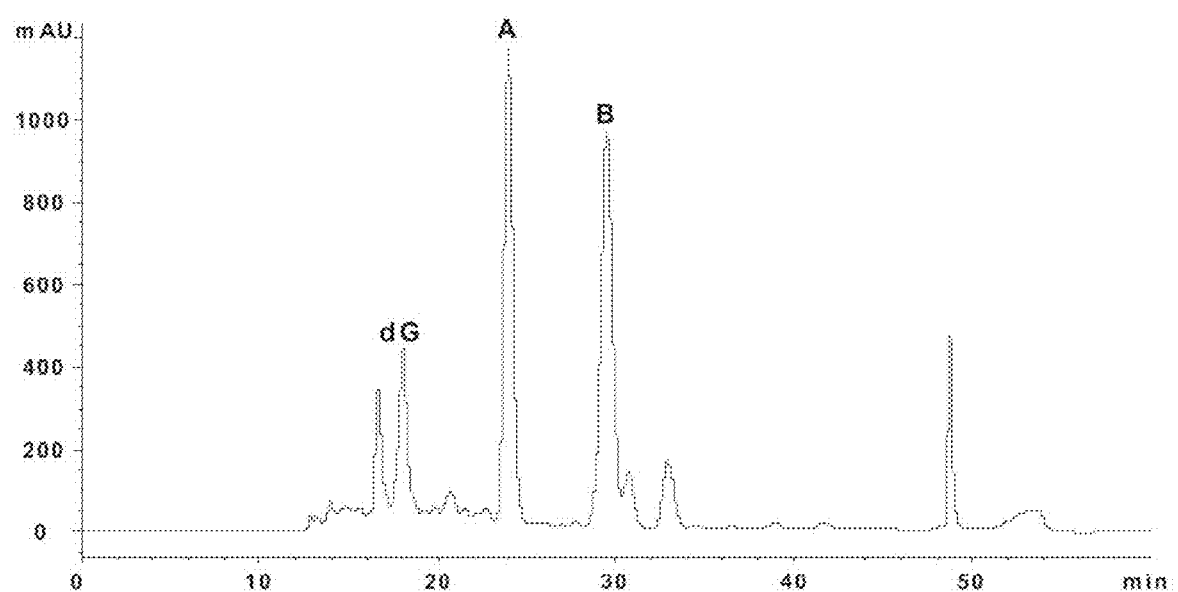
FIG. 2. A representative HPLC chromatogram of the reaction of $^{15}N_5$-dG with DL-glyceraldehyde. Peaks A and B correspond to the two diastereomers of $^{15}N_5$-CEdG (R- and S-CEdG, respectively).

DL-Glyceraldehyde was used to generate methylgloxal (MG) in situ via guanine catalyzed dehydration.[17] DL-Glyceraldehyde (9.5 mg) was added to 10 mg of $^{15}N_5$-labeled dG, 12.3 mg potassium dihydrogen phosphate, and 24.0 mg disodium hydrogen phosphate in 87.7 μL $H_2O$. The heterogeneous reaction mixture was vortexed and placed in a heat block at 40° C. Reactions were worked up following complete dissolution of solids (~14-17 days) yielding a yellow-red viscous solution. Products were purified by HPLC in 10-15 μL aliquots on a 10×50 mm Waters XTerra MS $C_{18}$ 2.5μ column using a $(Et)_3NH_4OAc$ (50 mM, pH 7)/$CH_3CN$ gradient. The $CH_3CN$ concentration was raised from 0 to 4.0% in the first 5 minutes, from 4.0 to 6.5% over 30 minutes; held at 6.5% for 5 minutes, then raised to 90% to wash residual material off the column. Diastereomers CEdG-A and B eluted at 24 and 29 minutes, respectively (FIG. 2).

Figure 3:
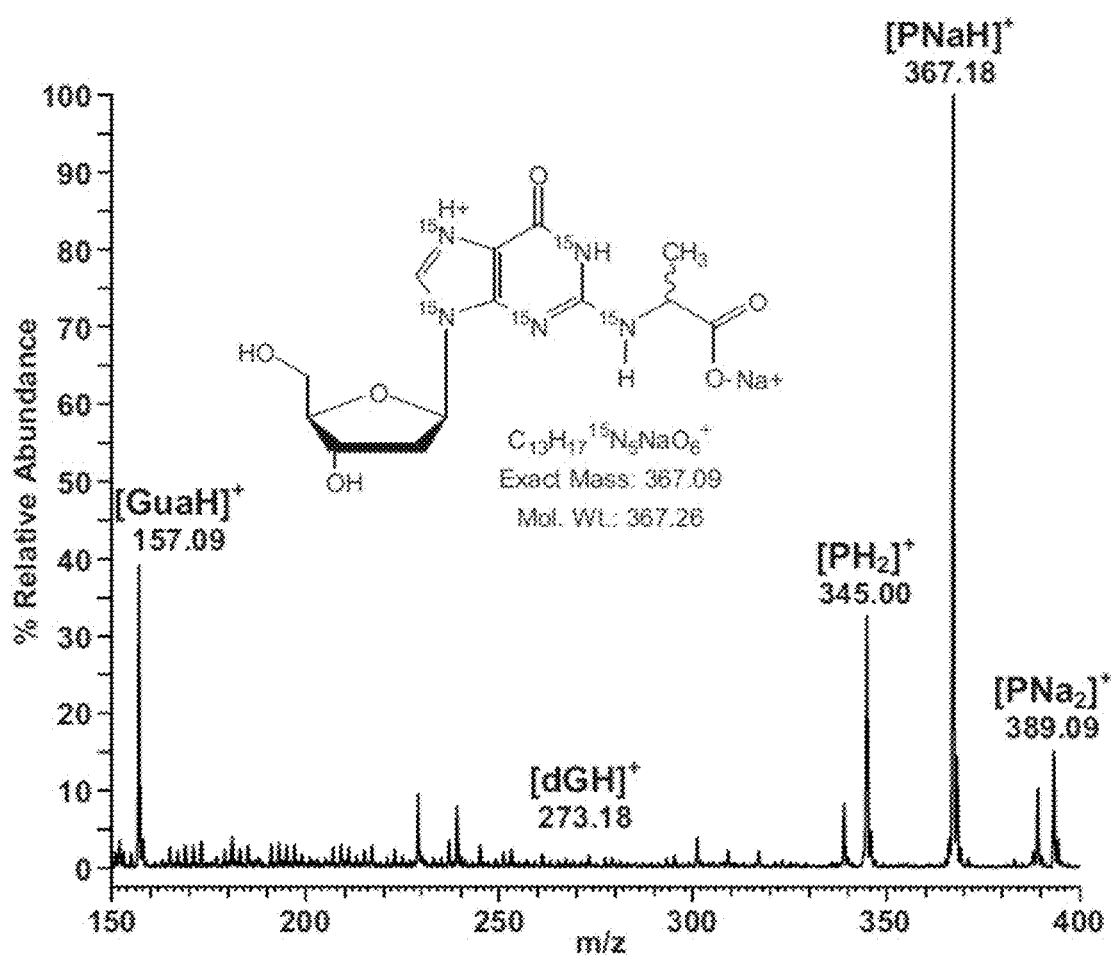
FIG. 3. Full scan positive ion ESI-MS spectrum for $^{15}N_5$-CEdG diastereomer peak A.
Figure 8A:
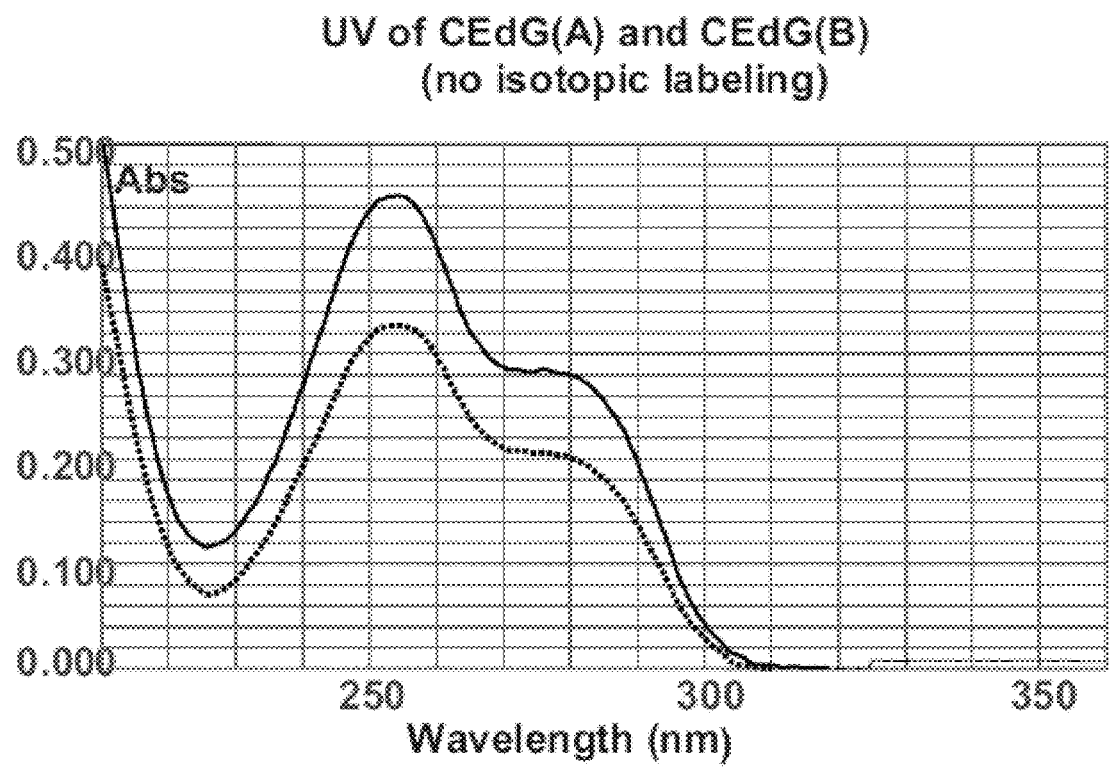
FIGS. 8A-8C. UV spectra of stock solutions of unlabeled (FIG. 8A) and isotopically labeled CEdG diastereomers (FIGS. 8B-8C).
Figure 8B:
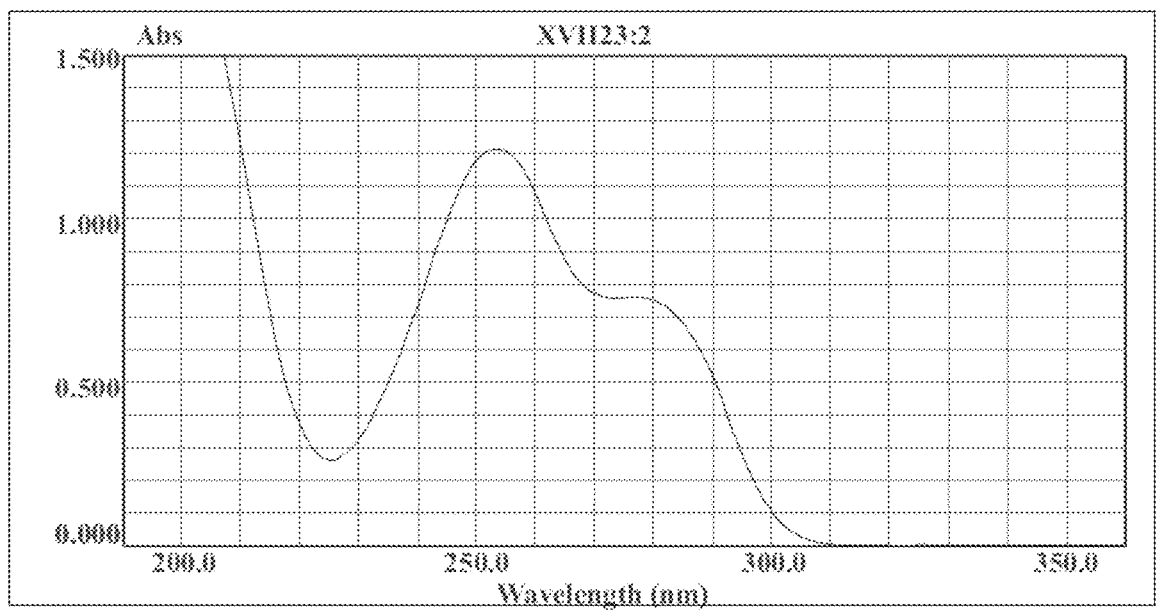
Figure 8C:
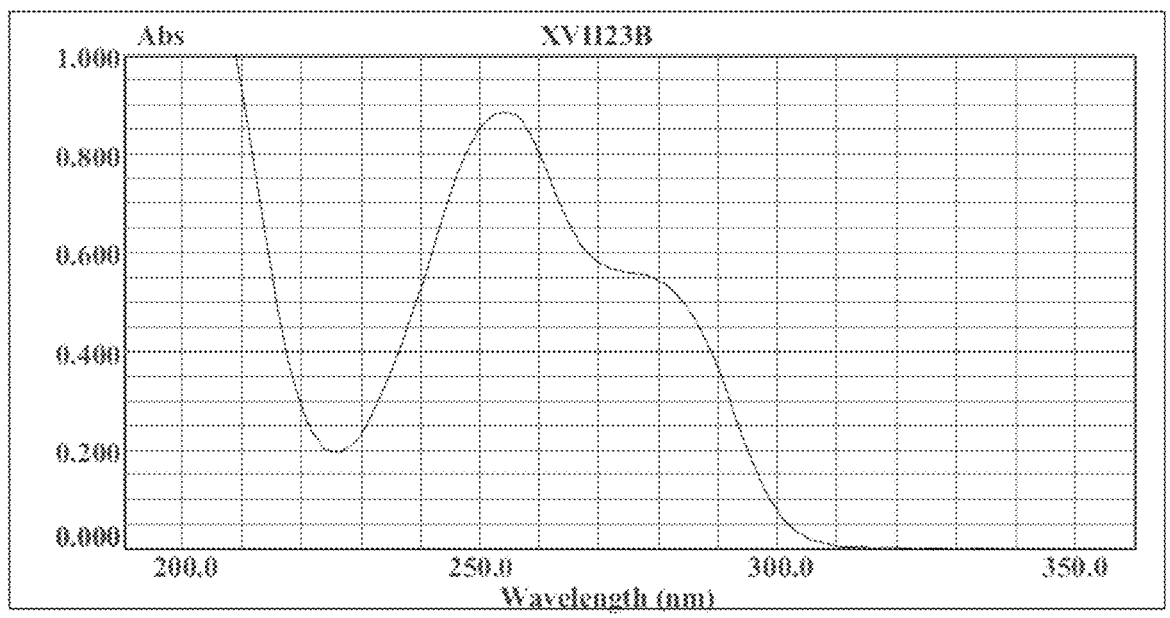
Figure 9:
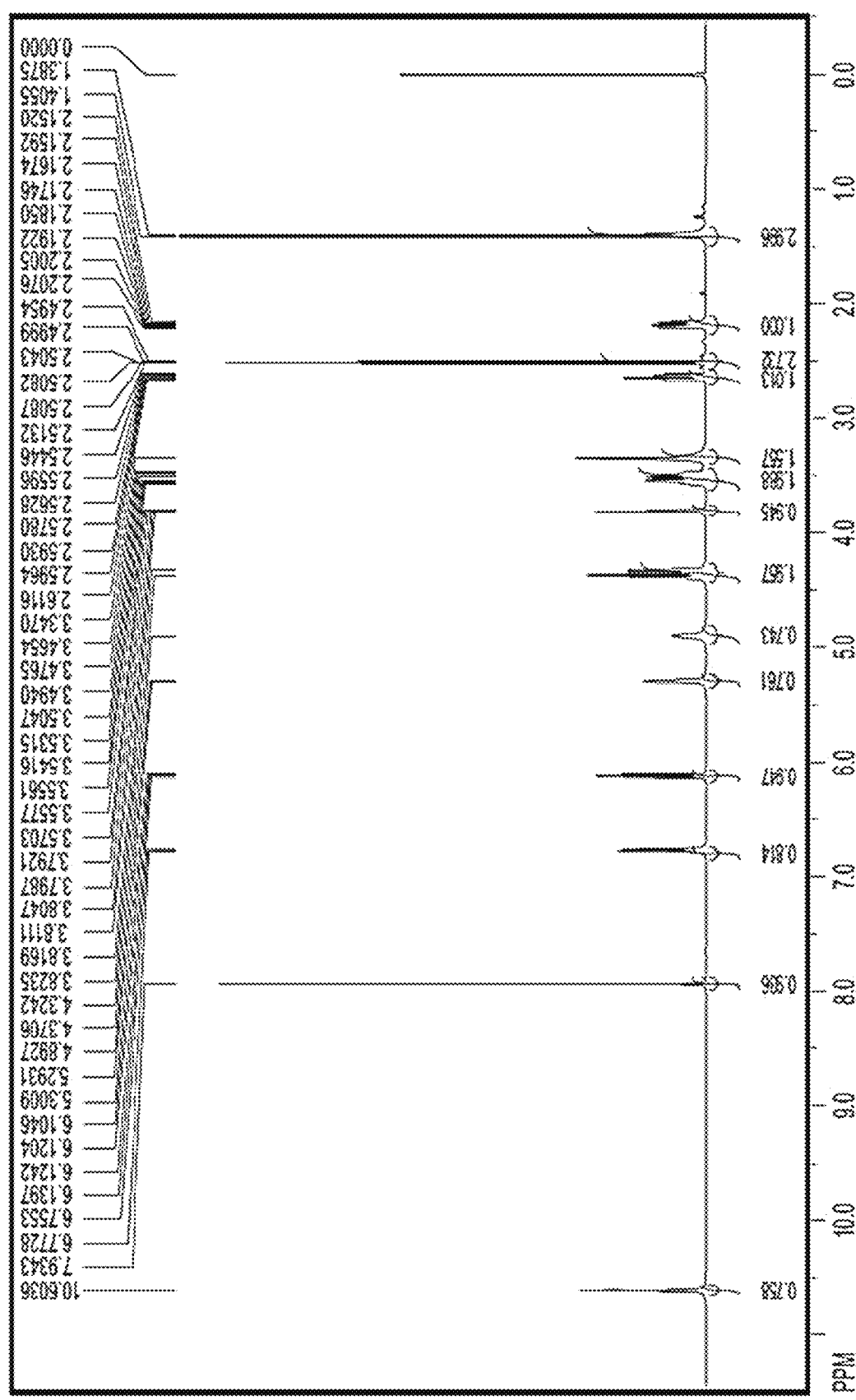
FIG. 9. Proton ($^1H$) NMR of CEdG(A(R)) isomer. The following parameters apply to the spectrum: transmitter freq: 399.806855 MHz; time domain size: 21340 points; width 5208.33 Hz=13.027115 ppm=0.244064 Hz/pt; number of scans: 512; freq. of 0 ppm: 399.804642 MHz; processed size: 65536 complex points; LB: 0.00; GB: 0.00.
Figure 10:
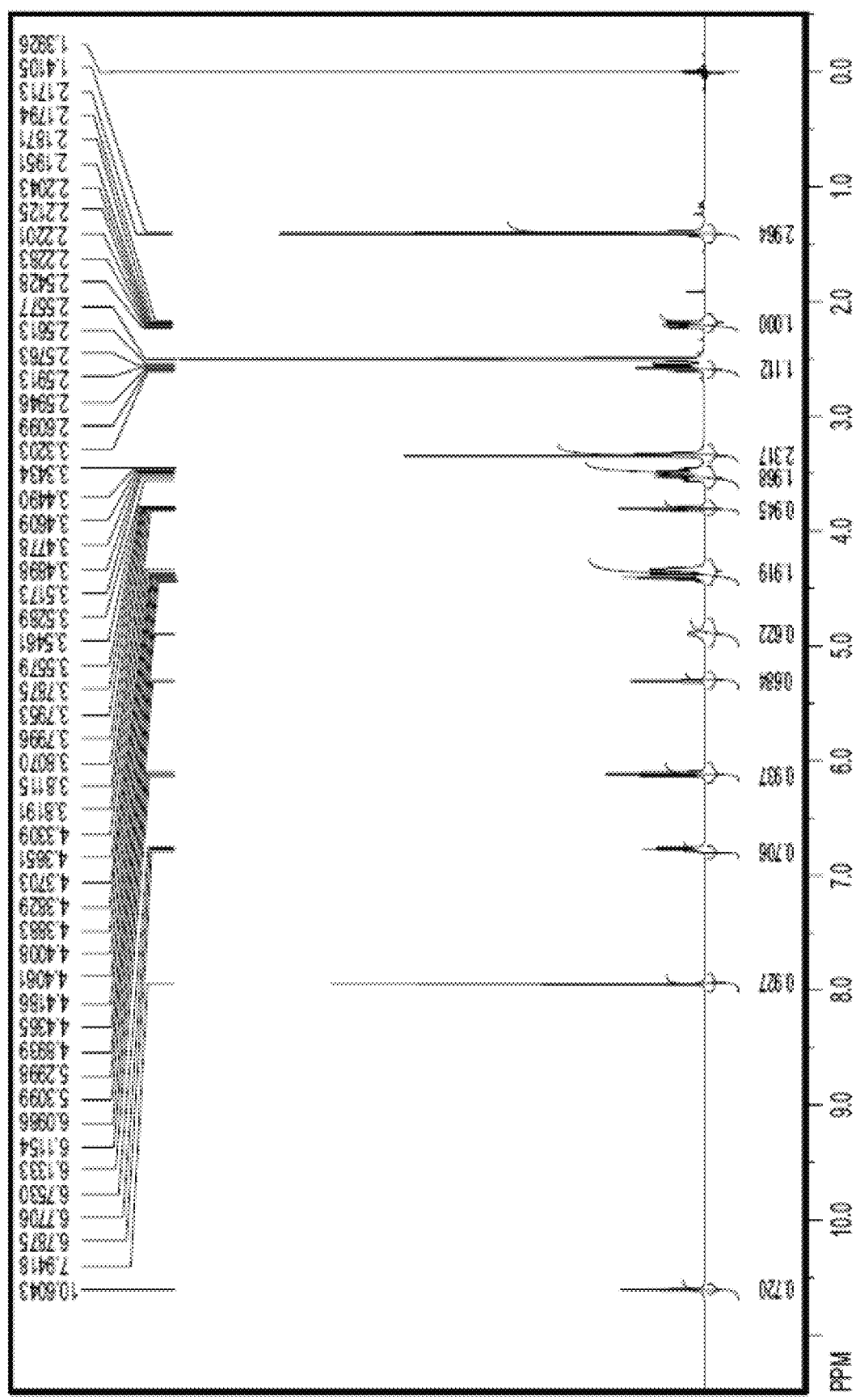
FIG. 10. Proton ($^1H$)NMR of CEdG(B(S)) isomer. The following parameters apply to the spectrum: transmitter freq: 399.806855 MHz; time domain size: 21340 points; width 5208.33 Hz=13.027115 ppm=0.244064 Hz/pt; number of scans: 512; freq. of 0 ppm: 399.804643 MHz; processed size: 65536 complex points; LB: 0.500; GB: 0.00.
Figure 11:
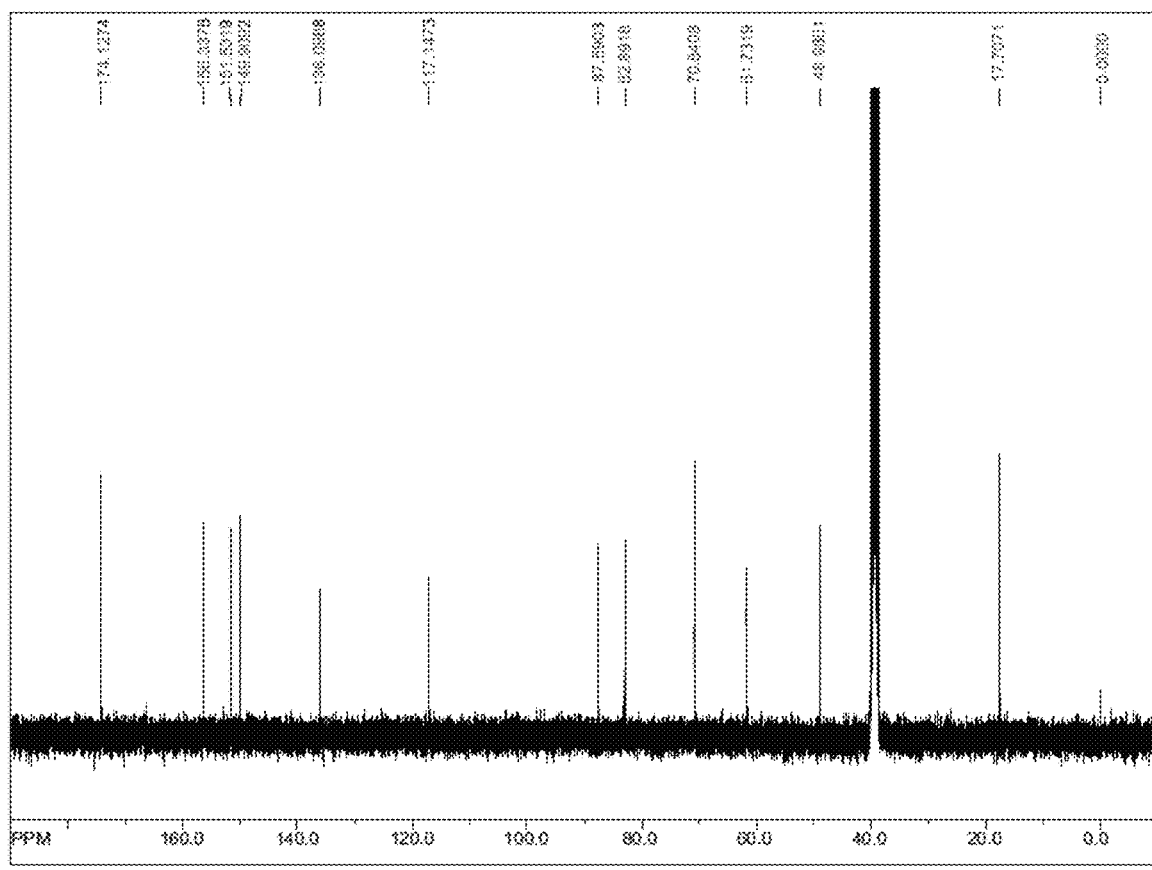
FIG. 11. Carbon data: $^{13}C$ NMR of CEdG(A(R)). The following parameters apply to the spectrum: transmitter freq: 100.541493 MHz; time domain size: 63750 points; width 24509.80 Hz=243.778000 ppm=0.384468 Hz/pt; number of scans: 12000; freq. of 0 ppm: 100.531015 MHz; processed size: 65536 complex points; LB: 0.00; GB: 0.00.
Figure 12:
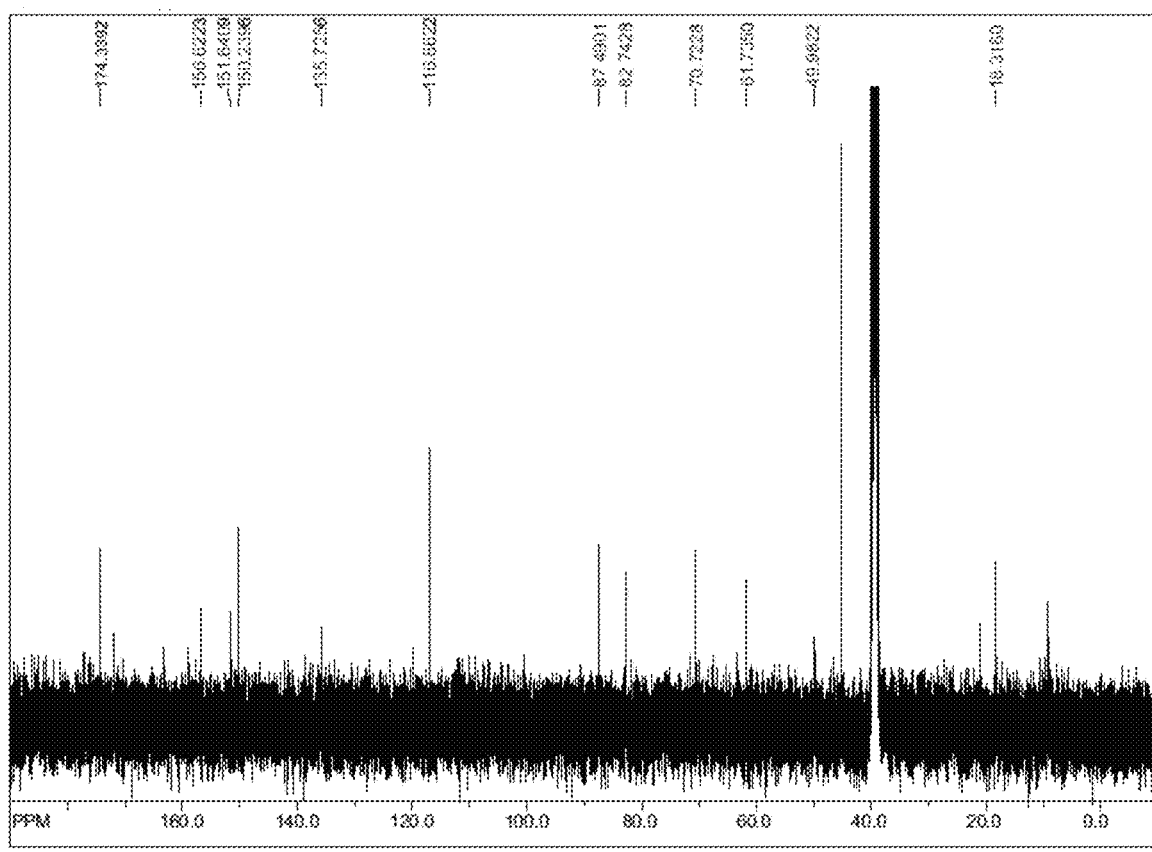
FIG. 12. Carbon data: $^{13}C$ NMR of CEdG(B(S)). The following parameters apply to the spectrum: transmitter freq: 100.541493 MHz; time domain size: 63750 points; width 24509.80 Hz=243.778000 ppm=0.384468 Hz/pt; number of scans: 27000; freq. of 0 ppm: 100.531015 MHz; processed size: 65536 complex points; LB: 0.500; GB: 0.00.
Figure 13:
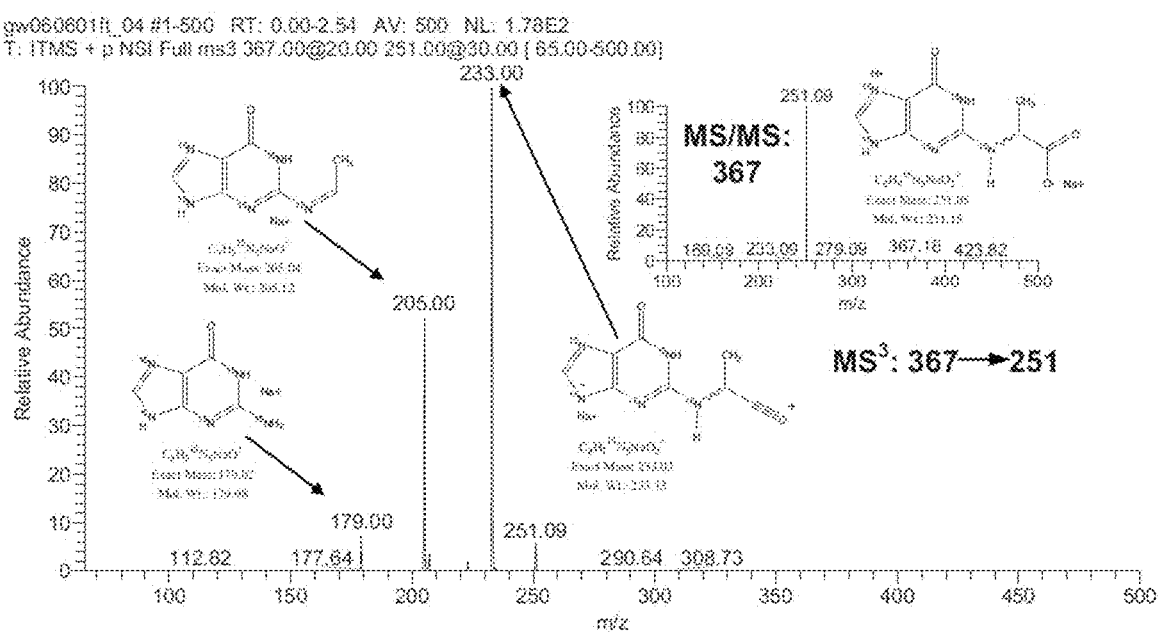
FIG. 13. $MS^2$ and $MS^3$ of sodiated CEdG(A(R)) parent ion obtained using the Thermo Finnigan LTQ-FT linear ion trap mass spectrometer, showing the expected molecular fragments for the isotopically enriched standards.
Figure 14A:
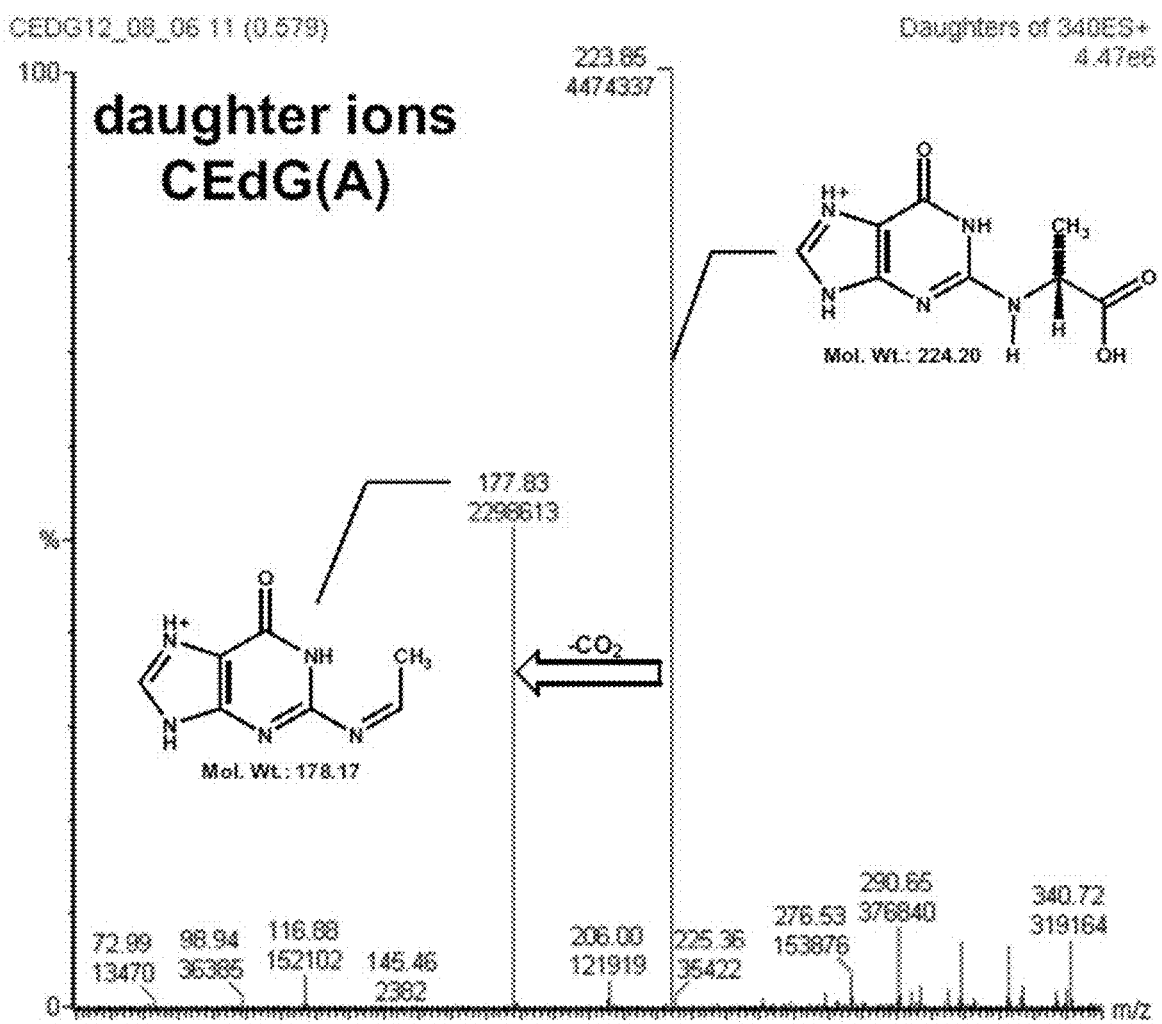
FIGS. 14A and 14B. Product ion scans for CEdG(A(R)) (FIG. 14A) and $^{15}N_5$-CEdG(A(R)) (FIG. 14B) at m/z 340 and 345, respectively, showing the daughter ions at m/z 224 and 229 monitored using a Micromass Quattro Ultima Triple Quadrupole Mass Spectrometer, showing the expected molecular fragments for the isotopically enriched standards.
Figure 14B:
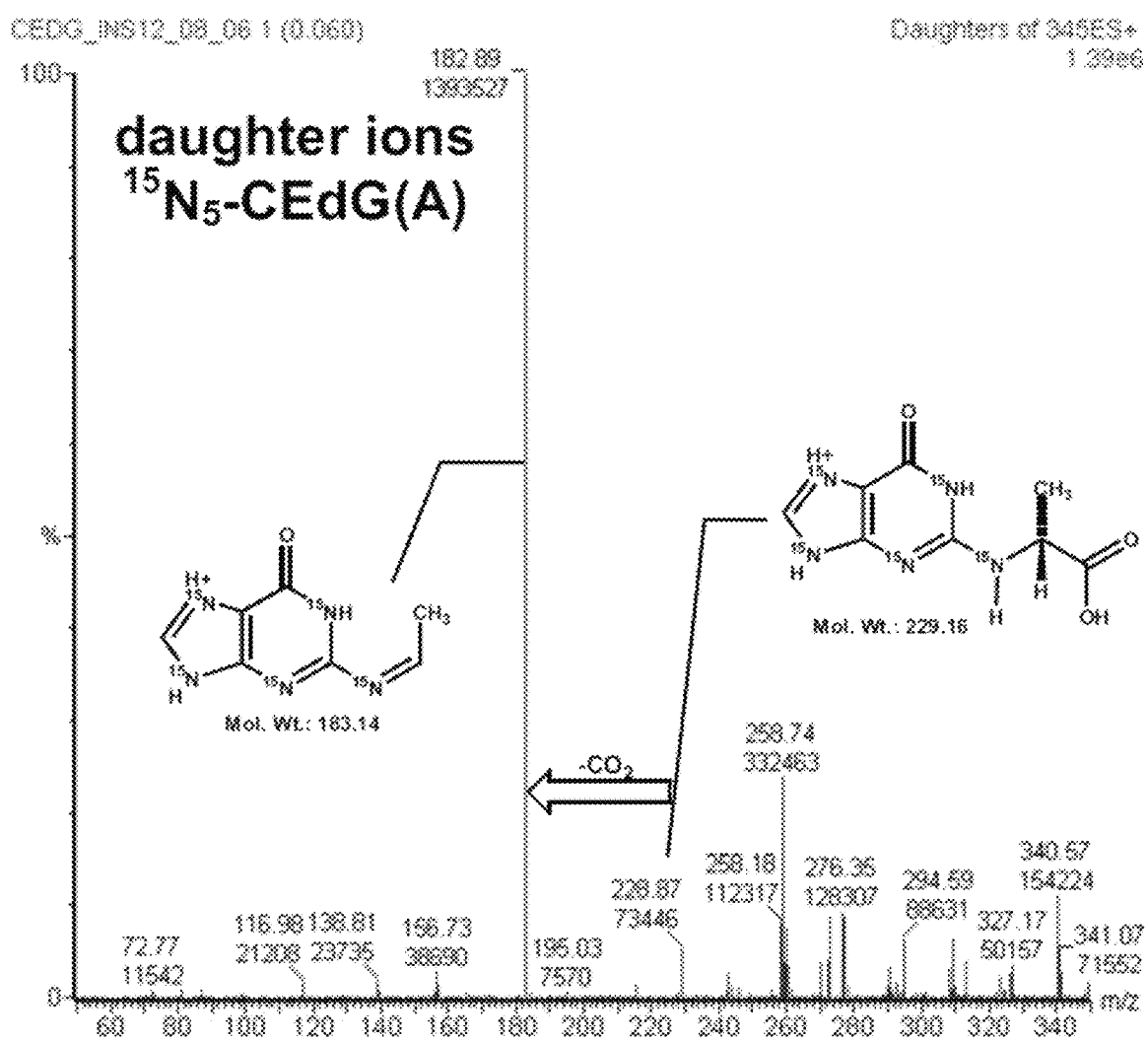
Figure 15A:
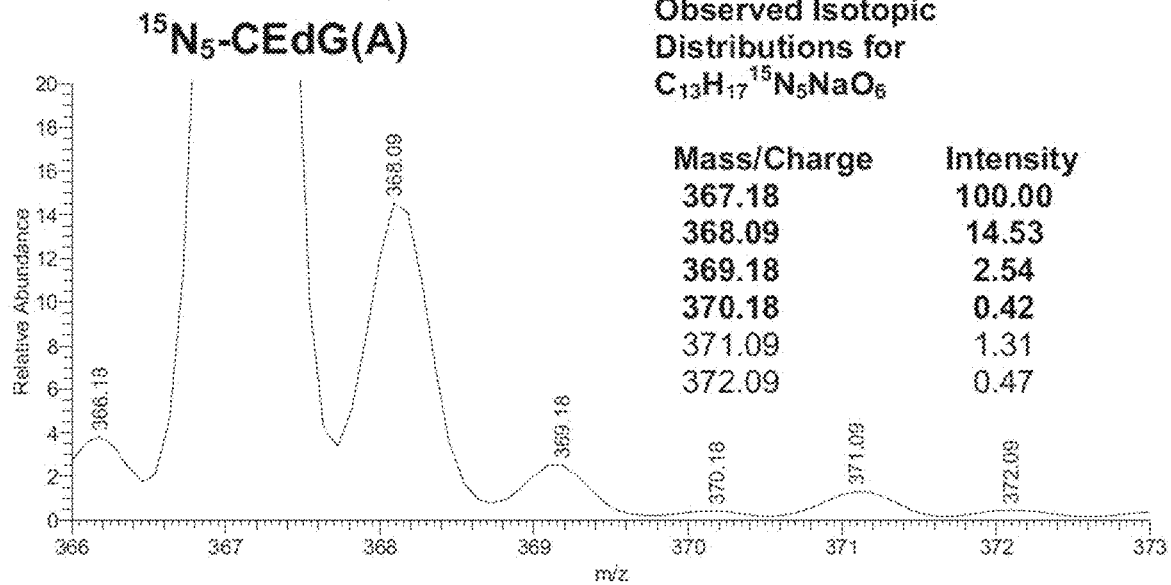
FIGS. 15A-15C. Observed isotopic distributions for $^{15}N_5$-CEdG(A(R)) (FIG. 15A) and $^{15}N_5$-CEdG(B(S)) and the calculated isotopic distribution for $C_{13}H_{17}^{15}N_5NaO_6$ (FIG. 15B) The latter was calculated using the Molecular Weight Calculator, V. 6.38 (FIG. 15C).
Figure 15B:
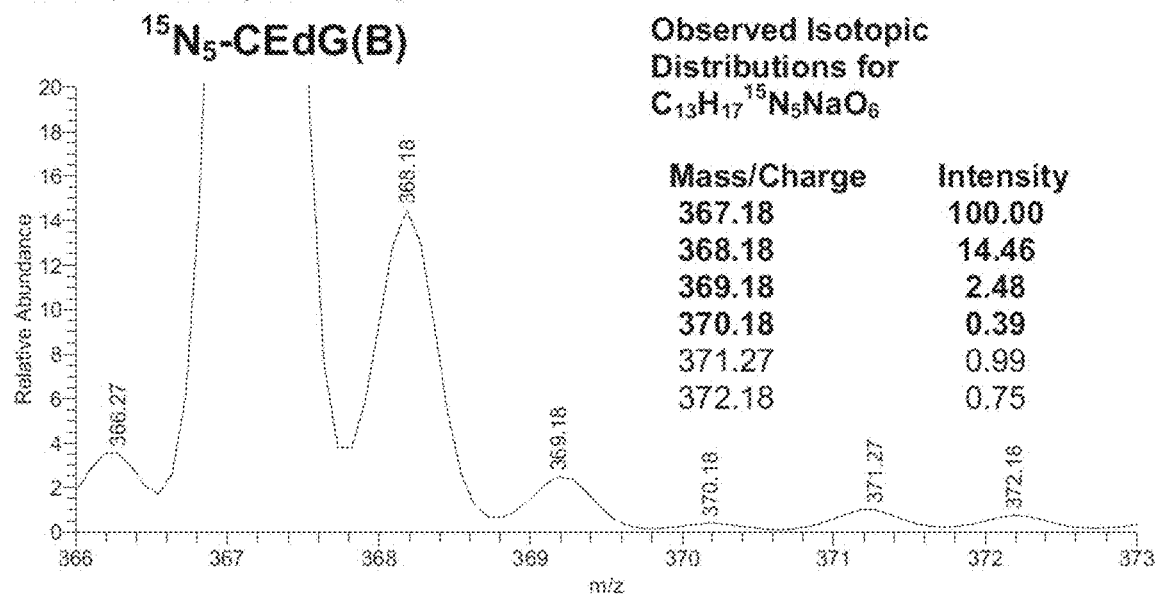
Figure 15C:
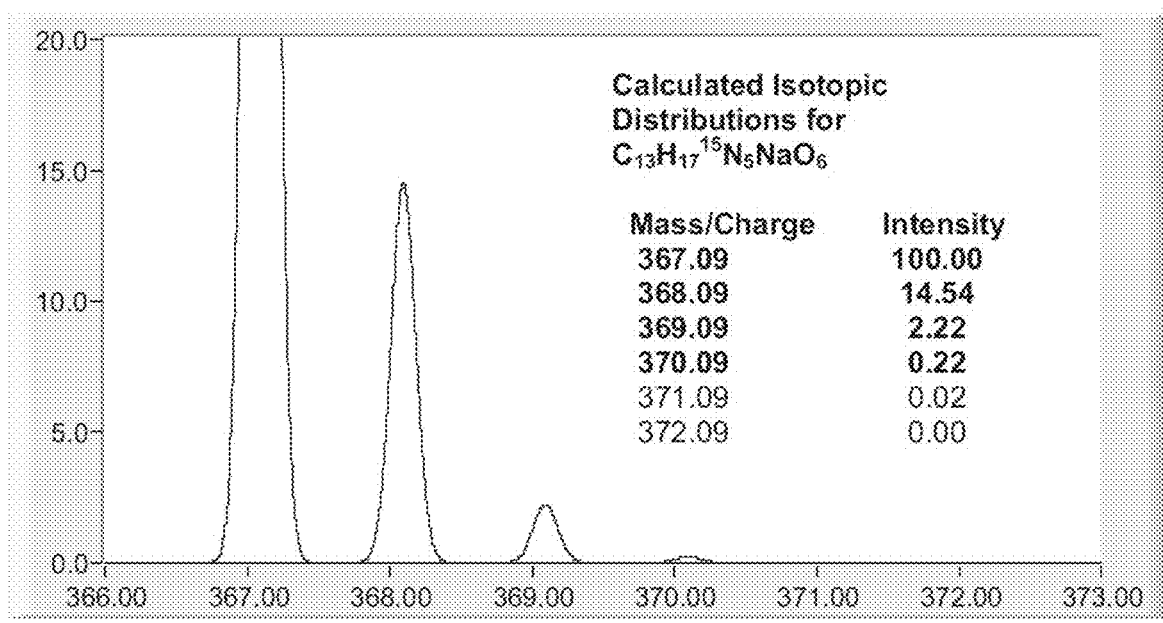

Fractions were lyophilized to dryness prior to resuspension in 18.2 MΩ $H_2O$. Concentrations of stock solutions were calculated by UV using a molar extinction coefficient of 12,300 @ 255 nm. See, for example, FIGS. 8A-C. Mass analyses of $^{15}N_5$-CEdG diastereomers were conducted using a Thermo-Finnigan LTQ FT ion trap mass spectrometer in the positive ion mode. A full scan MS for CEdG-A is shown in FIG. 3. The most intense ion was observed for the sodiated peak, $C_{13}H_{17}{}^{15}N_5NaO_6{}^+$: m/z 367.18 (obs), m/z 367.09 (calc). $^1H$ NMR assignments for CEdG-A: $^1H$ NMR (400 MHz, $d_6$-DMSO, 18° C.) δ 10.60 (s, 1H, N1-H̲), δ 7.93 (s, 1H, C8-H̲), δ 6.76 (d, 1H, C2-NH̲), δ 6.12 (dd, 1H, C1'-H̲), δ 5.30 (d, 1H, C3'-OH̲), δ 4.89 (vbr, 1H, C5'-OH̲), δ 4.36 (m, 1H, C2-NH—CH̲), δ 4.32 (m, 1H, C4'-H̲), δ 3.81 (m, 1H, C3'-H̲), δ 3.50 (ddd, 2H, C5'-H̲₂), δ 2.64 (ddd, 1H, C2'-H̲), δ 2.18 (ddd, 1H, C2'-H̲), δ 1.39 (d, 3H, C2-NH—CH—CH̲₃). $^{13}C$ NMR assignments for CEdG-A: (100.5 MHz, $d_6$-DMSO, 18° C.) δ 174.1 (C2-NH—CH—C̲OOH), δ 156.3 (C6), δ 151.5 (C2), δ 149.9 (C4), δ 136.1 (C8), δ 117.1 (C5), δ 87.6 (C3'), δ 82.9 (C1'), δ 70.8 (C4'), δ 61.7 (C5'), δ 49.0 (C2-NH—C̲H), δ ~39.5 (C2'), δ 17.7 (C2-NH—CH—C̲H₃). $^1H$ and $^{13}C$ NMR assignments for CEdG-B are nearly identical to the A isomer.

Synthesis of Oligonucleotides Containing Site-Specifically Modified CEdG Residues.

A synthetic scheme was devised for the quantitative preparation of oligonucleotides containing CEdG that can be readily accommodated on any standard DNA synthesizer using the conventional phosphoramidite technology. Oligos containing only pure D or L CEdG were prepared in a stereochemically pure manner using D- or L-alanine in a reaction that proceeds with retention of configuration. An NPE protected 2-fluoropurine phosphoramidite derivative was introduced into the polymer during standard oligonucleotide synthesis, and the reaction with D or L alanine was carried out prior to any deprotection step.

Specifically, stereochemically pure R- or S-CEdG oligonucleotides were synthesized by nucleophilic substitution with either D- or L-alanine on 2-fluoro-2'-deoxyinosine (2-FdI) containing oligos followed by deprotection and purification. Oligonucleotides were prepared using an ABI394 DNA synthesizer loaded with either standard or 2-F-dI-CE phosphoramidites (0.2 μM scale). For the preparation of CEdG containing oligonucleotides, F-dI-containing fully-protected oligomers still bound to the CPG support were suspended in an aqueous solution of 1M D- or L-alanine in 250 mM potassium carbonate at 50° C. for 40 hours. Complete removal of all protecting groups was achieved by extended reaction at 50° C. in concentrated ammonia for 7 days. Separation of the desired oligonucleotide from failure sequences and other impurities was achieved by ion-pairing chromatography on a 10 mm×250 mm×Bridge Prep C18 5 μm column (Waters, Milford, Mass.), using a 40 minute 9.0% to 9.5% gradient of acetonitrile vs 100 mM triethylammonium acetate (TEAA, Fluka, Milwaukee, Wis.) at a constant 45° C. All oligonucleotides were characterized by chromatography under the indicated conditions and analyzed by ESI-FT/MS on an LTQ-FT (Thermo-Finnigan, San Jose, Calif.) in the Mass Spectrometry Core of the City of Hope Cancer Center.

Figure 16:
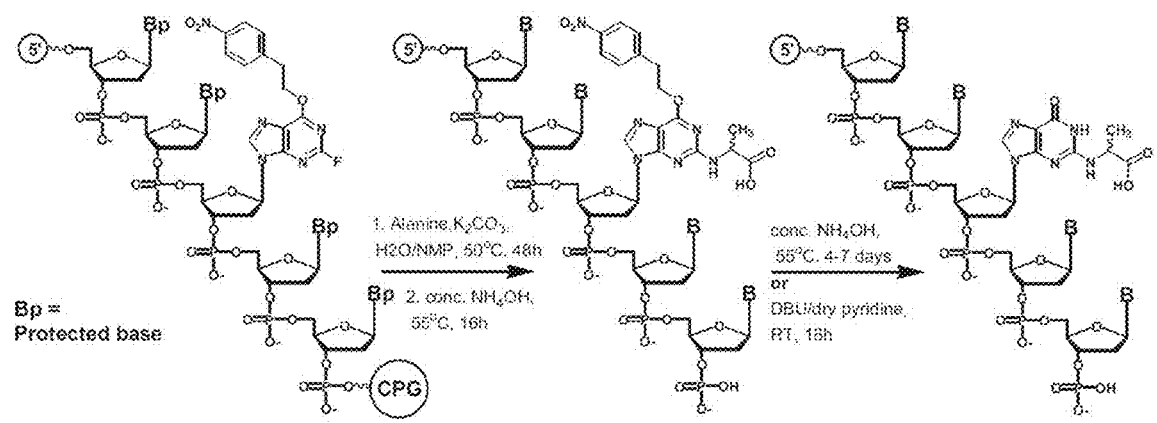
FIG. 16. Synthesis of oligonucleotides containing site-specifically modified CEdG.
Figure 17:
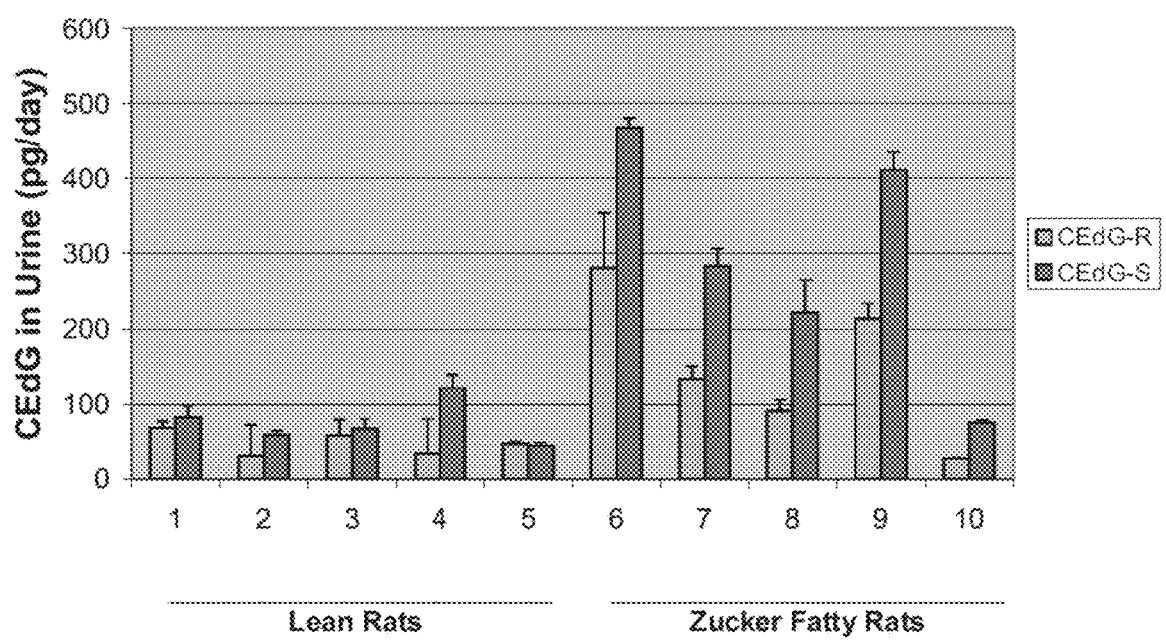
FIG. 17. Consistent elevation of CEdG in obese rats, nearly 10-fold in some examples, relative to lean controls. There is consistently more (S) isomer relative to (R) in biological samples from both rodents and humans.

This new synthesis is superior to previously known syntheses for CEdG because it allows for the preparation of oligos containing stereochemically pure R- or S-CEdG in high yield. Oligos containing uniquely substituted CEdG residues are used to calibrate the biological measurement of CEdG by serving as internal standards. They are also used in biochemical assays for examining the biological consequences of site-specific CEdG substitution in DNA, including, but not limited to, aspects of their repair and mutagenic potential (FIG. 16). This synthetic scheme may also be used to make site specific substitutions for other AGEs.

Stable Isotope Dilution.

Internal standards for other AGEs usually contain stable isotopes ($^{15}N$, $^{13}C$, $^{18}O$) to create a different pass from the related analyte. Different concentrations of the stable isotope substituted compounds are prepared and analyzed by MS in order to determine the response height of the ion current as a function of different concentrations. A calibration plot is made of concentration vs ion current response. This is typically a linear plot of concentrations ranging from anticipated lowest detectable amounts to highest expected. The ion current response increases with concentration. To measure CEdG in a biological sample, a known amount of stable isotope standard is "spiked" into the sample. Since the CEdG in the sample and the CEdG standard have different molecular weights, they can be resolved by MS. The ion current response of CEdG in the sample is compared to the response of the spiked isotopically enriched CEdG. Since the concentration of isotopically enriched standard in the sample is known, comparison allows for calculation of the amount of CEdG in the biological sample by fitting to the calibration plot.

Stability Studies of CEdG in Acidic Solution.

A 1.25 mM solution of CEdG-A, B or dG in 100 μL of 1M AcOH (pH 2.4) was stirred at 37° C. Aliquots (10 μl) were removed periodically and added to 40 μL of 2M TEAA (pH 7.0). HPLC product analyses were performed using an Alltech HS HyperPrep 100 BDS C18 8μ column. A gradient of 0 to 4% $CH_3CN$ over 5 min was followed by 6.5% $CH_3CN$ over 30 min. TEAA (pH 7) was kept constant at 50 mM. The ratio of free base (CEGuanine or Guanine) to intact nucleoside (CEdG or dG) was calculated by integration of the corresponding HPLC peaks (see inset in FIG. 4). The CEG free base was identified as Peak A by ESI-MS in negative ion mode. $C_8H_8O_3N_5$, observed: m/z 222.064; calculated: m/z 222.063.

Animal Studies.

Figure 5:
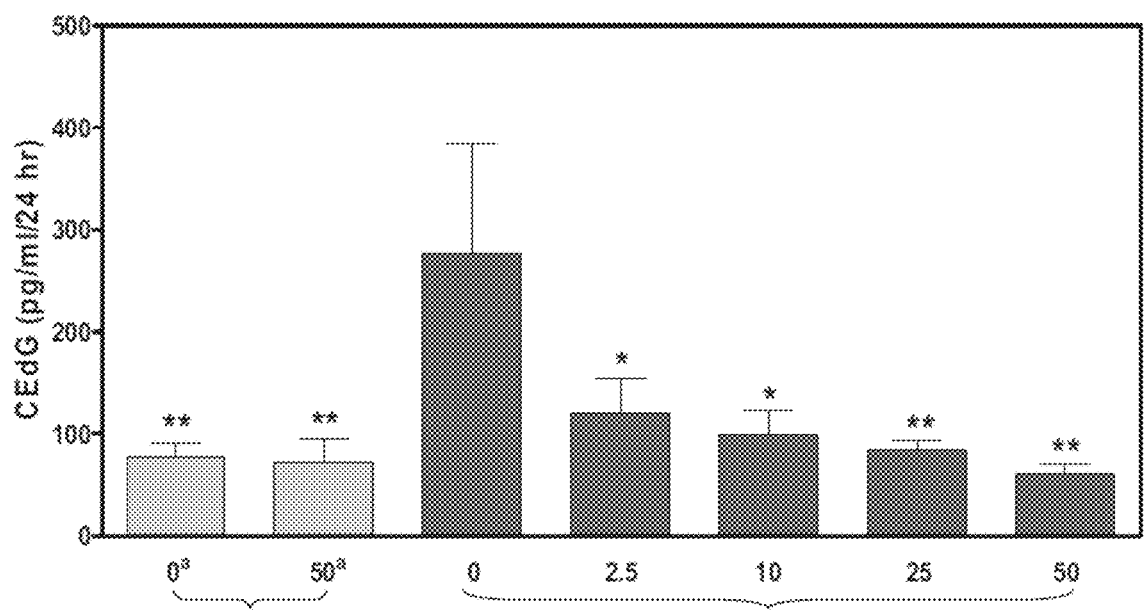
FIG. 5. Quantitation of CEdG in normal (light grey) and diabetic (dark grey) Sprague-Dawley rats. Superscript a ("$^a$"): Ordinate values represent ad libitum concentrations of the AGE inhibitor drug LR-90 (mg/L). *$P<0.05$ and **$P<0.01$ vs untreated diabetic animals (Bonferonni's test) (no asterisks).

All animal studies were carried out in compliance with the policies outlined in NIH Publication No. 85-23 "Guide for the Care and Use of Laboratory Animals." Male Sprague-Dawley rats were rendered diabetic by injection of streptozoticin and maintained as previously described.[18] AGE inhibitor LR-90 was administered ad libitum at concentrations ranging from 2.5-50 mg/L. Rats were housed in metabolic cages and urine was collected over a 24 hour period with several drops of toluene to inhibit microbial growth. Urine samples were stored at −80° C. prior to LC-MS/MS analysis for CEdG. The data in FIG. 5 represent 3 replicates from n different animals: non-diabetic controls, n=6; non-diabetic treated with 50 mg/L LR-90, n=5; diabetic control, n=3. For diabetic rats treated with varying doses of LR-90: 2.5 mg/L, n=4; 10 mg/L, n=5; 25 mg/L, n=6; 50 mg/L, n=8.

Urine Sample Preparation.

CEdG was concentrated from urine by solid phase extraction. A 1 ml strata-X-C cartridge was pre-conditioned by the sequential addition of 1 ml $MeOH/CH_3CN$ (1:1) followed by 2×1 ml 2% $H_3PO_4$. Then $^{15}N_5$-CEdG was added as an internal standard (final concentration 5 μg/ml), the sample was acidified with 10 μl of 86% $H_3PO_4$, and finally 0.4 mL of urine was introduced via suction filtration. The cartridge was then washed with sequential additions of 1 ml 0.1% $H_3PO_4$ and 1 ml MeOH and then dried under vacuum for 1 minute. Finally, CEdG/$^{15}N_5$-CEdG containing fractions were eluted from the cartridge with 1 mL 3% $NH_4OH$ in $MeOH:CH_3CN$ (2:8 v/v). The eluent was evaporated to dryness in a centrifugal concentrator and reconstituted with 200 μl 0.1% formic acid prior to LC-MS/MS injection.

Preparation of Mononucleosides from DNA.

Calf thymus or tissue-extracted DNA (100 μg) was dissolved in 80 μL of autoclaved 18.2 MΩ $H_2O$ containing 20 μL of sodium acetate (100 mM, pH 5.5), 20 μL of 1×TBE, 1.5 μL of 50 mM $ZnCl_2$, and 2.37 μL of a 100 mM AG or D-P stock solution. DNA was denatured at 95° C. for 5 min on a PCR heating block and then brought to 4° C. for 5 min. After equilibration to 45° C., 1.5 μL of 10 U/μL nuclease P1 was added. Alkaline phosphatase (4 μL of 8 U/μL), 1 U of bovine phosphodiesterase, and 14 μL of 100 mM $CaCl_2$ were added after 1 hour, and the hydrolysis/dephosphorylation was continued for another 7 hours. DNA concentrations were determined by UV spectroscopy (1 $OD_{260}$=50 μg/ml) and samples were stored at −80° C. prior to MS analyses. A 5 μL aliquot of digest was diluted to 200 μL and used for quantitation of 2'-deoxyguanosine by HPLC integration using a Beckman C18 reverse phase (25 cm×4.6 mm) column (Fullerton, Calif.). Separation was achieved isocratically using a mobile phase of 6% MeOH, 0.1% acetic acid in water.

DNA Isolation from Human Tissue.

Breast tumor and adjacent normal tissue were obtained from the frozen tumor bank of the City of Hope Pathology Core. A pea-sized section (~100 mg) of tissue was minced and suspended in 1.2 mL of digestion buffer (100 mM NaCl, 10 mM Tris HCl, pH 8, 25 mM EDTA, pH 8, 0.5% SDS, 0.2 mg/mL proteinase K, 10 mM D-penicillamine) and incubated at 50° C. in a water bath for 12-18 h. DNA was then extracted using an equivalent volume of phenol/chloroform/isoamyl alcohol (25:24:1). The aqueous fraction was separated and 0.5 volumes of ammonium acetate and 2 volumes of 100% ethanol were added. The DNA was spooled, washed twice with 70% ethanol, pelleted, and resuspended in autoclaved 18.2 MΩ water. The enzymatic hydrolysis was carried out as described above.

LC-ESI-MS/MS.

CEdG quantification was performed using LC-MS/MS. Measurement of 8-oxo-dG was performed as previously described.[19] CEdG and $^{15}N_5$-CEdG (internal standard) were synthesized and purified. Measurements were performed using an Agilent 1100 Capillary LC system (Agilent Technologies, Palo Alto, Calif.) in line with a Micromass Quattro Ultima Triple Quadrupole Mass Spectrometer (Micromass, Beverly, Mass.) operating in positive-ion mode. The detector settings were as follows: capillary voltage, 3.5 kV; cone voltage, 18 V; collision cell voltage, 11 V; source temperature, 350° C.; desolvation temperature, 150° C.; cone gas flow, 620 liter/h; and desolvation gas flow, 500 liter/h. The mass transitions monitored for CEdG and $^{15}N_5$-CEdG were 340.3→224.3 and 345.4→229.4 respectively. HPLC was accomplished using isocratic conditions with a mobile phase of 15% aqueous MeOH with 0.1% formic acid on a Prodigy ODS C-18 (25 cm×2.0 mm×5 micron) column (Phenomenex, Torrance, Calif.). The flow rate was 0.2 ml/min with a total run time of 30 min. The retention times for CEdG diastereomers A and B using these conditions were 9.3 and 16 min, respectively. The lower limit of quantitation for CEdG, defined as a peak height of ≥5× baseline noise, was 0.1 ng/ml in the starting solution or 0.2 pg on column.

LC-ESI-MS/MS Alternative method. Following thawing, 100 μL of urine was added to 50 μL of 7.5 ng/mL (R, S)-$^{15}$N$_5$-CEdG, and 400 μL 10% formic acid (FA) in H$_2$O. Oasis MCX 1 cc solid phase extraction columns were conditioned with 1 mL MeOH and equilibrated with 1 mL 0.1% FA in H$_2$O prior to sample loading. Columns were washed with 2 mL MeOH and 2 mL 2% FA in H$_2$O. CEdG was eluted with 1 mL of 2% NH$_4$OH in MeOH, dried by vacuum centrifugation, and resuspended in 100 μL 0.1% FA in H$_2$O. Calibration standards were processed in parallel to urine samples. Liquid chromatography was performed using an Agilent 1290 Infinity Binary UHPLC with an Agilent alkyl reversed-phase ZORBAX SB-Aq column (2.1×50 mm, 1.8 μm) (40° C.) using mobile phases A (0.1% FA in H$_2$O) and B (0.1% FA in ACN). Analytes were eluted using the following gradient: 0-4 min, 3-10% B; 4-4.5 min, 10-100% B; 4.5-5 min, 100-3% B, at a flow rate of 0.4 mL/min. Isotope-dilution LC-ESI-MS/MS was performed in positive ion mode using an Agilent 6400 triple quadrupole mass spectrometer with multiple reaction monitoring to observe mass transitions m/z 340.1→224.1 (CEdG) and m/z 345.1→229.1 ($^{15}$N$_5$-CEdG). The relative MS response of a fixed amount of (R, S)-$^{15}$N$_5$-CEdG to increasing concentrations of (R, S)-CEdG was used to generate a standard curve ($r^2$>0.99). Sample CEdG concentrations were determined using isotope dilution with fitting to the standard curve using the Agilent MassHunter WorkStation Quantitative Analysis software. The lower limit of detection on the instrument was 0.01 ng/mL (30 pM), while the lower limit of quantification was 0.1 ng/mL (0.3 nM). Total volume of urine excreted per 24 h was used to calculate total mol CEdG.

For urine analyses and calf thymus DNA digests, calibration curves were constructed using 0.75, 1.5, 3, 6, 12, 24, and 48 ng/mL of synthetic CEdG in urine or in blank nucleoside digestion buffer. For human breast tissues, CEdG concentrations used for calibration were 0.19, 0.38, 0.75, 1.5, 3, and 6 ng/mL. Linearity of the calibration curves were demonstrated with R-squared values of ≥0.996. Inter- and intra-day accuracy of the assay across the range of the standard curve was established to be 96% and 94% of target concentrations, respectively. The assay was also determined to be unbiased with both inter- and intra-day precision within ±6%. Quantification of 2'-deoxyguanosine (dG) was performed by HPLC integration of DNA digests and final values were expressed as CEdG/10$^7$dG.

Urine extracts or mononucleoside digests were spiked with 20 μL of 100 ng/mL $^{15}$N$_5$-labeled CEdG and 10 μL of 86% phosphoric acid. Samples were then loaded onto strata-X-C cation mixed mode columns that had been pre-conditioned with MeOH/CH$_3$CN (1:4) followed by 2% phosphoric acid. After sample loading, columns were washed with 0.1% phosphoric acid, followed by MeOH. Nucleosides were eluted with 3% ammonium hydroxide in MeOH/CH$_3$CN (1:4) and evaporated to dryness in a centrifugal concentrator. Samples were reconstituted with 100 μL of 0.1% formic acid and analyzed directly by LC-MS/MS. Recovery of CEdG diastereomers as well as $^{15}$N$_5$-CEdG from urine and mononucleoside digests was determined to be 85+/−0.9%.

Synthesis and Characterization of CEdG Isotopomers.

Isotopomers of CEdG were prepared by a modification of the method of Ochs and Severin.[17] Reaction of $^{15}$N$_5$-dG with DL-glyceraldehyde in phosphate buffer afforded the desired products as a ~1:1 mixture of diastereomers in ~60% yield. Unenriched CEdG diasteromers were prepared in an analogous manner. The N$^2$ amino group of dG catalyzes the dehydration of glyceraldehyde to yield the hemiacetal of MG in situ, which then reacts to provide CEdG either directly by condensation at N$^2$ or alternatively via the rearrangement of an intermediate N$^1$, N$^2$ cyclic diol. The two diastereomers of CEdG were readily resolved by HPLC and eluted at 24 and 29 minutes (FIG. 2) on a C18 reverse phase column. In spite of significant differences in chromatographic retention times, both the proton and carbon NMR spectra for CEdG-A and B were essentially superimposable, with the chemical shift differential on the order of <0.1 ppm for proton and <1.0 ppm for carbon.

Mass analyses of the CEdG isotopomers were performed using a Thermo Finnigan LTQ ion trap mass spectrometer in the positive ion mode. The most intense signal in the parent ion spectrum of the isotopically enriched standard corresponded to the sodium salt of $^{15}$N$_5$-CEdG at m/z 367 [PNaH]$^+$ (FIG. 3). The disodium salt [PNa$_2$]$^+$ and the dihydro adduct [PH$_2$]$^+$ were also observed at m/z 389 and 345, respectively. Collision induced dissociation of the m/z 367 parent ion gave rise primarily to the sodiated base ion [BNaH]$^+$ at m/z 251. The observed isotopic distribution for $C_{13}H_{17}{}^{15}N_5NaO_6$ was found to be in good agreement with the calculated values.

Stability of CEdG to Acid-Catalyzed Depurination and Sidechain Isomerization.

The chemical stability of CEdG was examined as an important criterion for evaluating its suitability as a quantitative biomarker. Purified stereoisomers of synthetic CEdG were subjected to acidic conditions (1 M AcOH at 37° C.) and the extent of released free base and diastereomer interconversion was monitored by HPLC as a function of time. Analogous experiments were performed for dG and the results are presented in FIG. 4. The approximate half-lives for depurination were 750 and 500 min for the A and B isomers respectively, whereas dG was observed to be less stable, with a half-life of 440 min under these conditions. No racemization of the sidechain stereocenter was detected during acidic hydrolysis, i.e., no interconversion of CEdG isomers A and B was observed.

Urinary CEdG Measurement in Type 1 Diabetic Rats.

A diabetic animal model was used to examine the relationship between glycemic status and CEdG levels. Rats rendered diabetic by streptozoticin (STZ) treatment possess elevated MG relative to normal controls and thus appeared likely to exhibit an increased burden of CEdG adducts. The effect of AGE inhibitor, LR-90, was also examined. The results of these experiments are shown in FIG. 5. Analyses of urine from non-diabetic control animals collected over a 24 hr period revealed mean CEdG levels of 77 μg/ml (FIG. 5). The induction of diabetes increased the level of excreted CEdG by ~4 fold. Administration of LR-90 to diabetic rats ad libitum at a dose corresponding to 2.5 mg/L resulted in a 2.3 fold decrease in CEdG titer. Increasing concentrations of LR-90 led to a dose dependent reduction in CEdG, and at 25 mg/L the adduct level in urine was comparable to that of non-diabetic animals. In contrast, administration of LR-90 at doses up to 50 mg/L in normal controls had no significant effect on CEdG levels. 8-oxo-dG was also measured as an indicator of oxidative stress in normal and diabetic rats; however, excreted 8-oxo-dG in diabetic animals was not statistically different (P>0.05) from controls.

CEdG in Organs of Zucker Fatty Rats.

Figure 18A:
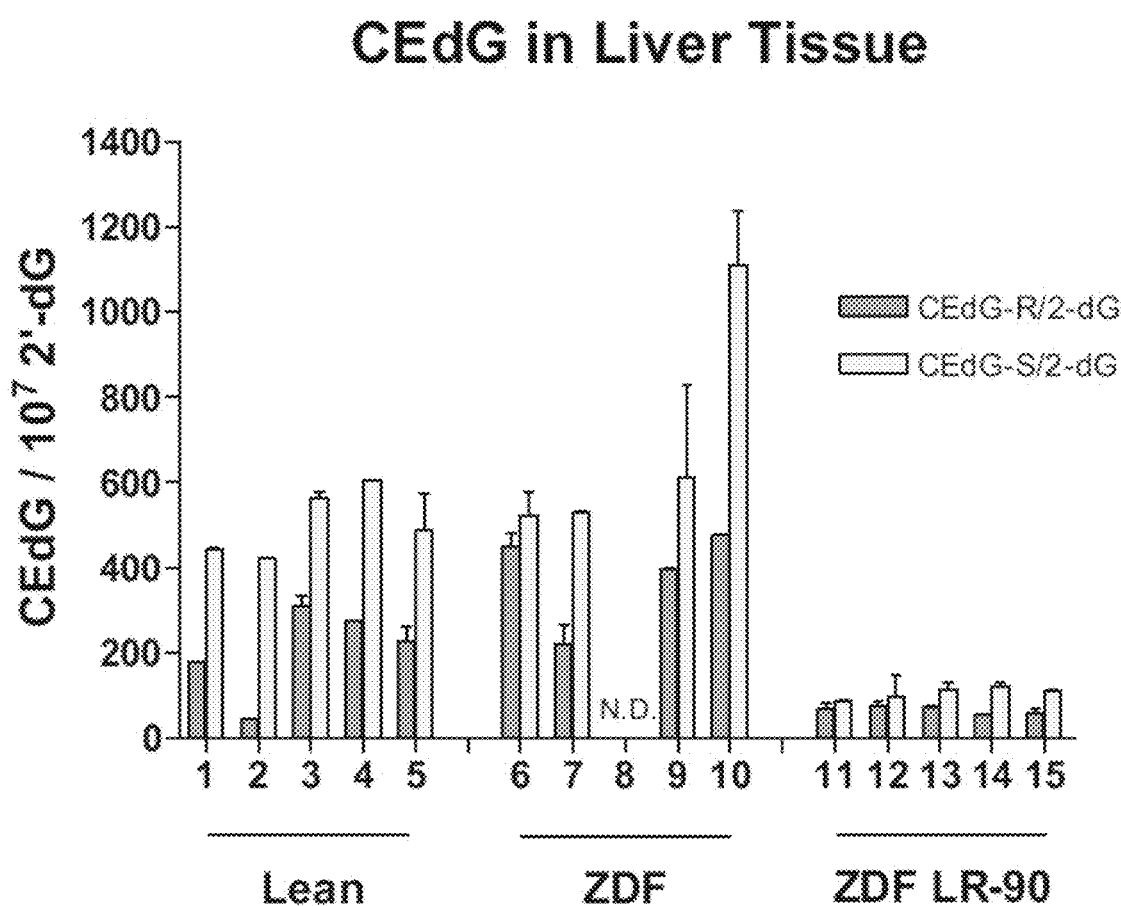
FIGS. 18A-18C. CEdG levels from tissue-extracted DNA in the liver (FIG. 18A), pancreas (FIG. 18B) and kidney (FIG. 18C) of Zucker rats, lean controls and Zucker rats treated with the glycation inhibitor LR-90.
Figure 18B:
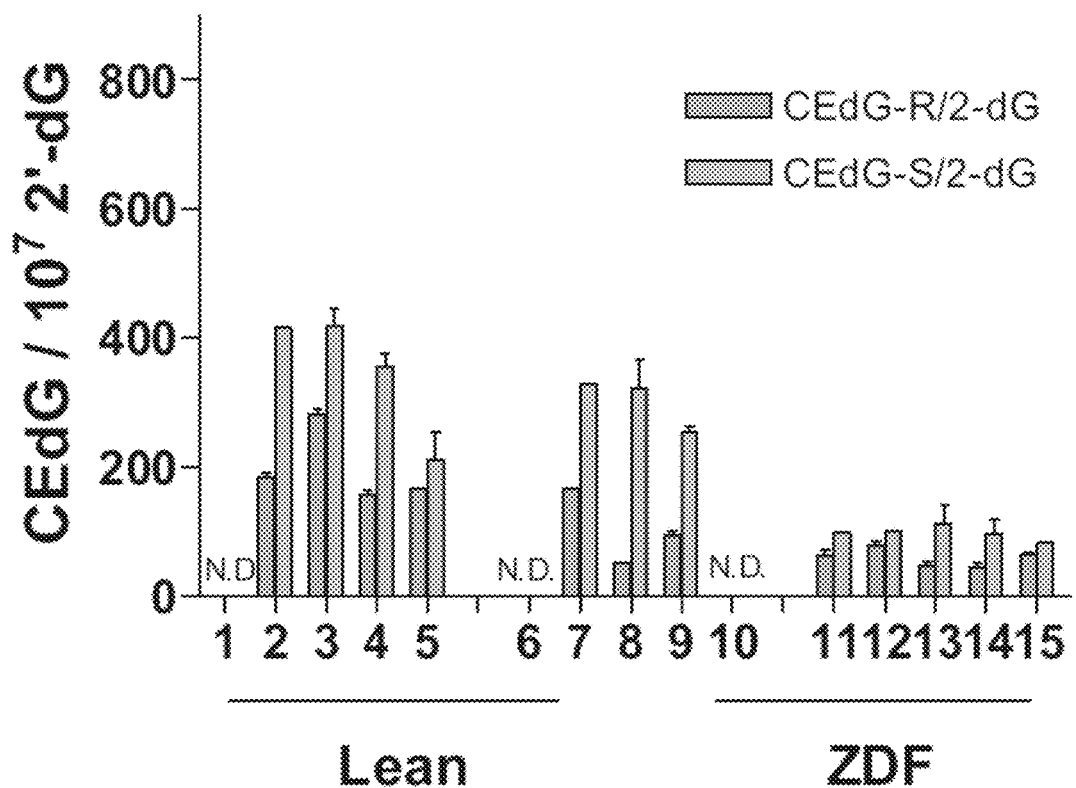
Figure 18C:
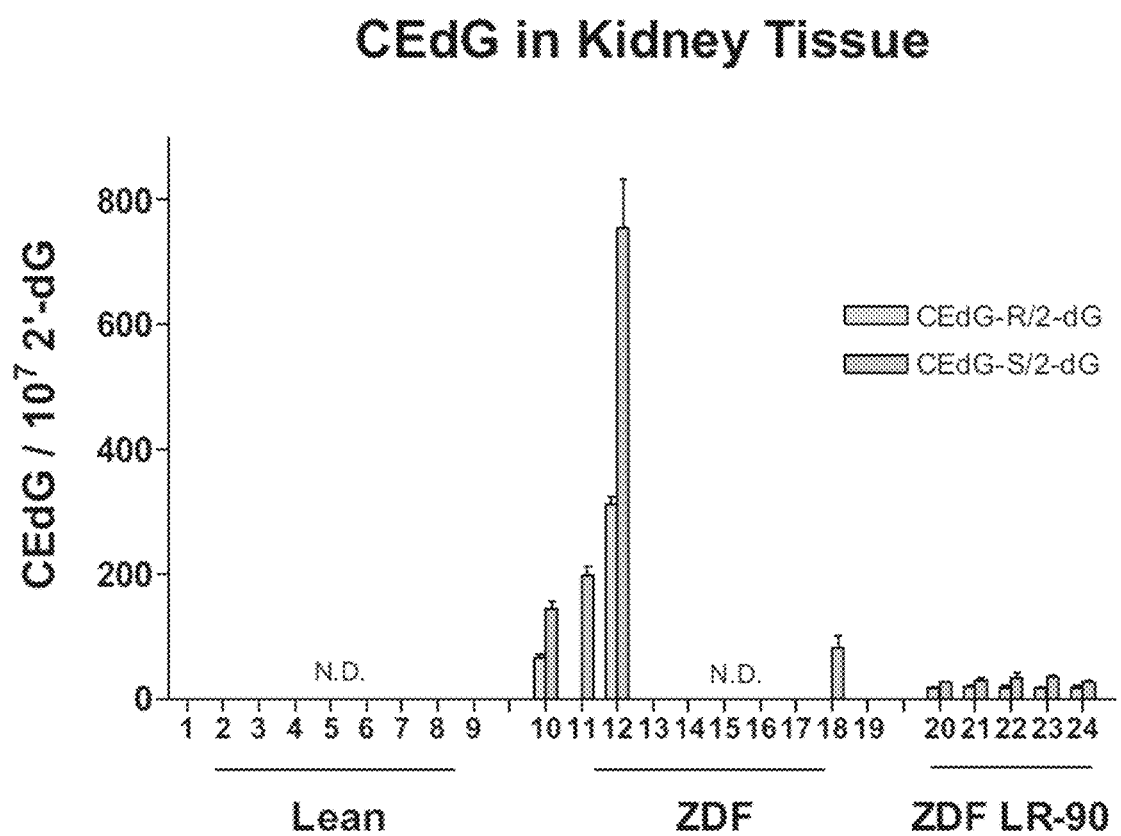

The Zucker rat is a morbidly obese, hyperinsulinemic model for Type 2 diabetes resulting from homozygous knockout of the leptin receptor. In order to determine whether elevated circulating glucose in the Zucker rat correlates with increased tissue DNA glycation, CEdG levels from tissue-extracted DNA were measured in selected organs and compared to lean controls and to Zucker rats treated with the glycation inhibitor LR-90. Data for liver, pancreas and kidney are shown in FIGS. 18A-C. Relative to lean rats, CEdG levels were found to be elevated only in kidneys. In lean animals, CEdG was below the level of detection in 9/9 animals, whereas it was elevated in 5/9 Zucker rats. All three organs of Zucker rats had a net lowering of CEdG levels following treatment with LR-90. These data show that CEdG determination can be used to monitor tissue glycation levels in response to chemotherapy.

CEdG in Calf Thymus DNA.

Figure 6:
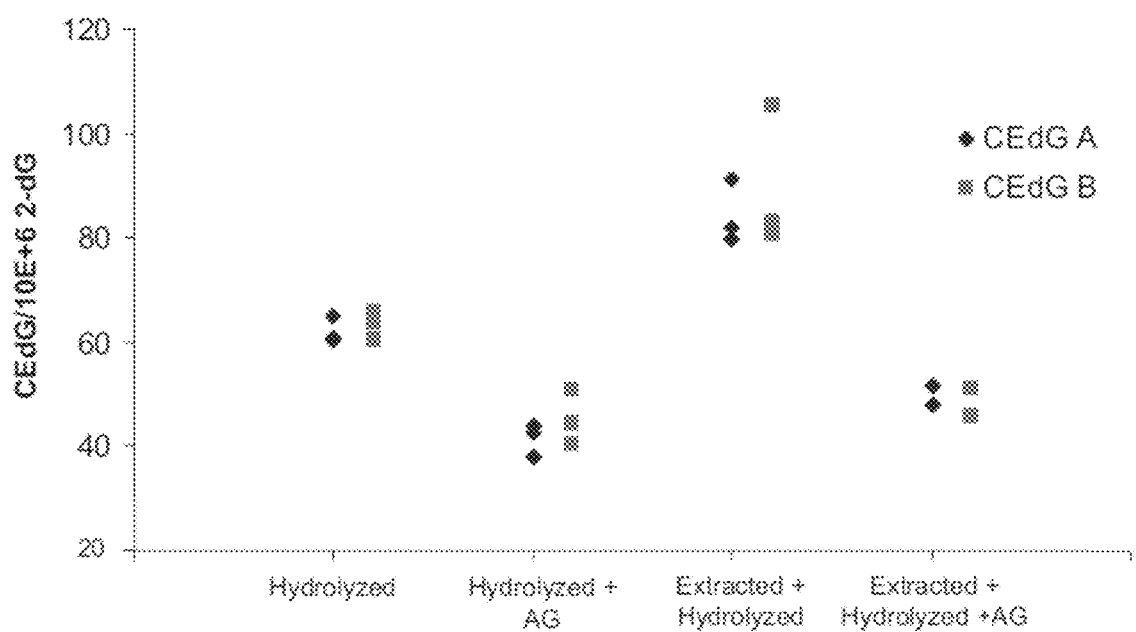
FIG. 6. LC-ESI-MS/MS measurements of CEdG diastereomers in calf thymus DNA subjected to various workup procedures. Hydrolyzed samples correspond to DNA treated with nuclease P1/alkaline phosphatase/phosphodiesterase. Calf thymus DNA samples were also reacted with proteinase K (Extracted) prior to hydrolysis. Levels of CEdG were measured in the presence or absence of carbonyl scavenger AG.

Commercial grade calf thymus DNA was used as a model substrate for developing a protocol for CEdG quantitation in double-stranded DNA. DNA was hydrolyzed and dephosphorylated by sequential addition of nuclease P1, alkaline phosphatase and phosphodiesterase. Then, mononucleosides were concentrated by solid phase extraction prior to LC-MS/MS analyses. The results of these experiments are shown in FIG. 6. Initial determinations yielded values of CEdG in the range of 60-66 CEdG/$10^6$ dG. These surprisingly high levels showed that some CEdG may have been formed artifactually during the hydrolysis and dephosphorylation. Additional CEdG may have been formed due to the release of MG from the protein reagents used in the workup during prolonged incubation. Proteins can bind MG reversibly, and up to 90% of cellular MG may be sequestered in this manner. In order to prevent additional reactions of adventitiously generated MG with DNA, carbonyl scavenging agents AG or D-P were added prior to DNA digestion and dephosphorylation. These reagents sequester MG and other alpha-oxoaldehydes by forming stable cyclic aminotriazine and thiazolidine derivatives respectively. Concentrations of AG from 0.5 to 50 mM were added prior to workup, and CEdG levels were measured in order to determine the optimal concentration required to achieve stable, reproducible levels. The addition of 10 mM AG prior to sample processing resulted in a modest but significant drop in adduct levels (45-50 CEdG/$10^6$ guanines) in calf thymus DNA, suggesting that ~15 CEdG/$10^6$ guanines were formed as a direct result of the hydrolysis and dephosphorylation protocol.

Since the extraction of DNA from biological samples requires extended reaction with proteinase K (up to 24 h), it was investigated whether this treatment could also contribute to artifactual CEdG formation. Accordingly, calf thymus DNA was subjected to mock proteolysis prior to hydrolysis and workup in the absence of carbonyl scavenger. FIG. 6 reveals an increase in adduct levels significantly higher than those observed following hydrolysis alone, with values ranging from 80-100 CEdG/$10^6$ guanines. The addition of 10 mM AG in two aliquots prior to the mock lysis treatment and hydrolysis/dephosphorylation steps resulted in a drop in measured CEdG levels comparable to that observed previously for calf thymus DNA subjected only to the hydrolysis/dephosphorylation in the presence of AG. No apparent stereoisomer bias was detected in any of these samples, i.e., the ratio of R-CEdG:S-CEdG was not significantly different from 1:1.

Measurement of Urinary CEdG in Post-Menopausal Women Undergoing Treatment with Aromatase Inhibitors.

Figure 19A:
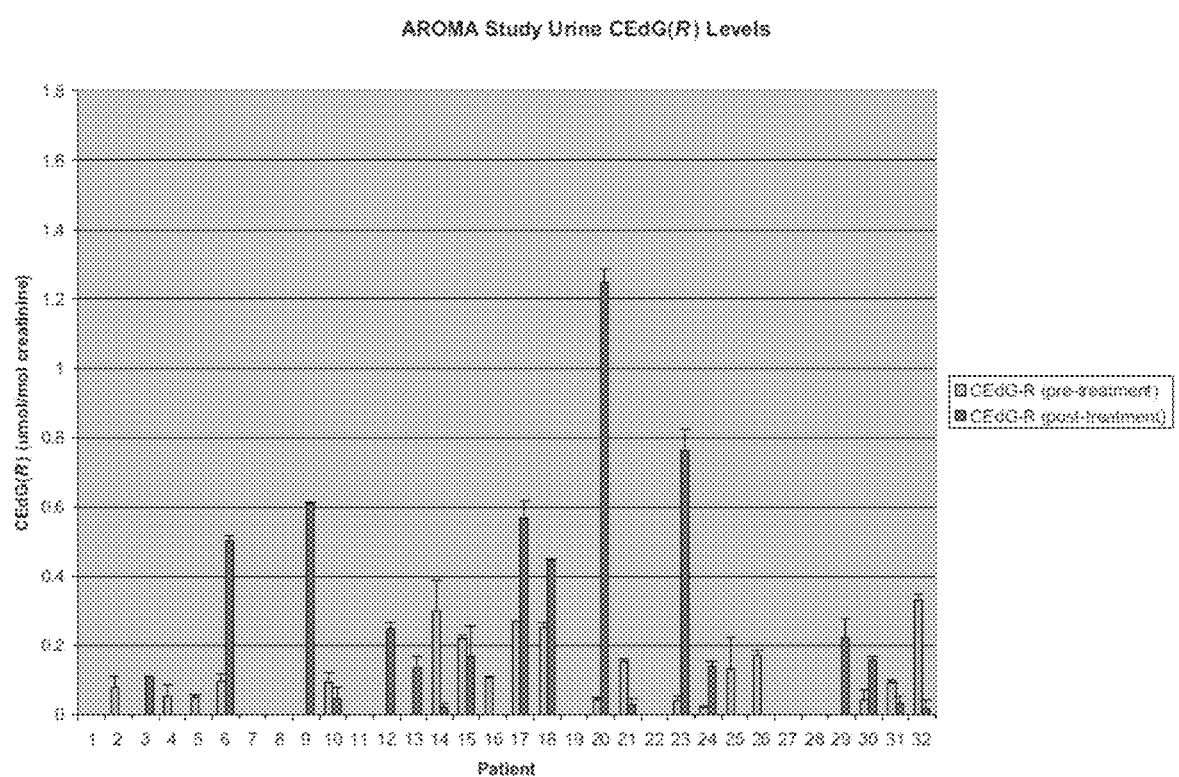
FIGS. 19A-19B. Measurement of urinary R-CEdG and S-CEdG isomers in post-menopausal women undergoing treatment with aromatase inhibitors.
Figure 19B:
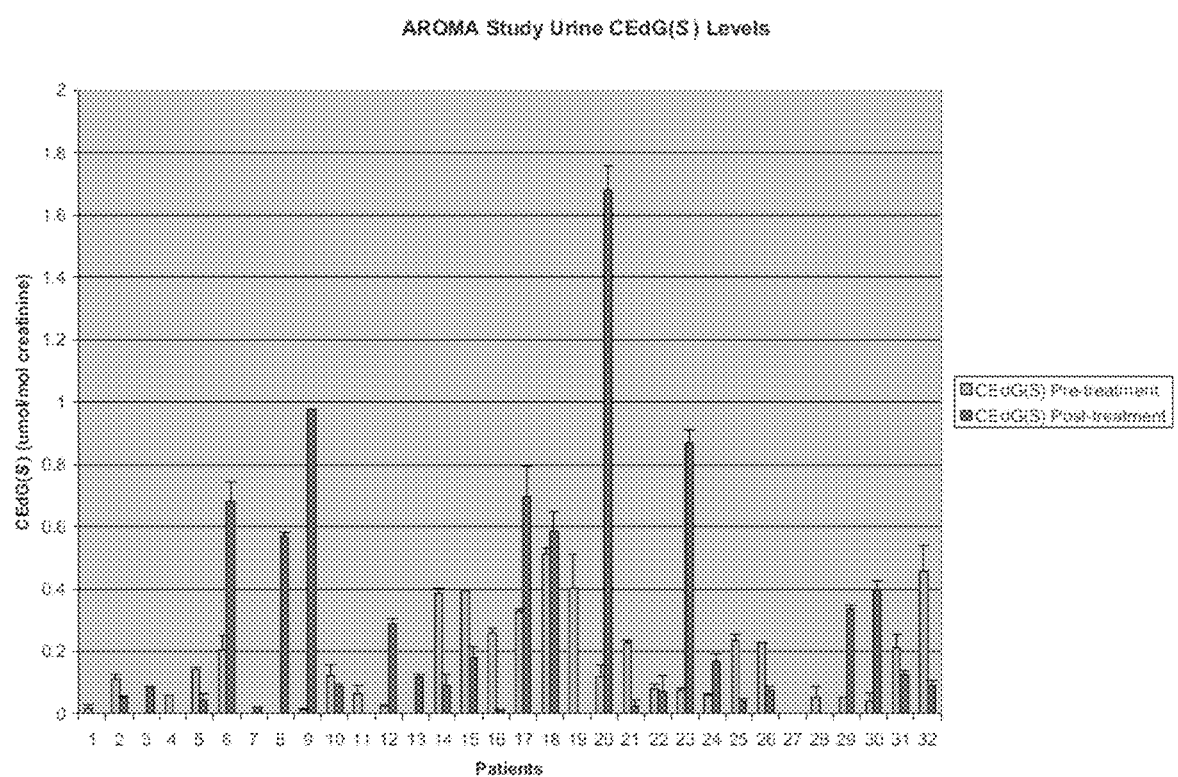

One noted side-effect of treatment with aromatase inhibitors (AI) in cancer therapy is an impairment of cognitive function, which may be linked to enhanced glycation in the brain. Enhanced brain glycation is a contributing factor in the pathology of Alzheimer's disease. In order to examine whether treatment with aromatase inhibitors can affect glycation status, urine from 32 patients was collected just prior to and 6 months following administration of AI, and levels of CEdG were measured in urine. Data for the R- and S-CEdG isomers are shown in panels A and B, respectively, of FIG. 19. In the case of the (R) isomer, 12/32 patients show significantly higher levels after AI treatment, a trend also observed for 14/32 patients when levels of the (S) isomer are considered. Some of these post-treatment levels are very high, much higher than any observed pre-treatment levels. There is also good consistency between the two independent biomarkers. For example, in patients 3, 6, 9, 12, 13, 17, 18, 20, 23, 24, 29 and 30, both stereoisomers are elevated post-AI treatment. If these changes are correlated with decreased mental acuity over time, CEdG measurement can also be used to identify patients at risk for cognitive impairment. Additionally, one or more CEdG inhibitors, such as LR-90, may be administered to a subject undergoing chemotherapy in order to prevent or reduce the cognitive impairment that may accompany chemotherapy.

CEdG Measurement in Human Solid Tumors Vs Adjacent Tissue.

Figure 20A:
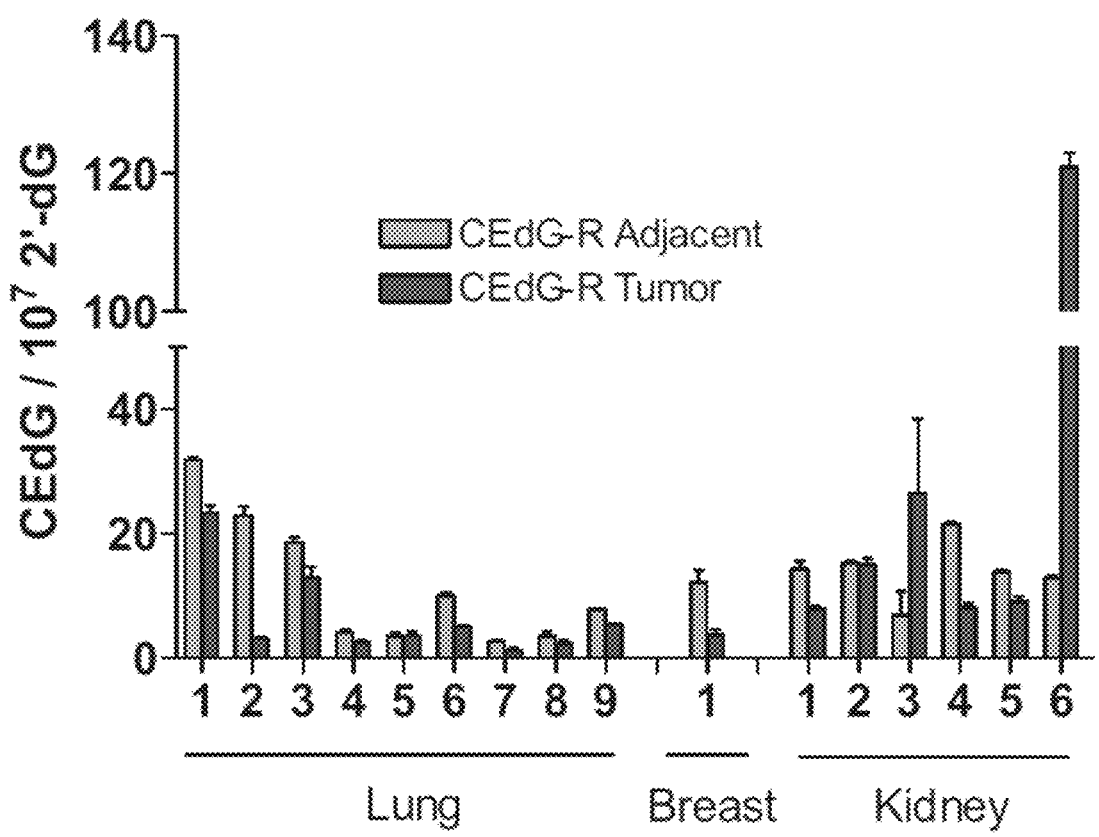
FIGS. 20A-20B. R-CEdG and S-CEdG distribution in human solid tumors and adjacent tissue in lung, breast and kidney cancers.
Figure 20B:
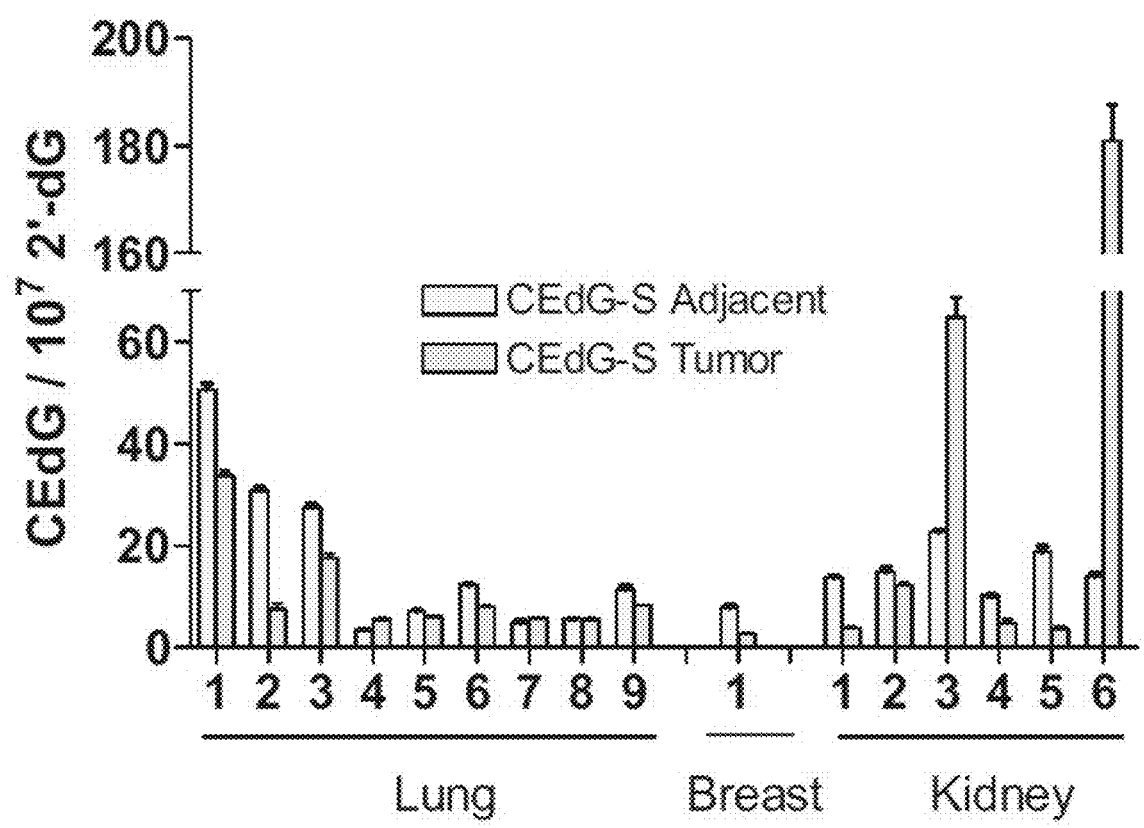

Frozen tumor specimens and adjacent tissue were obtained from the City of Hope Tumor Bank. DNA was extracted as described and analyzed for CEdG. Results are shown in FIGS. 20A-B for R- and S-CEdG in lung, breast and kidney cancers. In lung cancers CEdG was observed at lower levels in tumor relative to adjacent tissue in the majority of samples. This same phenomenon was observed for the single breast cancer sample analyzed. These trends are followed for both isomers. In the case of kidney cancers, the situation is more complex, with samples 3 and 6 showing the opposite trend of higher CEdG in tumor relative to adjacent tissue. In sample 6, the levels of (R) and (S) isomers were 13 and 18 fold higher respectively in tumor relative to adjacent tissue. Other samples, such as 1, 4 and 5, follow the trend observed in the lung and breast samples.

These variations in CEdG between tumor and adjacent tissue represent corresponding levels of glycolytic stress. In order to avoid the pro-apoptotic effects of methylglyoxal produced as a result of enhanced glycolysis, solid tumors must restrict its accumulation. Tumors with lower levels of CEdG relative to adjacent tissue, can successfully minimize their glycolytic stress in spite of maintaining elevated glycolysis. This is likely due to overexpression of the methylglyoxal scavenging enzymes glyoxalase 1 and aldose reductase in tumors, as well as enhanced removal of CEdG from DNA by repair enzymes. Tumors with elevated levels of CEdG relative to adjacent tissue are predicted to be genetically unstable, and more sensitive to chemotherapy as a result of the cytotoxic accumulation of methylglyoxal. Thus, another embodiment is a method of predicting which tumors of a cancer patient are more susceptible to chemotherapy by testing CEdG levels in tumor samples. If the CEdG levels are high, then the tumor is more likely to be receptive to chemotherapy treatment. Measurement of CEdG can also be used to identify which cancers which can benefit from targeting glyoxalase 1 and/or aldose reductase, in order to restore their sensitivity to chemotherapy. CEdG measurement can provide a direct means for identifying tumors most likely to benefit from these approaches.

Quantitation of CEdG in a Human Breast Tumor and Adjacent Normal Tissue.

Many cancer cells in the hyopoxic tumor microenvironment primarily utilize glycolysis to meet their energetic demands. This glycolytic phenotype (Warburg effect) is characterized by constitutive cell surface expression of glucose transporter proteins such as GLUT-1, and forms the basis for the diagnostic use of [18]FDG-PET in the imaging of breast and other cancers.[26,27] Enhanced glycolytic flux suggests that breast tumors might exhibit abnormal levels of AGEs including CEdG. Accordingly the levels of CEdG diastereomers were measured in DNA extracted from a clinical breast tumor specimen as well as adjacent normal tissue. The data in Table 1 reveal some significant (P<0.05) differences in the levels of CEdG between tumor and normal tissue. Both stereoisomers were observed at ~3-fold higher levels in normal relative to tumor tissue (CEdG-A (R-CEdG), P=0.02; CEdG-B (S-CEdG), P=0.003). In the column under CEdG/$10^7$dG, "a" indicates P=0.08 versus CEdG-B in normal issue; "b" indicates P=0.02 versus CEdG-A in adjacent normal tissue; "c" indicates P=0.003 versus CEdG-B in adjacent tumor tissue; and "d" indicates P=0.03 versus CEdG-A in tumor tissue.

TABLE 1

CEdG isomers from a human breast tumor and adjacent normal tissue.

|  |  | CEdG (fmol) | dG (fmol) | CEdG/$10^7$ dG |
|---|---|---|---|---|
| CEdG-A | Normal | 234 ± 24.9 | 1.91 × $10^8$ | 12.3$^a$ ± 1.3 |
|  | Tumor | 247 ± 11.6 | 6.48 × $10^8$ | 3.9$^b$ ± 0.2 |
| CEdG-B | Normal | 151 ± 4.98 | 1.91 × $10^8$ | 7.9$^c$ ± 0.3 |
|  | Tumor | 173 ± 6.64 | 6.48 × $10^8$ | 2.7$^d$ ± 0.1 |

$^a$P = 0.08 versus CEdG-B in normal tissue.
$^b$P = 0.02 versus CEdG-A in adjacent normal tissue.
$^c$P = 0.003 versus CEdG-B in adjacent tumor tissue.
$^d$P = 0.03 versus CEdG-A in tumor tissue.

Within normal tissue, the levels of CEdG-A(R) and B(S) were not significantly different (P=0.08), while in tumor there was a small bias favoring CEdG-A (R) (P=0.03). Levels of CEdG in DNA extracted from either breast tumor or adjacent tissue in the absence of carbonyl scavenger were ~1.5-2.0 fold higher; however, artifactual formation was inhibited by the addition of 10 mM D-penicillamine in two aliquots during both the cell lysis/DNA isolation and hydrolysis/dephosphorylation steps. $^{15}$N-enriched isotopomers of CEdG differing from the unlabeled adducts by 5 amu were synthesized, which provided sufficient mass resolution for accurate and reproducible quantitation using the stable isotope dilution method.

Figure 4:
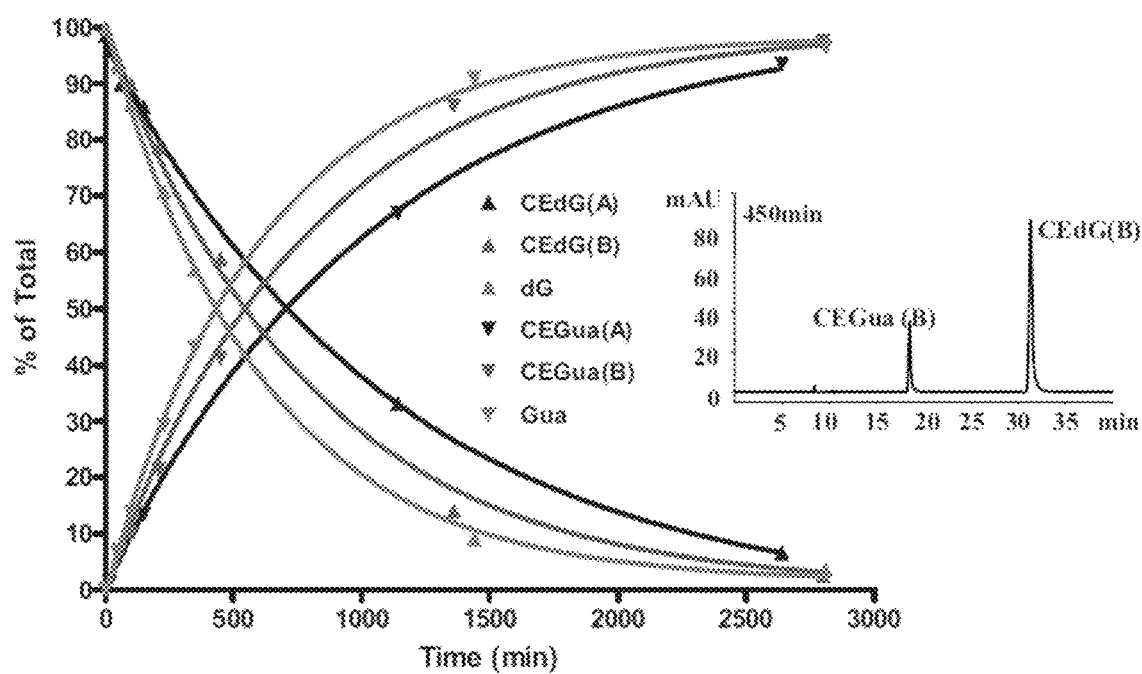
FIG. 4. Time course product profiles of the reaction of dG and the A (R) and B (S) stereoisomers of CEdG with 1 M AcOH at 37° C. The inset shows the HPLC chromatogram of the reaction of CEdG-B at 450 min.

The ability to simultaneously resolve and quantitate both diastereomers of CEdG provides two independent parameters for assessing DNA glycation levels within a single sample. The biological significance of the CEdG diastereomer ratio in vivo may reflect stereochemical biases in adduct repair or polymerase bypass. Of course, examination of the CEdG stereoisomer distribution in vivo by LC-ESI-MS/MS would only be meaningful if the rate of stereochemical interconversion was negligible. Regarding overall adduct stability, loss of the CEGuanine base from either stereoisomer during workup would result in the generation of abasic sites leading to an underestimation of true nucleoside adduct levels, which was of particular concern since CEdG undergoes depurination more readily than dG at elevated temperatures. The extent of depurination and racemization was quantified by monitoring free base formation and isomer interconversion under acidic conditions at 37° C. rather than at non-physiological temperatures. FIG. 4 shows that the CEdG diastereomers possess similar stability, and are slightly more resistant to depurination under acidic conditions than dG. This fact, together with the prohibitive barrier to stereochemical interconversion, indicates that determination of CEdG diastereomer ratios may be plausibly used in quantitative biomarker studies. Various quantifications of CEdG are found in FIGS. 9-15.

Figure 7:
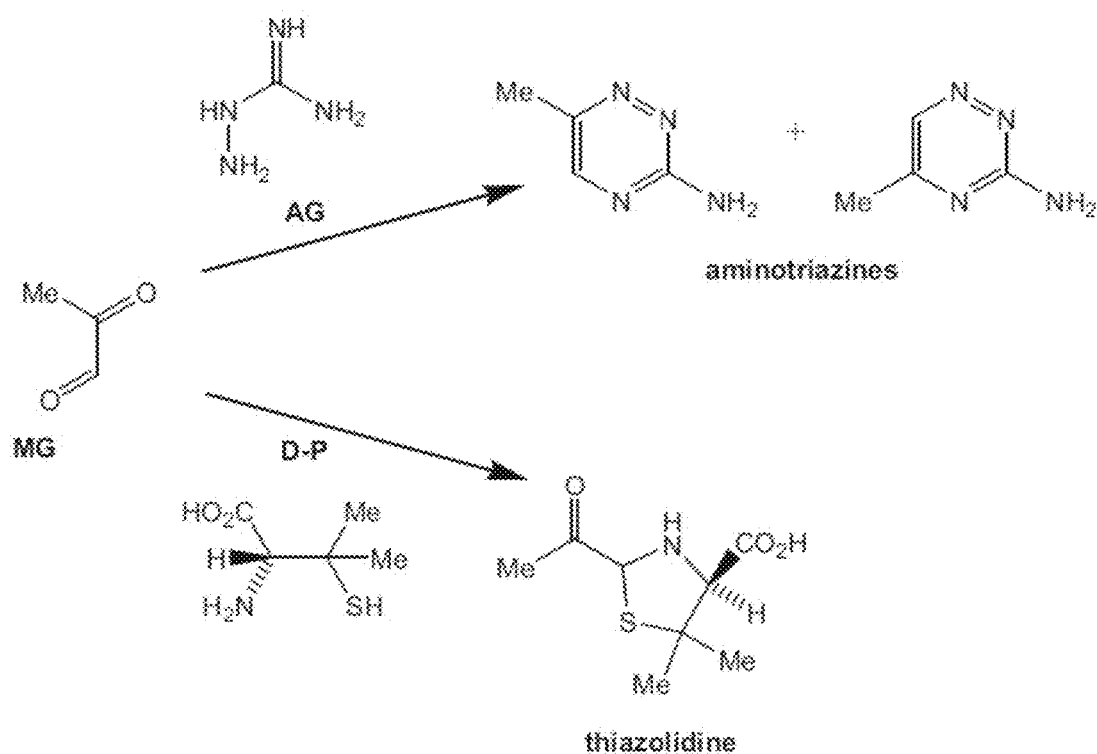
FIG. 7. Reactions of carbonyl scavengers AG and D-P with MG yield isomeric aminotriazines (top) and 2-acylthiazolidine (bottom).

One important confounding factor in the quantitation of adducts resulting from oxidative or oxoaldehyde DNA modification is artifactual product formation during sample isolation and workup. The problems surrounding the measurement of 8-oxo-dG using GC-MS and/or mildly oxidizing workup conditions have been detailed previously.[36-38] In the case of CEdG adducts, the presence of MG during the workup could complicate the accurate determination of endogenous levels. The effects of carbonyl scavenger addition prior to the enzymatic digestions were examined due to the high background levels of CEdG detected in reagent grade calf thymus DNA. Scavengers such as AG and D-P react rapidly with MG and other oxoaldehydes to yield aminotriazines and thiazolidines respectively (FIG. 7) which are relatively unreactive electrophiles. D-penicillamine reacts with MG 60 times faster than AG, and thus may be more advantageous for CEdG determinations requiring DNA isolation from complex tissue matrices.

MG bound reversibly to proteins was predominantly responsible for the formation of DNA glycation artifacts observed during the isolation and workup of dsDNA. Extraction and workup procedures which expose DNA for extended periods to cell lysates and partially purified enzyme reagents increase the probability for the ex vivo formation of CEdG, necessitating the need for carbonyl scavengers. MG-BSA conjugates prepared by incubating MG with BSA can be used as reagents to induce DNA damage in cultured mammalian cells. The data in FIG. 6 suggest that the addition of AG or D-P can largely eliminate artifactual CEdG formation. Minimizing exposure to proteins by shortening the enzymatic lysis and hydrolysis/dephosphorylation steps may also reduce the requirement for carbonyl scavengers.

A diverse array of tumor and corresponding control tissues were examined to determine whether the trends noted in the breast cancer specimen are a general feature of tumors which display elevated levels of glycolysis. The finding of significantly lower CEdG in breast tumors relative to adjacent normal tissue can potentially be explained by the observation that glycolytic cancers possess lower levels of MG as a result of overexpression of the glyoxalase (Glo) system. This highly evolutionarily conserved system consists of two non-homologous zinc metalloenzymes Glo1 and Glo2, which act sequentially to convert MG into lactate using reduced glutathione (GSH) as a catalytic cofactor.

Glo1/2 are overexpressed around 3-5× in many breast cancers relative to normal mammary tissue, and enhanced expression of either one or both enzymes has also been observed in prostate, kidney, lung, colon, stomach, brain and ovarian cancers.[42, 43] This is a metabolic adaptation to counter the pro-apoptotic effect of MG accumulation in glycolytic tumors, which make Glo1 and Glo2 inhibitors attractive candidates for cancer therapeutics. Accordingly, another application of the present quantitative LC-MS/MS method is for monitoring the efficacy of glyoxalase inhibitors, which would induce a dose dependent increase in CEdG levels.

In sum, the new quantitative LC-MS/MS method for the measurement of CEdG improves upon (with purity and volume) and complements methods currently available for detecting protein AGEs, and allows for a more comprehensive evaluation of the role of nucleotide glycation in a wide range of human metabolic diseases, including those in which CEdG levels affect the disease.

Example 2

Materials:

CEdG calibrators and internal standards were synthesized as previously described.[71] LC-MS grade water with 0.1% formic acid (FA), acetonitrile (ACN), and ammonium hydroxide ($NH_4OH$) were purchased from Sigma Aldrich. Oasis MCX 1 cc solid phase extraction (SPE) columns were purchased from Waters Corporation. LC-MS Chromasolv® methanol (MeOH) was obtained from Fluka. 0.22 µm syringe filters, 4 mm, were purchased from Thermo Scientific.

Animal Care:

$Lepr^{wt/db}$ mice of C57BL/6J stock from The Jackson Laboratories were bred for five generations with C57BL/6 mice obtained in the City of Hope Animal Resource Center. All Lepr genotypes (wt, wt/db, and db/db) were generated from brother-sister mating of $Lepr^{wt/db}$ mice. Animals were housed in light-controlled conditions (10 h light/14 h dark cycle) at 22° C. for a maximum of nine months. All animals were provided with unlimited access to commercial chow (PicoLab Rodent Diet 20 #5053) and water. All procedures were approved under City of Hope IACUC Protocol #02016.

Genotyping:

Mouse DNA was isolated from 1-2 mm tail sections (200 µL 1×PBND Buffer [50 mM KCl, 10 mM Tris-HCl pH 8.3, 2.5 mM $MgCl_2$, 0.1 mg/mL Gelatin, 0.45% v/v NP-40, 0.45% v/v Tween-20] and 0.05 µg/µL Proteinase K) and digested overnight at 55° C. The Lepr site was amplified from 0.5 µL DNA with 1.25 U MyTaq polymerase (Bioline) in a 50 µL volume using Lepr-forward (5'-CCAACTTCC-CAACAGTCCAT-3', SEQ ID NO:1) and Lepr-reverse primers (5'-TGCCCTGAAAATCAAGCATA-3', SEQ ID NO:2). The presence of the db mutation was identified by digestion of 25 µL PCR product with 5 units of Hpy166II (New England Biolabs) in a 40 µL volume for 30 min at 37° C. The Lepr G→T mutation was revealed as 18 bp, 38 bp, and 131 bp bands (versus 38 bp and 149 bp for the wt allele).

Figure 21A:
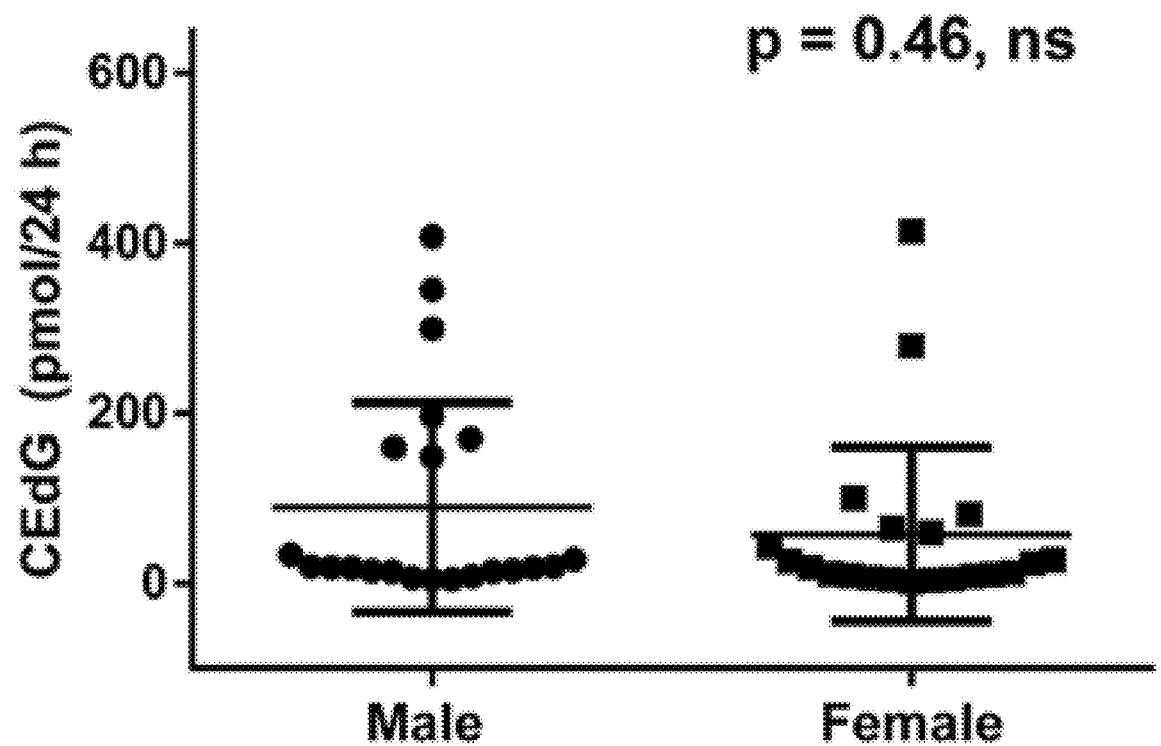
FIGS. 21A-21B. Gender specific differences for CEdG and FPG. Each data point represents the average value of CEdG (FIG. 21A) or FPG (FIG. 21B) for individual mice. Neither CEdG nor FPG achieved a significant difference based on gender.
Figure 21B:
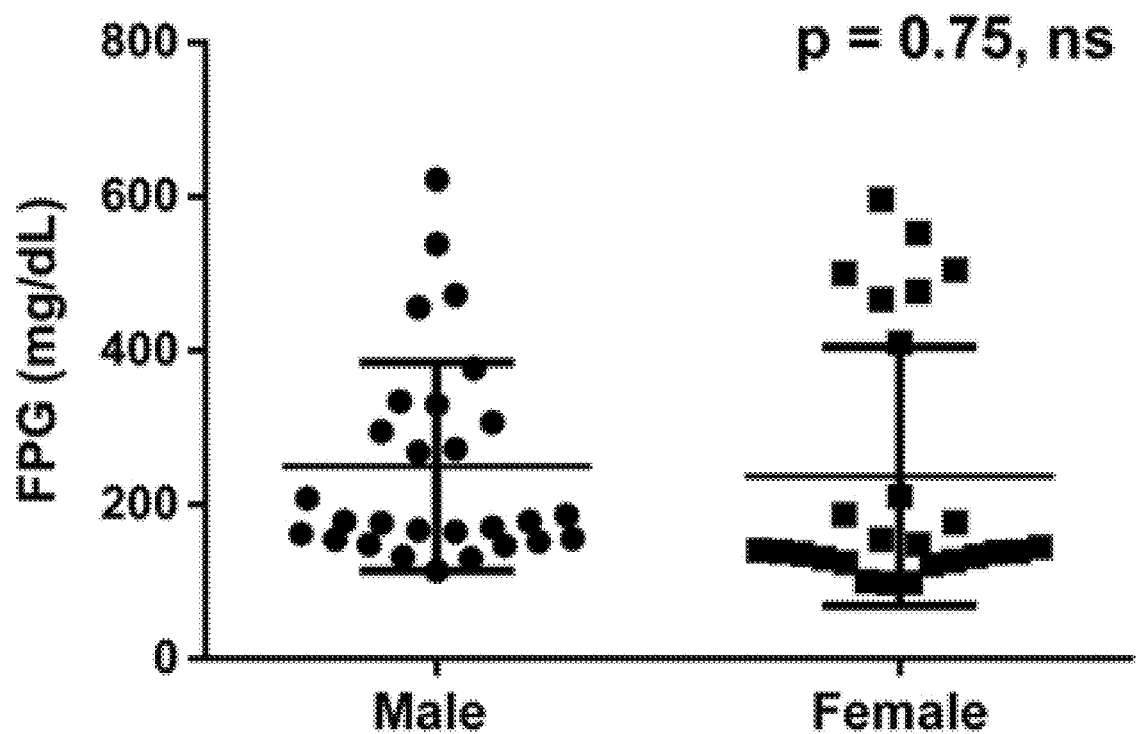

Urine, Blood, and Tissue Sample Collection:

A total of 38 mice were analyzed in this study (db/db n=11; wt/db n=16; wt n=11). Measurements commenced at 4 weeks of age immediately following completion of weaning. Mice were placed in metabolic cages (Nalgene) every 4 weeks for 24 h urine collection and provided with food and water ad libitum. The total volume of urine was recorded and stored at −20° C. Immediately following urine collection, mice were placed in clean cages and fasted for 6 h (10:30-16:30). Blood was collected after fasting by a small incision at the tip of the tail to measure FPG (Accu-Chek Aviva Blood Glucose Meter, Roche Diagnostics). 7 µL of blood was collected for HbA1c measurement using the Mouse Hemoglobin A1c assay (Crystal Chem Inc.). Equal numbers of male and female mice were used. No sex specific differences in CEdG or FPG levels were observed throughout the course of the study (FIGS. 21A and 21B). For tissue collection, mice were euthanized and perfused with PBS (pH 8) to obtain liver, kidney, pancreas, and colon tissues. Samples were then immediately flash-frozen in liquid N2 and stored at −80° C.

Figure 22A:
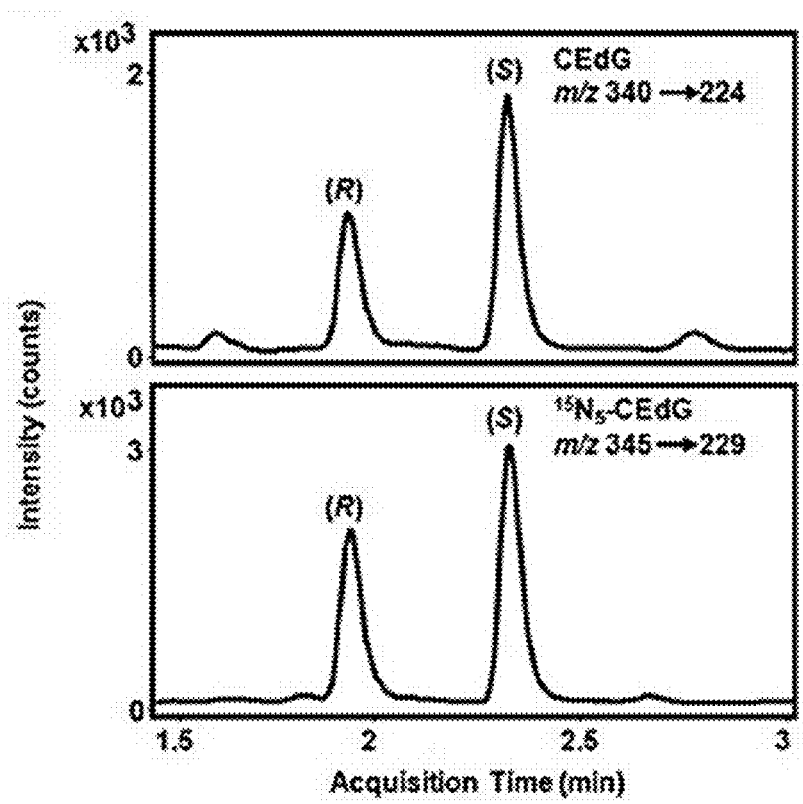
FIGS. 22A-22B. LC-ESI-MS/MS chromatogram of (R,S)-CEdG.

LC-ESI-MS/MS Analysis of CEdG in Urine:

Following thawing, 100 µL of urine was added to 50 µL of 7.5 ng/mL (R,S)-$^{15}N_5$-CEdG, and 400 µL 10% FA in $H_2O$. Oasis MCX 1 cc SPE columns were conditioned with 1 mL MeOH and equilibrated with 1 mL 0.1% FA in $H_2O$ prior to sample loading. Columns were washed with 2 mL MeOH and 2 mL 2% FA in $H_2O$. CEdG and its internal standard were eluted with 1 mL of 2% $NH_4OH$ in MeOH, dried by vacuum centrifugation, and resuspended in 100 µL 0.1% FA in $H_2O$. Calibration standards were processed in parallel to urine samples. Liquid chromatography was performed using an Agilent 1290 Infinity Binary UHPLC with an Agilent alkyl reversed-phase ZORBAX SB-Aq column (2.1×50 mm, 1.8 µm) (40° C.) using mobile phases A (0.1% FA in $H_2O$) and B (0.1% FA in ACN). Analytes were eluted using the following gradient: 0-4 min, 3-10% B; 4-4.5 min, 10-100% B; 4.5-5 min, 100-3% B, at a flow rate of 0.4 mL/min. R- and S-CEdG eluted at 1.9 and 2.4 min, respectively (FIG. 22A). Isotope-dilution LC-ESI-MS/MS was performed in positive ion mode using an Agilent 6400 triple quadrupole mass spectrometer with multiple reaction monitoring to observe mass transitions m/z 340.1→224.1 (CEdG) and m/z 345.1→229.1 ($^{15}N_5$-CEdG, FIG. 22B). The relative MS response of a fixed amount of (R, S)-$^{15}N_5$-CEdG to increasing concentrations of (R,S)-CEdG was used to generate a standard curve ($R^2$>0.99). Sample CEdG concentrations were determined using isotope dilution with fitting to the standard curve using the Agilent MassHunter Workstation Quantitative Analysis software. The lower limit of detection was 0.01 ng/mL (30 pM), while the lower limit of quantification, defined as a peak height of ≥5× baseline noise, was 0.1 ng/mL (0.3 nM). Inter- and intraday accuracy of the assay across the range of the standard curve was established to be 96 and 94% of target concentrations, respectively. The assay was also determined to be unbiased with both inter- and intraday precision within ±6%. Intra-run coefficients of variation (CV) were ≤9% and ≤8% for R- and S-CEdG, respectively, while the corresponding values for the inter-run CV were ≤9% and ≤7%. The final volume of urine excreted over 24 h was used to calculate total pmol CEdG, expressed as pmol CEdG/24 h.

Tissue DNA Isolation and Digestion:

Tissues were homogenized and DNA isolated as previously described[71] with the following modifications: Liver and kidney (0.05 g to 0.1 g) were homogenized in Buffer A (0.3 M sucrose, 60 mM KCl, 15 mM NaCl, 60 mM Tris-HCl, pH 8, 0.5 mM spermidine, 0.15 mM spermine, 2 mM EDTA) containing 0.5% Nonidet P-40 (NP-40). Nuclei were pelleted at 1100×g for 12 min at 4° C., after which supernatant was removed. The pellet was resuspended with 0.5 mL Buffer A then vortexed; 3 mL Buffer B (150 mM NaCl, 5 mM EDTA, pH 7.8), 3 mL Buffer C (20 mM Tris-HCl, pH 8, 20 mM NaCl, 20 mM EDTA, 1% SDS, and 80 µg/mL Proteinase K) were added with mixing after each step. For DNA isolation from pancreas and colon, tissue samples (0.05 to 0.1 g) were placed in a mortar with liquid nitrogen, and ground to a powder prior to processing using the procedure described above. 100 µg of isolated tissue DNA was spiked with $^{15}N_5$-(R, S) CEdG (final concentration of 3.75 ng/mL), and heated to 95° C. for 5 min followed by snap cooling on ice. DNA was digested as previously described.[72]

HPLC Analysis of dG from Genomic DNA:

Genomic DNA was analyzed using an Agilent 1100 HPLC system equipped with a 10×250 mm, 5 µm XBridge Prep C18 column (Waters). Nucleosides were separated using mobile phases A ($H_2O$ with 0.1% FA) and B (ACN with 0.1% FA). The following gradient was used: 0-15 min, 0-9% B; 15-55 min, 9.0-9.5% B; 55-60 min, 9.5-90% B; 60-70 min, 90% B; 70-75 min, 90-0% B; 75-80 min 0% B at 2 mL/min. Chromatograms and peak area measurements were analyzed using Agilent Chemstation software.

LC-ESI-MS/MS Analysis of CML and CEL:

CML and CEL were concentrated from urine and analyzed by the Analytical Pharmacology Core at City of Hope as previously described.[73]

Statistical Analyses of CEdG in Urine:

Statistical analyses between groups were performed using one-way ANOVA or Student's t-test. The diagnostic value of CEdG measurement to predict hyperglycemia was analyzed using R-statistical software employing a logistic regression analysis with a cutoff value set at the median value of all CEdG values measured (17 pmol/24 h). Normoglycemic animals were defined as 0 while hyperglycemic mice were defined as 1. Probability log odds were determined and the intercept for values greater than 17 were found to significantly predict hyperglycemia (FPG>200 mg/dL). The slope of the indicator variable (values of CEdG less than 17) was found to be −4.0943, with values lower than 17 to significantly predict normoglycemia. Expressed in another way, the logistic regression result showed that the indicator variable when CEdG<17 is statistically significant (p=0.0016). This means the indicator variable for CEdG expression <17 with a value of 0, versus CEdG with a value of 1, changes the log odds of being diabetic by −4.09. This data is presented in Table 2. The results for the 95% confidence interval analysis are also included as Table 3.

TABLE 2

Coefficients calculated for logistic regression analysis of CEdG as a predictor of a diabetic phenotype

|  | Coefficient | Std. Error | z value | p value |
|---|---|---|---|---|
| Intercept | 1.6094 | 0.7746 | 2.078 | 0.0377* |
| I(CEdG < 17) True | −4.0943 | 1.2974 | −3.156 | 0.0016** |

TABLE 3

95% Confidence interval for the intercept and slope used for logistic regression analysis

|  | 2.5% | 97.5% |
|---|---|---|
| Intercept | 0.276 | 3.482 |
| I(CEdG < 17) True | −7.322 | −1.904 |

Correlations (FPG vs. CEdG; HbA1c vs. CEdG) were determined by plotting the average CEdG values for individual mice with contemporaneous measurements. Spearman or Pearson correlation coefficients were determined using GraphPad Prism.

Genomic DNA Statistical Analyses:

CEdG values from genomic DNA for individual mice were separated by organ and glycemic status/genotype. As the variance in the raw CEdG values precluded accurate ANOVA analysis, these numbers were first converted to their natural log values. Comparisons between genotypes when organs were averaged for each individual animal were analyzed by taking the natural log of each CEdG value and then analyzing the differences using one-way ANOVA. To determine the effect of either organ or genotype on differences observed, average CEdG values for each organ or genotype were totaled and the natural log of each number calculated. One-way ANOVA was then used to determine statistical significance.

As demonstrated herein, CEdG was significantly elevated in urine of hyperglycemic mice.

Figure 22B:
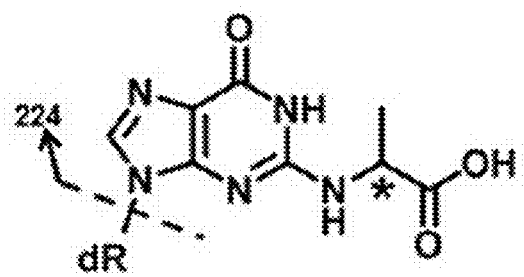
Figure 23B:
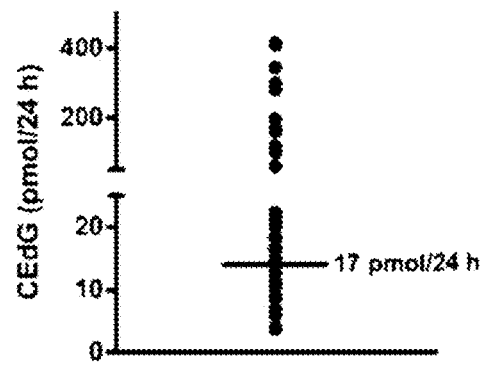

CEdG from 24 h urine collections were quantified using stable isotope dilution LC-ESI-MS/MS. The R- and S-stereoisomers of CEdG were cleanly resolved under the chromatographic conditions (FIG. 22A). Mass transitions m/z 340→224 and 345→229 for (R, S)-CEdG and $^{15}N_5$-(R, S)-CEdG, respectively, were used for identification and quantification (FIG. 22B). Separately measured values for R- and S-CEdG expressed as picomoles (pmol) of CEdG excreted over the 24 h urine collection period (pmol/24 h), were summed to provide a total CEdG measurement. Urinary CEdG levels differed significantly between hyperglycemic and normoglycemic animals (FIG. 23A). Each data point corresponds to an average CEdG value for an individual mouse measured monthly over a 36 week period. Mice with FPG≥200 mg/dL (11 mM) had a mean value of 238.4±112.8 pmol CEdG/24 h compared to 16.1±11.8 pmol CEdG/24 h for animals with FPG<200 mg/dL. There was no overlap in CEdG levels between the two groups. The median urinary CEdG value for all animals measured over the duration of the study was 17 pmol/24 h (FIG. 23B). Logistic regression analysis was performed to determine whether CEdG values above the median were predictive of hyperglycemia. A CEdG level ≥17 pmol/24 h was shown to be a significant predictor of hyperglycemia (p=0.0016; Table 2) as an isolated value, with a 95% confidence level (Table 3).

Figure 23C:
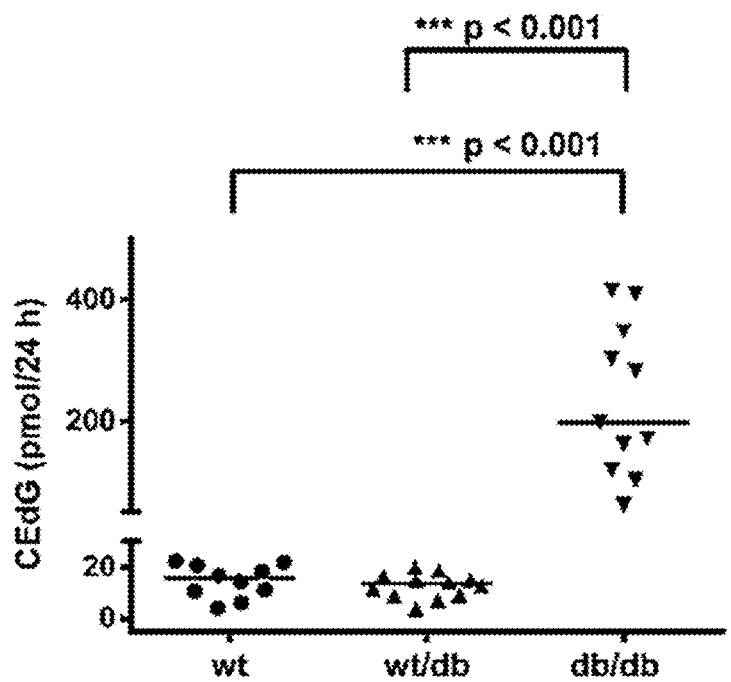

Because there was overlap of FPG and HbA1c values between wt, wt/db, and db/db mice (Table 4), it was of interest to determine whether CEdG measurement in urine could distinguish between genotypes. While db/db mice excreted significantly greater amounts of CEdG, compared to both wt and wt/db animals (FIG. 23C, p<0.001), the mean and median values for the latter two groups were not statistically different (Table 4).

TABLE 4

Summary of Metabolic Data

|  | $Lep_t^{db/db}$ | $Lep_t^{wt/db}$ | $Lep_t^{wt/wt}$ | All genotypes |
|---|---|---|---|---|
| CEdG (pmol/24 h) | | | | |
| Mean | 235.0 | 14.9 | 13.9 | 104.1 |
| SEM | 35.1 | 2.4 | 3.3 | 8.7 |
| Median | 197.1 | 13.6 | 14.3 | 17.1 |
| Range | 23.1-543.1 | 2.4-131.9 | 1.1-99.9 | 1.1-543.1 |
| N | 81 | 71 | 78 | 230 |
| HbA1c (%) | | | | |
| Mean | 9.4 (80)* | 5.0 (31) | 4.7 (28) | 6.8 (51) |
| SEM | 0.7 (7.3) | 0.1 (1.3) | 0.2 (1.7) | 0.4 (4.4) |
| Median | 9.1 (76) | 5.0 (32) | 4.8 (30) | 5.3 (34) |
| Range | 3.2-15.2 (11-143) | 3.7-5.8 (17-40) | 3.5-5.7 (15-39) | 3.2-15.2 (11-143) |

TABLE 4-continued

Summary of Metabolic Data

|  | $Lep_t^{db/db}$ | $Lep_t^{wt/db}$ | $Lep_t^{wt/wt}$ | All genotypes |
|---|---|---|---|---|
| N | 27 | 22 | 15 | 64 |
|  |  | FPG (mg/dL) |  |  |
| Mean | 412.6 | 154.0 | 147.4 | 237.9 |
| SEM | 18.0 | 4.9 | 3.8 | 9.5 |
| Median | 408 | 143 | 141 | 164 |
| Range | 106-978 | 86-448 | 70-239 | 70-978 |
| N | 103 | 98 | 108 | 309 |
|  |  | Mass (g) |  |  |
| Mean | 58.5 | 31.0 | 25.0 | 51.9 |
| SEM | 1.8 | 0.6 | 0.5 | 3.4 |
| Median | 64.7 | 31.6 | 23.7 | 31.3 |
| Range | 28.3-89.0 | 24.0-37.5 | 21.8-30.2 | 21.8-89.0 |
| N | 92 | 76 | 109 | 277 |

Data representing the mean, standard error of the mean (SEM), median, range, and number of measurements (n) for each parameter over the course of 36 weeks for all animals analyzed.
*Values in parentheses = mmol/mol HbA1c.

Followed over time for individual mice, CEdG in urine was found to increase significantly over time for the db/db animals (p=0.0023), whereas there was no significant increase for the wt and wt/db animals (FIG. 24 and Tables 5A and 5B).

TABLE 5A

Analysis within each group

| Group | Linear equation | p value |
|---|---|---|
| wt | Y = 0.41x + 2.87 | ns |
| wt/db | Y = −0.11x + 8.19 | ns |
| db/db | Y = 15.01x + 76.36 | 0.0023* |

TABLE 5B

Analysis between animals within each group

| Group | Between animal variation | Residual variation |
|---|---|---|
| wt | 0 | 168.14 |
| wt/db | 0 | 136.26 |
| db/db | 41059 | 84680 |

As demonstrated herein, urinary CEdG was positively correlated with FPG and HbA1c.

FPG and HbA1c measurements were obtained immediately after urine collection for CEdG following a 6 h fast. The db/db animals had the highest values of FPG and HbA1c, with mean values of 413 mg/dL and 9% (75 mmol/mol) respectively, vs. 147 mg/dL and 4.6% (27 mmol/mol) for wt animals (Table 4). Heterozygous wt/db and wt mice were indistinguishable based on their respective FPG or HbA1c values. A minimum expectation of any proposed biomarker for diabetes is that it shows some correlation with established biomarkers of metabolic disease. To examine the correlation between HbA1c and FPG with CEdG, plots of time-averaged measurements obtained contemporaneously for normoglycemic and hyperglycemic mice were analyzed using repeated measures analysis. FIG. 25A shows significant correlation between averaged CEdG and FPG (p≤0.001) while FIG. 25B reveals a similar relationship between CEdG and HbA1c (p≤0.001).

Figure 26:
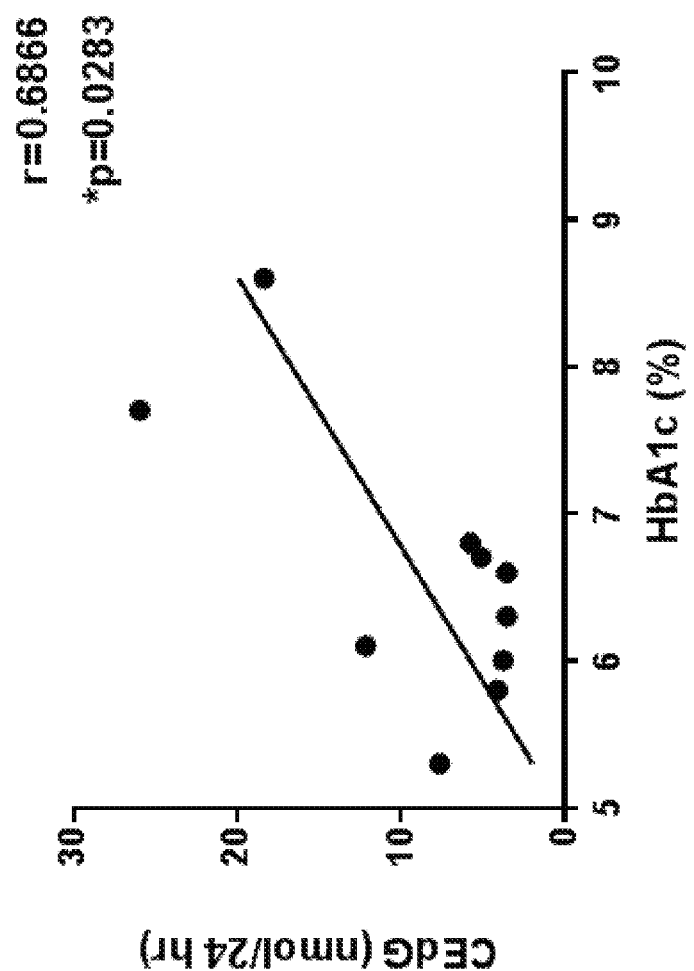
FIG. 26. CEdG significantly correlates with HbA1c in humans.
Figure 28A:
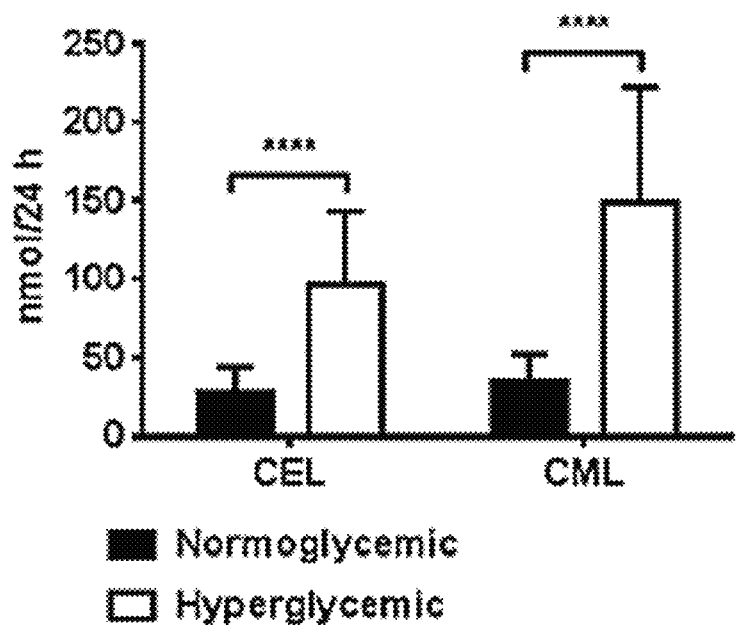
FIGS. 28A-28D. CEL and CML are elevated in urine of hyperglycemic mice and correlate with CEdG.
Figure 28B:
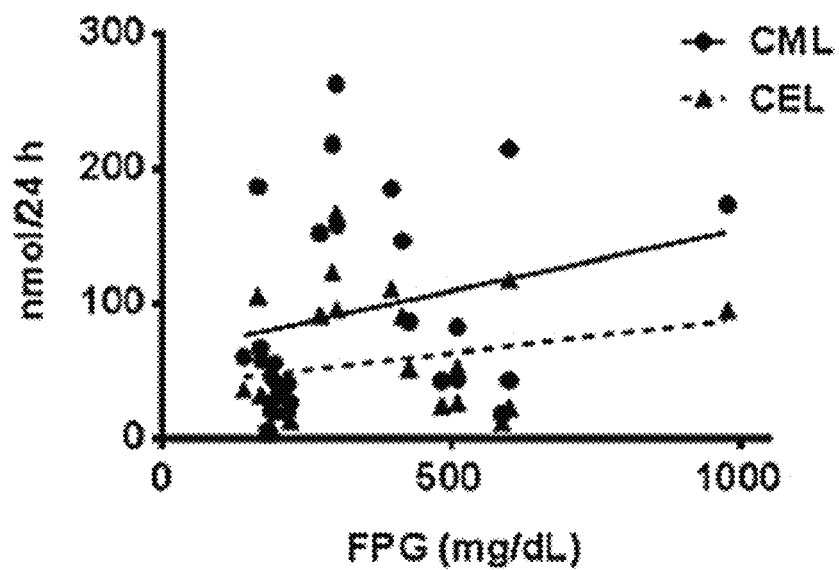
Figure 28C:
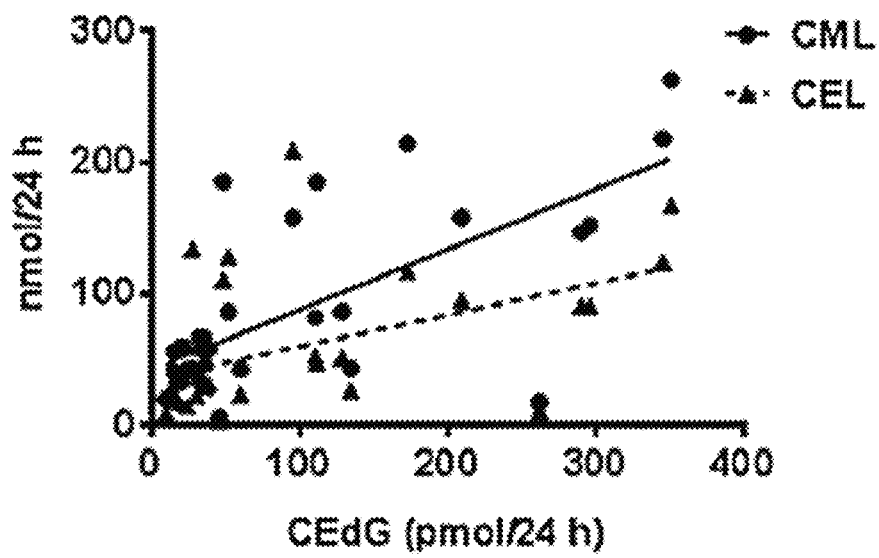
Figure 28D:
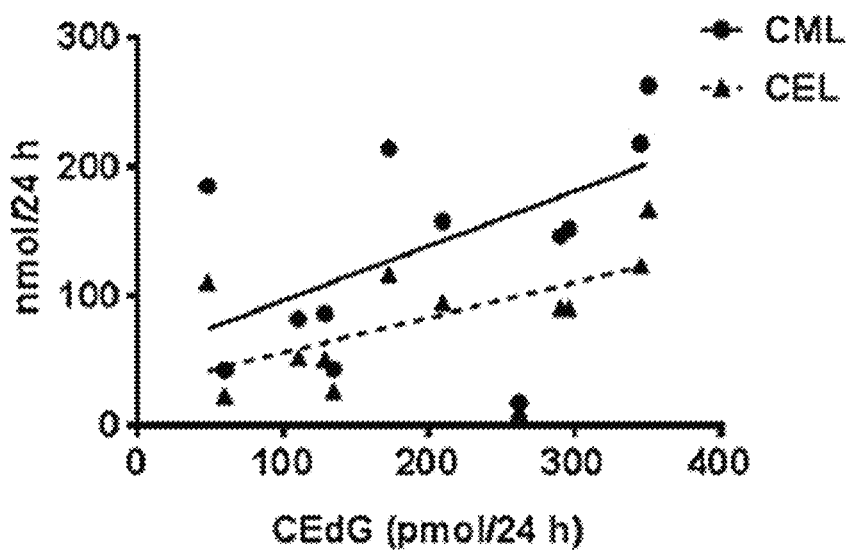

Using analytical methodologies described herein, urinary CEdG levels were measured. FIG. 26 further demonstrates that samples from both mice and humans showed correlations with HbA1c and/or FPG with both of these analytes.

As demonstrated herein, CEdG from tissue DNA was elevated in hyperglycemia and differentiated Lepr genotypes.

Genomic DNA was isolated from pancreas, kidney, colon, and liver from wt, wt/db, and db/db mice from 28-36 weeks of age and analyzed for CEdG. CEdG levels were normalized to the amount of dG present within each sample and expressed as $CEdG/10^6$ dG. To examine total organ differences between hyperglycemic and normoglycemic mice, CEdG values were averaged over colon, kidney, pancreas and liver for individual mice and plotted according to glycemic status in FIG. 27A. CEdG was significantly elevated in tissues from hyperglycemic mice (p<0.0001). Data from FIG. 27A was also stratified according to Lepr genotype, which revealed a trend of increasing CEdG from wt to wt/db and db/db mice (FIG. 27B). One-way ANOVA revealed a statistically significant difference between wt and db/db genotypes (p≤0.0001) as well as wt/db and db/db (p≤0.05). The distribution of CEdG in genomic DNA from individual tissues is shown in FIG. 27C, displaying a clear trend of CEdG levels in the order db/db>wt/db>wt. A statistically significant variation (p≤0.01) in CEdG levels was observed between db/db and wt mice in pancreas, colon, and kidney while liver displayed an even greater difference (p≤0.0001). In kidney a significant increase in CEdG was observed between db/db and wt/db mice (p≤0.05).

To minimize the effect of variance on inter-individual CEdG levels between organs, average CEdG values were calculated for each organ and differences between genotypes were analyzed using one-way ANOVA with Tukey's modification (last column in FIG. 27D). This analysis highlighted significant differences between all genotypes, most strikingly even between wt and wt/db mice (p≤0.01). Neither urinary CEdG, FPG or HbA1c measurements could make this distinction (Table 4).

As demonstrated herein, amino acid AGEs CML and CEL were elevated in hyperglycemic mice and correlate with CEdG.

The amino acid AGEs CEL and CML were measured in urine of age-matched (28 weeks) hyperglycemic and normoglycemic mice by LC-ESI-MS/MS with isotope dilution and their relationship to both FPG and CEdG was examined (FIG. 28). For mice with FPG≥200 mg/dL, CML and CEL were significantly elevated relative to normoglycemic animals (FIG. 28A). However, FPG did not appear to correlate with either CML or CEL (FIG. 28B). When the relationship between CEdG and CML/CEL for all animals was examined, a significant positive correlation was observed, more significantly for CML than CEL (FIG. 28C, p<0.0001). For the hyperglycemic subset of mice, CML and CEL were also positively correlated with CEdG (FIG. 28D).

Example 3

Conventionally diabetic nephropathy in mice is characterized by microalbuminuria. This example demonstrates the use of CEdG as a biomarker for diabetic complications such as nephropathy. The levels of markers for nephropathy such as albumin and creatinine do not change significantly until almost 50% of kidney function is compromised. Therefore, CEdG can serve as biomarkers for early stage diabetic complications.

Urinary CEdG (n=10) levels were measured in diabetic and control patients (City of Hope IRB #13188). Patients provided one 24 hour urine collection for analysis, at which time HbA1c was measured. Following collection, CEdG was enriched as described for mice (solid phase extraction) and measured using LC-MS/MS as described above. CEdG significantly correlated with HbA1c (FIG. 26).

Figure 29:
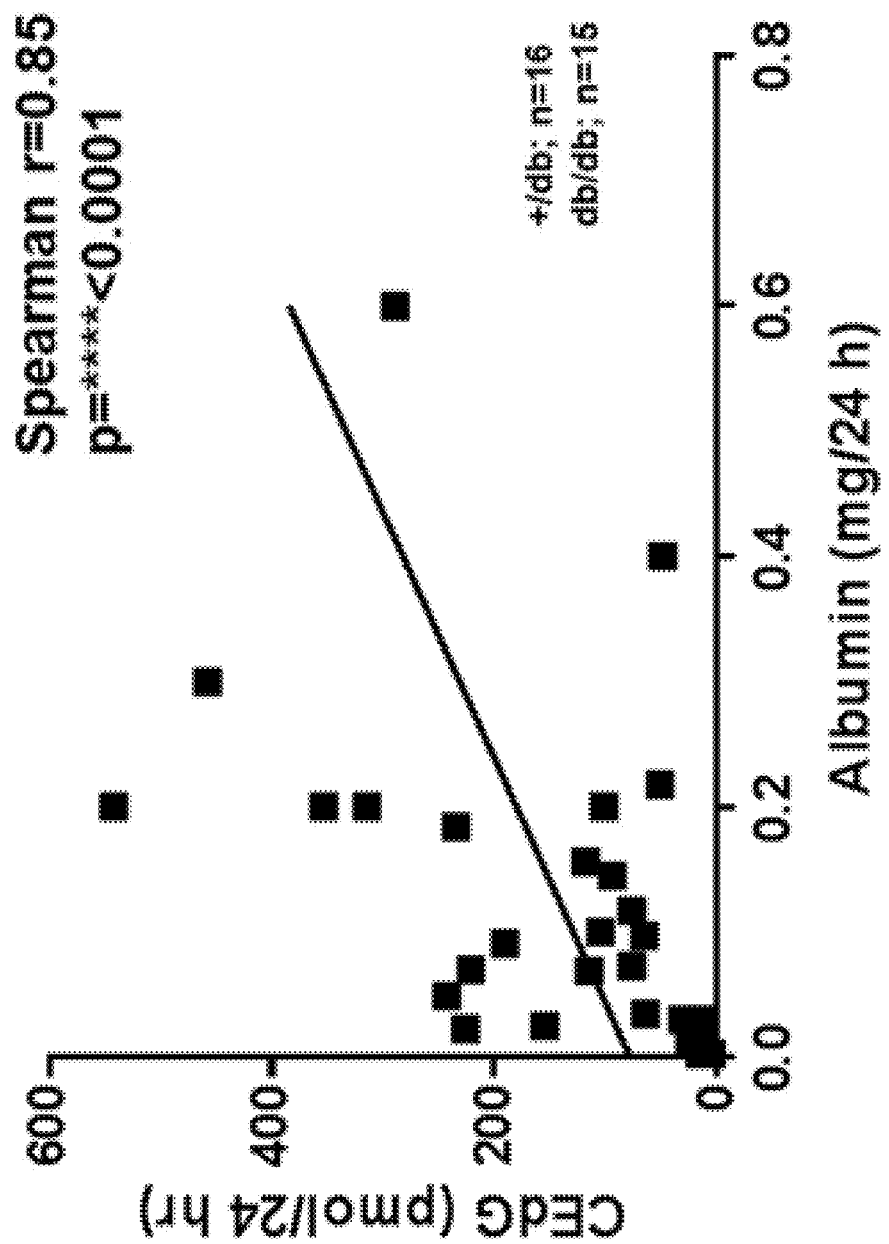
FIG. 29. CEdG significantly correlates with albumin alone.
Figure 30:
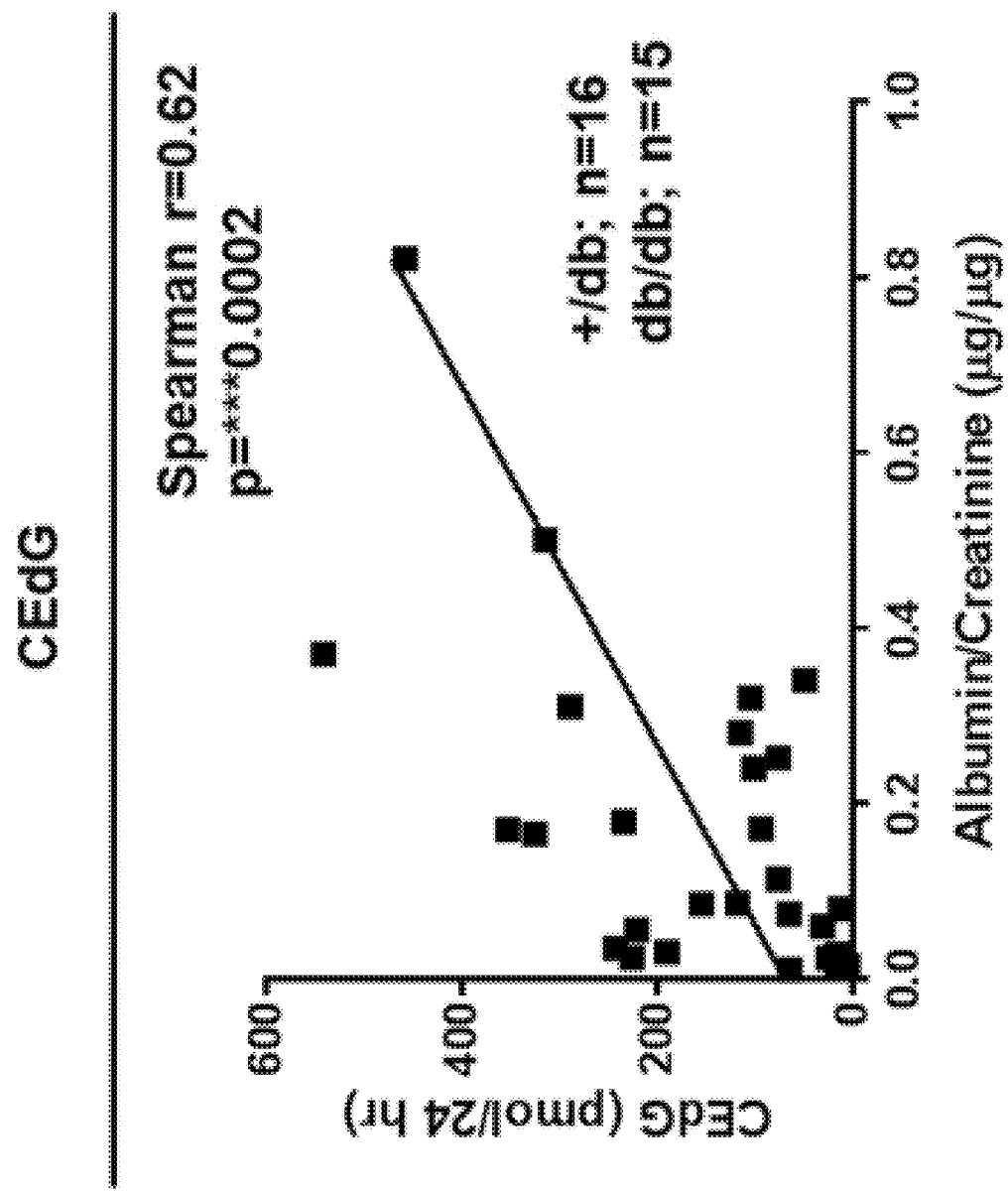
FIG. 30. CEdG significantly correlates with albumin when albumin was normalized to creatinine.
Figure 31A:
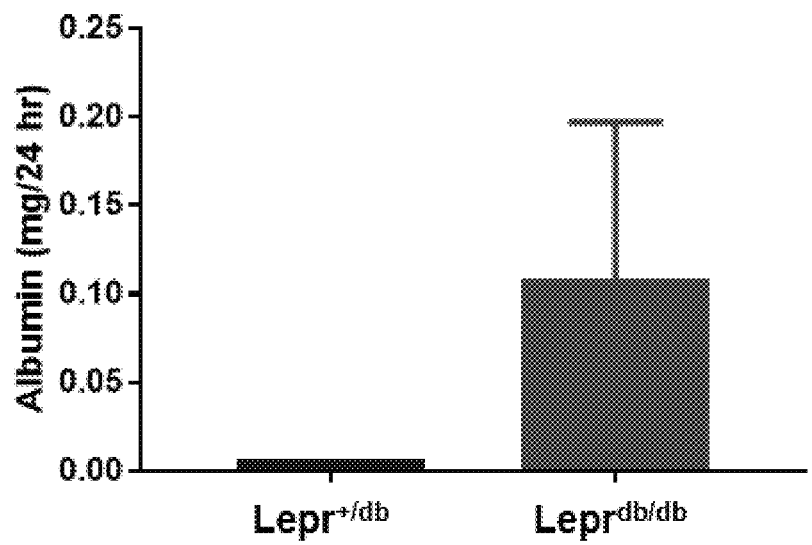
FIGS. 31A-31B. Albumin alone (FIG. 31A) and albumin normalized to creatinine (FIG. 31B) were both elevated in Lepr$^{db/db}$ mice compared to Lepr$^{+/db}$.
Figure 31B:
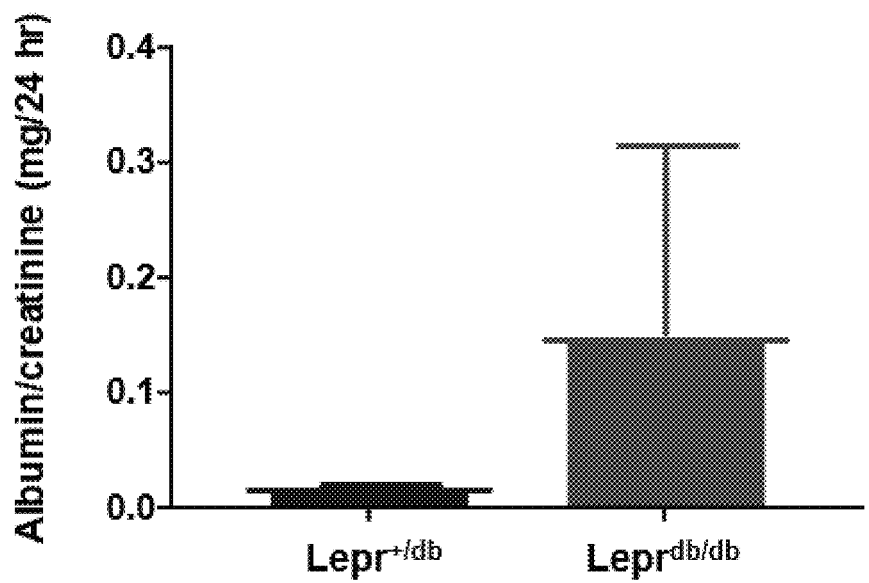

Urinary albumin levels were measured in $Lepr^{+/db}$ and $Lepr^{db/db}$ animals and normalized to creatinine (Abcam ELISA kit). Urinary albumin and CEdG were examined for any potential correlations. CEdG was found to significantly positively correlate with albumin alone (FIG. 29) and when albumin was normalized to creatinine (FIG. 30). Albumin alone and albumin/creatinine were both elevated in $Lepr^{db/db}$ mice compared to $Lepr^{+/db}$ (FIGS. 31A and 31B).

In sum, CEdG correlated significantly with albumin. Also, total albumin excreted over 24 hr correlated more significantly with CEdG compared to albumin normalized to creatinine. Individual CEdG and albumin time points correlated more strongly compared to repeated measures analysis.

The foregoing merely illustrates various embodiments. As such, the specific modifications discussed above are not to be construed as limitations on the scope of the disclosed products and methods. Equivalent embodiments are included within the contemplated scope. All references cited herein are incorporated by reference as if fully set forth herein.

REFERENCES (1) Nemet, I., Varga-Defterdarovic, L. and Turk, Z. (2006) Methylglyoxal in food and living organisms. *Mol. Nutr. Food Res.* 50, 1105-1117.
(2) Phillips, S. A. and Thornalley, P. J. (1993) The formation of methylglyoxal from triose phosphates. Investigation using a specific assay for methylglyoxal. *Eur J Biochem* 212, 101-105.
(3) Casazza, J. P., Felver, M. E. and Veech, R. L. (1984) The metabolism of acetone in rat. *J Biol Chem* 259, 231-236.
(4) Chaplen, F. W., Fahl, W. E. and Cameron, D. C. (1996) Detection of methylglyoxal as a degradation product of DNA and nucleic acid components treated with strong acid. *Anal Biochem* 236, 262-269.
(5) Murata-Kamiya, N., Kamiya, H., Kaji, H. and Kasai, H. (2000) Methylglyoxal induces G:C to C:G and G:C to T:A transversions in the supF gene on a shuttle vector plasmid replicated in mammalian cells. *Mutat Res* 468, 173-182.
(6) Lo, T. W., Selwood, T. and Thornalley, P. J. (1994) The reaction of methylglyoxal with aminoguanidine under physiological conditions and prevention of methylglyoxal binding to plasma proteins. *Biochem. Pharmacol.* 48, 1865-1870.
(7) Ahmed, N., and Thornalley, P. J. (2003) Quantitative screening of protein biomarkers of early glycation, advanced glycation, oxidation and nitrosation in cellular and extracellular proteins by tandem mass spectrometry multiple reaction monitoring. *Biochem. Soc. Trans.* 31, 1417-1422.
(8) Wautier, J. L. and Schmidt, A. M. (2004) Protein glycation: a firm link to endothelial cell dysfunction. *Circ Res* 95, 233-238.
(9) Yao, D., Taguchi, T., Matsumura, T., Pestell, R., Edelstein, D., Giardino, I., Suske, G., Ahmed, N., Thornalley, P. J., Sarthy, V. P., Hammes, H. P. and Brownlee, M. (2006) Methylglyoxal modification of mSin3A links glycolysis to angiopoietin-2 transcription. *Cell* 124, 275-286.
(10) Rahbar, S., Blumenfeld, O. and Ranney, H. M. (1969) Studies of an unusual hemoglobin in patients with diabetes mellitus. *Biochem Biophys Res Commun* 36, 838-843.
(11) Norberg, M., Eriksson, J. W., Lindahl, B., Andersson, C., Rolandsson, O., Stenlund, H. and Weinehall, L. (2006) A combination of HbA1c, fasting glucose and BMI is effective in screening for individuals at risk of future type 2 diabetes: OGTT is not needed. *J Intern Med* 260, 263-271.
(12) Edelman, D., Olsen, M. K., Dudley, T. K., Harris, A. C. and Oddone, E. Z. (2004) Utility of hemoglobin A1c in predicting diabetes risk. *J Gen Intern Med* 19, 1175-1180.
(13) Rosenstock, J., Sugimoto, D., Strange, P., Stewart, J. A., Soltes-Rak, E. and Dailey, G. (2006) Triple therapy in type 2 diabetes: insulin glargine or rosiglitazone added to combination therapy of sulfonylurea plus metformin in insulin-naive patients. *Diabetes Care* 29, 554-559.
(14) van Heijst, J. W., Niessen, H. W., Hoekman, K. and Schalkwijk, C. G. (2005) Advanced glycation end products in human cancer tissues: detection of Nepsilon-(carboxymethyl)lysine and argpyrimidine. *Ann N Y Acad Sci* 1043, 725-733.
(15) Frischmann, M., Bidmon, C., Angerer, J. and Pischetsrieder, M. (2005) Identification of DNA adducts of methylglyoxal. *Chem. Res. in Toxicol.* 18, 1586-1592.
(16) Papoulis, A., al-Abed, Y. and Bucala, R. (1995) Identification of N2-(1-carboxyethyl)guanine (CEG) as a guanine advanced glycosylation end product. *Biochemistry* 34, 648-655.
(17) Ochs, S. and Severin, T. (1994) Reaction of 2'-Deoxyguanosine with Glyceraldehyde. *Liebigs Ann Chem*, 851-853.
(18) Rahbar, S. (2007) Novel inhibitors of glycation and AGE formation. *Cell biochemistry and biophysics* 48, 147-157.
(19) Besaratinia, A., Bates, S. E., Synold, T. W., and Pfeifer, G. P. (2004) Similar mutagenicity of photoactivated porphyrins and ultraviolet A radiation in mouse embryonic fibroblasts: involvement of oxidative DNA lesions in mutagenesis. *Biochemistry* 43, 15557-15566.
(20) Phillips, S. A., Mirrlees, D. and Thornalley, P. J. (1993) Modification of the glyoxalase system in streptozotocin-induced diabetic rats. Effect of the aldose reductase inhibitor Statil. *Biochem Pharmacol* 46, 805-811.
(21) Figarola, J. L., Scott, S., Loera, S., Xi, B., Synold, T. and Rahbar, S. (2005) Renoprotective and lipid-lowering effects of LR compounds, novel advanced glycation end

(22) Figarola, J. L., Scott, S., Loera, S., Tessler, C., Chu, P., Weiss, L., Hardy, J. and Rahbar, S. (2003) LR-90 a new advanced glycation endproduct inhibitor prevents progression of diabetic nephropathy in streptozotocin-diabetic rats. *Diabetologia* 46, 1140-1152.

(23) Lo, T. W., Westwood, M. E., McLellan, A. C., Selwood, T., and Thornalley, P. J. (1994) Binding and modification of proteins by methylglyoxal under physiological conditions. A kinetic and mechanistic study with N alpha-acetylarginine, N alpha-acetylcysteine, and N alpha-acetyllysine, and bovine serum albumin. *J. Biol. Chem.* 269, 32299-32305.

(24) Wondrak, G. T., Cervantes-Laurean, D., Roberts, M. J., Qasem, J. G., Kim, M., Jacobson, E. L. and Jacobson, M. K. (2002) Identification of alpha-dicarbonyl scavengers for cellular protection against carbonyl stress. *Biochem Pharmacol* 63, 361-373.

(25) Thornalley, P. J., Yurek-George, A. and Argirov, O. K. (2000) Kinetics and mechanism of the reaction of aminoguanidine with the alpha-oxoaldehydes glyoxal, methylglyoxal, and 3-deoxyglucosone under physiological conditions. *Biochem Pharmacol* 60, 55-65.

(26) Avril, N., Menzel, M., Dose, J., Schelling, M., Weber, W., Janicke, F., Nathrath, W. and Schwaiger, M. (2001) Glucose metabolism of breast cancer assessed by 18F-FDG PET: histologic and immunohistochemical tissue analysis. *J Nucl Med* 42, 9-16.

(27) Bos, R., van Der Hoeven, J. J., van Der Wall, E., van Der Groep, P., van Diest, P. J., Comans, E. F., Joshi, U., Semenza, G. L., Hoekstra, O. S., Lammertsma, A. A. and Molthoff, C. F. (2002) Biologic correlates of (18)fluorodeoxyglucose uptake in human breast cancer measured by positron emission tomography. *J Clin Oncol* 20, 379-387.

(28) Vaca, C. E., Nilsson, J. A., Fang, J. L. and Grafstrom, R. C. (1998) Formation of DNA adducts in human buccal epithelial cells exposed to acetaldehyde and methylglyoxal in vitro. *Chemico-Biological Interactions* 108, 197-208.

(29) Godschalk, R. W., Maas, L. M., Kleinjans, J. C. and Van Schooten, F. J. (1998) Influences of DNA isolation and RNA contamination on carcinogen-DNA adduct analysis by 32P-postlabeling. *Environ. Mol. Mutagen.* 32, 344-350.

(30) Schneider, M., Georgescu, A., Bidmon, C., Tutsch, M., Fleischmann, E. H., Popov, D. and Pischetsrieder, M. (2006) Detection of DNA-bound advanced glycation endproducts by immunoaffinity chromatography coupled to HPLC-diode array detection. *Mo. Nutr. Food Res.* 50, 424-429.

(31) Li, H., Nakamura, S., Miyazaki, S., Morita, T., Suzuki, M., Pischetsrieder, M. and Niwa, T. (2006) N2-carboxyethyl-2'-deoxyguanosine, a DNA glycation marker, in kidneys and aortas of diabetic and uremic patients. *Kidney Int* 69, 388-392.

(32) Singh, R. and Farmer, P. B. (2006) Liquid chromatography-electrospray ionization-mass spectrometry: the future of DNA adduct detection. *Carcinogenesis* 27, 178-196.

(33) Koc, H. and Swenberg, J. A. (2002) Applications of mass spectrometry for quantitation of DNA adducts. *J. Chromatogr.* 778, 323-343.

(34) Bidmon, C., Frischmann, M. and Pischetsrieder, M. (2007) Analysis of DNA-bound advanced glycation endproducts by LC and mass spectrometry. *J. Chromatogr.* 855, 51-58.

(35) Seidel, W. and Pischetsrieder, M. (1998) DNA-glycation leads to depurination by the loss of N2-carboxyethylguanine in vitro. *Cell. Mol. Biol. (Noisy-le-Grand, France)* 44, 1165-1170.

(36) Cadet, J., D'Ham, C., Douki, T., Pouget, J. P., Ravanat, J. L. and Sauvaigo, S. (1998) Facts and artifacts in the measurement of oxidative base damage to DNA. *Free Radical Res* 29, 541-550.

(37) Rodriguez, H., Jurado, J., Laval, J. and Dizdaroglu, M. (2000) Comparison of the levels of 8-hydroxyguanine in DNA as measured by gas chromatography mass spectrometry following hydrolysis of DNA by *Escherichia coli* Fpg protein or formic acid. *Nucleic Acids Res* 28, E75.

(38) ESCODD, (2000) Comparison of different methods of measuring 8-oxoguanine as a marker of oxidative DNA damage. ESCODD (European Standards Committee on Oxidative DNA Damage). *Free Radic Res* 32, 333-341.

(39) Schupp, N., Schinzel, R., Heidland, A. and Stopper, H. (2005) Genotoxicity of advanced glycation end products: involvement of oxidative stress and of angiotensin II type 1 receptors. *Ann N Y Acad Sci* 1043, 685-695.

(40) Creighton, D. J. and Hamilton, D. S. (2001) Brief history of glyoxalase I and what we have learned about metal ion-dependent, enzyme-catalyzed isomerizations. *Arch Biochem Biophys* 387, 1-10.

(41) Thornalley, P. J. (1998) Glutathione-dependent detoxification of alpha-oxoaldehydes by the glyoxalase system: involvement in disease mechanisms and antiproliferative activity of glyoxalase I inhibitors. *Chemico-Biological Interactions* 111-112, 137-151.

(42) Rulli, A., Carli, L., Romani, R., Baroni, T., Giovannini, E., Rosi, G. and Talesa, V. (2001) Expression of glyoxalase I and II in normal and breast cancer tissues. *Breast Cancer Res Treat* 66, 67-72.

(43) Sakamoto, H., Mashima, T., Sato, S., Hashimoto, Y., Yamori, T. and Tsuruo, T. (2001) Selective activation of apoptosis program by S-p-bromobenzylglutathione cyclopentyl diester in glyoxalase I-overexpressing human lung cancer cells. *Clin Cancer Res* 7, 2513-2518.

(44) Kavarana, M. J., Kovaleva, E. G., Creighton, D. J., Wollman, M. B. and Eiseman, J. L. (1999) Mechanism-based competitive inhibitors of glyoxalase I: intracellular delivery, in vitro antitumor activities, and stabilities in human serum and mouse serum. *J Med Chem* 42, 221-228.

(45) Cao, H., Jiang, Y. and Wang, Y. (2007) Stereospecific synthesis and characterization of oligodeoxyribonucleotides containing an N2-(1-carboxyethyl)-2'-deoxyguanosine. *JACS* 129, 12123-12130.

(46) Pischetsrieder, M., Seidel, W., Munch, G. and Schinzel, R. (1999) N(2)-(1-Carboxyethyl)deoxyguanosine, a nonenzymatic glycation adduct of DNA, induces single-strand breaks and increases mutation frequencies. *Biochem Biophys Res Commun.* 264, 544-549.

(47) Lee, A. T., Plump, A., DeSimone, C., Cerami, A. and Bucala, R. (1995) A role for DNA mutations in diabetes-associated teratogenesis in transgenic embryos. *Diabetes* 44, 20-24.

(48) Eriksson, U. J., Wentzel, P., Minhas, H. S. and Thornalley, P. J. (1998) Teratogenicity of 3-deoxyglucosone and diabetic embryopathy. *Diabetes* 47, 1960-1966.

(49) La Vecchia, C., Negri, E., Franceschi, S., D'Avanzo, B., and Boyle, P. (1994) A case-control study of diabetes mellitus and cancer risk. *Br. J. Cancer.* 70, 950-953.

(50) Cowey, S., and Hardy, R. W. (2006) The metabolic syndrome: A high-risk state for cancer? *Am. J. Pathol.* 169, 1505-1522.
(51) Ahmed, N, Thornalley, P. J., Dawczynski, J., Franke, S., Strobel, J., Stein, G., Haik, G. M. (2003) Methylglyoxal-derived hydroimidazolone advanced glycation end-products of human lens proteins. *Invest Ophthalmol Vis Sci* 44, 5287-5292.
(52) Beisswenger, P. and Ruggiero-Lopez, D. (2003) Metformin inhibition of glycation processes. Diabetes Metab 29, 6S95-103.
(53) Bierhaus, A., Humpert, P. M., Morcos, M., Wendt, T., Chavakis, T., Arnold, B., Stern, D. M. and Nawroth, P. P. (2005) Understanding RAGE, the receptor for advanced glycation end products. J Mol Med 83, 876-886.
(54) Fosmark, D. S., Torjesen, P. A., Kilhovd, B. K., Berg, T. J., Sandvik, L., Hanssen, K. F., Agardh, C. D. and Agardh, E. (2006) Increased serum levels of the specific advanced glycation end product methylglyoxal-derived hydroimidazolone are associated with retinopathy in patients with type 2 diabetes mellitus. Metabolism: clinical and experimental 55, 232-236.
(55) Fukunaga, M., Miyata, S., Higo, S., Hamada, Y., Ueyama, S. and Kasuga, M. (2005) Methylglyoxal induces apoptosis through oxidative stress-mediated activation of p38 mitogen-activated protein kinase in rat Schwann cells. Ann N Y Acad Sci 1043, 151-157.
(56) Gaby, A. R. (2005) Adverse effects of dietary fructose. Altern Med Rev 10, 294-306.
(57) Han, Y., Randell, E., Vasdev, S., Gill, V., Gadag, V., Newhook, L. A., Grant, M. and Hagerty, D. (2007) Plasma methylglyoxal and glyoxal are elevated and related to early membrane alteration in young, complication-free patients with Type 1 diabetes. Mol Cell Biochem 305, 123-131.
(58) Li, Y., Dutta, U., Cohenford, M. A. and Dain, J. A. (2007) Nonenzymatic glycation of guanosine 5'-triphosphate by glyceraldehyde: an in vitro study of AGE formation. Bioorganic chemistry 35, 417-429.
(59) Miyata, T., van Ypersele de Strihou, C., Imasawa, T., Yoshino, A., Ueda, Y., Ogura, H., Kominami, K., Onogi, H., Inagi, R., Nangaku, M. and Kurokawa, K. (2001) Glyoxalase I deficiency is associated with an unusual level of advanced glycation end products in a hemodialysis patient. Kidney Int 60, 2351-2359.
(60) Price, D. L., Rhett, P. M., Thorpe, S. R. and Baynes, J. W. (2001) Chelating activity of advanced glycation end-product inhibitors. J Biol Chem 276, 48967-48972.
(61) Rahbar, S. (2005) The discovery of glycated hemoglobin: a major event in the study of nonenzymatic chemistry in biological systems. Ann N Y Acad Sci 1043, 9-19.
(62) Rahbar, S. and Figarola, J. L. (2003) Novel inhibitors of advanced glycation endproducts. Arch Biochem Biophys 419, 63-79.
(63) Schneider, M., Thoss, G., Hubner-Parajsz, C., Kientsch-Engel, R., Stahl, P. and Pischetsrieder, M. (2004) Determination of glycated nucleobases in human urine by a new monoclonal antibody specific for N2-carboxyethyl-2'-deoxyguanosine. Chemical research in toxicology 17, 1385-1390.
(64) Sebekova, K., Wagner, Z., Schupp, N. and Boor, P. (2007) Genomic damage and malignancy in end-stage renal failure: do advanced glycation end products contribute? Kidney Blood Press Res 30, 56-66.
(65) Seidel, W. and Pischetsrieder, M. (1998) Immunochemical detection of N2-[1-(1-carboxy)ethyl]guanosine, an advanced glycation end product formed by the reaction of DNA and reducing sugars or L-ascorbic acid in vitro. Biochimica et biophysica acta 1425, 478-484.
(66) Shinohara, M., Thornalley, P. J., Giardino, I., Beisswenger, P., Thorpe, S. R., Onorato, J. and Brownlee, M. (1998) Overexpression of glyoxalase-I in bovine endothelial cells inhibits intracellular advanced glycation end-product formation and prevents hyperglycemia-induced increases in macromolecular endocytosis. J Clin Invest 101, 1142-1147.
(67) Thornalley, P. J. (2003) Protecting the genome: defense against nucleotide glycation and emerging role of glyoxalase I overexpression in multidrug resistance in cancer chemotherapy. Biochem Soc Trans 31, 1372-1377.
(68) Vander Jagt, D. L. and Hunsaker, L. A. (2003) Methylglyoxal metabolism and diabetic complications: roles of aldose reductase, glyoxalase-I, betaine aldehyde dehydrogenase and 2-oxoaldehyde dehydrogenase. Chemico-biological interactions 143-144, 341-351.
(69) The effect of intensive treatment of diabetes on the development and progression of long-term complications in insulin-dependent diabetes mellitus. The Diabetes Control and Complications Trial Research Group. The New England journal of medicine. 1993; 329:977-986.
(70) Epidemiology of Diabetes Interventions and Complications (EDIC). Design, implementation, and preliminary results of a long-term follow-up of the Diabetes Control and Complications Trial cohort. Diabetes care. 1999; 22:99-111.
(71) Synold T, Xi B, Wuenschell G E, Tamae D, Figarola J L, Rahbar S, Termini J. Advanced glycation end products of DNA: quantification of N2-(1-Carboxyethyl)-2'-deoxyguanosine in biological samples by liquid chromatography electrospray ionization tandem mass spectrometry. Chemical research in toxicology. 2008; 21:2148-2155.
(72) Tamae D, Lim P, Wuenschell G E, Termini J. Mutagenesis and repair induced by the DNA advanced glycation end product N2-1-(carboxyethyl)-2'-deoxyguanosine in human cells. Biochemistry. 2011; 50:2321-2329.
(73) Figarola J L, Scott S, Loera S, Xi B, Synold T, Weiss L, Rahbar S. Prevention of early renal disease, dyslipidaemia and lipid peroxidation in STZ-diabetic rats by LR-9 and LR-74, novel AGE inhibitors. Diabetes/metabolism research and reviews. 2005; 21:533-544.

The invention claimed is:

1. A method of detecting diabetes in a subject comprising:
   (i) quantifying a $N^2$-carboxyethyl-2'-deoxyguanosine (CEdG) level in a urine sample from the subject comprising:
      (a) performing a liquid chromatography electrospray ionizing tandem mass spectrometry (LC-ESI-MS/MS) assay on the urine sample using a stable isotope dilution comprising using an internal $^{15}N_5$-carboxyethyl-2'-deoxyguanosine ($^{15}N_5$-CEdG) standard comprising stereochemically pure (R) and stereochemically pure (S)$^{15}N_5$-CEdG; and
      (b) measuring the CEdG level in the urine sample; and
   (ii) determining the subject has diabetes when the CEdG level in the urine sample is elevated as compared to a normal physiological CEdG level.

2. The method of claim 1, further comprising preventing artifactual CEdG formation by adding aminoguanidine and/or D-penicillamine to the sample prior to quantifying the CEdG level in the sample.

3. The method of claim 1, wherein quantifying the level of CEdG comprises quantifying the level of CEdG (S) and CEdG (R).

4. The method of claim 1, wherein the internal $^{15}N_5$-CEdG standard comprises oligonucleotides containing stereochemically pure $^{15}N_5$-CEdG (R) and oligonucleotides containing stereochemically pure $^{15}N_5$-CEdG (S).

5. The method of claim 4, further comprising preventing artifactual CEdG formation by adding aminoguanidine and/or D-penicillamine to the sample prior to quantifying the CEdG level in the sample.

6. The method of claim 1, further comprising administering a treatment for diabetes to the subject determined to have diabetes.

7. A method of detecting diabetes in a subject comprising:
   (i) quantifying a $N^2$-carboxyethyl-2'-deoxyguanosine (CEdG) level in a urine sample from the subject comprising using an internal $^{15}N_5$-carboxyethyl-2'-deoxyguanosine ($^{15}N_5$-CEdG) standard comprising stereochemically pure (R) and stereochemically pure (S)$^{15}N_5$-CEdG; and
   (ii) determining the subject has diabetes when the CEdG level in the urine sample is elevated as compared to a normal physiological CEdG level.

8. The method of claim 7, further comprising preventing artifactual CEdG formation by adding aminoguanidine and/or D-penicillamine to the sample prior to quantifying the CEdG level in the sample.

9. The method of claim 7, wherein quantifying the level of CEdG comprises quantifying the level of CEdG (S) and CEdG (R).

10. The method of claim 7, wherein the internal $^{15}N_5$-CEdG standard comprises oligonucleotides containing stereochemically pure $^{15}N_5$-CEdG (R) and oligonucleotides containing stereochemically pure $^{15}N_5$-CEdG (S).

11. The method of claim 9, further comprising preventing artifactual CEdG formation by adding aminoguanidine and/or D-penicillamine to the sample prior to quantifying the CEdG level in the sample.

12. The method of claim 11, wherein quantifying a CEdG level in a urine sample from the subject comprises:
   (a) performing a liquid chromatography electrospray ionizing tandem mass spectrometry (LC-ESI-MS/MS) assay on the urine sample using a stable isotope dilution using the internal $^{15}N_5$-CEdG standard; and
   (b) measuring the CEdG level in the urine sample.

13. The method of claim 7, further comprising administering a treatment for diabetes to the subject determined to have diabetes.

* * * * *

UNITED STATES PATENT AND TRADEMARK OFFICE
CERTIFICATE OF CORRECTION

| | | |
|---|---|---|
| PATENT NO. | : 11,179,361 B2 | Page 1 of 1 |
| APPLICATION NO. | : 15/887857 | |
| DATED | : November 23, 2021 | |
| INVENTOR(S) | : Samuel Rahbar et al. | |

It is certified that error appears in the above-identified patent and that said Letters Patent is hereby corrected as shown below:

In the Specification

Government Interest section, Column 1, Lines 23-26, please delete:
"The present invention was made partially with government support under Grant Nos. P30 CA33572, and R01CA176611, awarded by National Institutes of Health. The government has certain rights in the present invention."

And insert:
--This invention was made with government support under R01 CA176611, and P30 CA033572 awarded by the National Institutes of Health. The government has certain rights in the invention.--

Signed and Sealed this
First Day of July, 2025

Coke Morgan Stewart
*Acting Director of the United States Patent and Trademark Office*

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Lepr-forward primer
```

```
<400> SEQUENCE: 1
ccaacttccc aacagtccat                                              20

<210> SEQ ID NO 2
<211> LENGTH: 20
<212> TYPE: DNA
<213> ORGANISM: Artificial Sequence
<220> FEATURE:
<223> OTHER INFORMATION: Lepr-reverse primer

<400> SEQUENCE: 2
tgccctgaaa atcaagcata                                              20
```